(12) United States Patent
Hua et al.

(10) Patent No.: US 12,335,342 B2
(45) Date of Patent: Jun. 17, 2025

(54) TRANSMITTING ANALYTE DATA USING LOW-POWER INSTRUCTION SETS

(71) Applicant: ABBOTT DIABETES CARE INC., Alameda, CA (US)

(72) Inventors: Xuandong Hua, Mountain View, CA (US); Yongjian Wu, Saratoga, CA (US); Danny Chan, Daly City, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 342 days.

(21) Appl. No.: 17/581,620

(22) Filed: Jan. 21, 2022

(65) Prior Publication Data

US 2022/0150308 A1    May 12, 2022

Related U.S. Application Data

(63) Continuation-in-part of application No. 16/934,592, filed on Jul. 21, 2020, now Pat. No. 11,317,803.
(Continued)

(51) Int. Cl.
*H04W 4/80*    (2018.01)
*A61B 5/00*    (2006.01)
(Continued)

(52) U.S. Cl.
CPC .............. *H04L 67/12* (2013.01); *H04L 12/12* (2013.01); *H04L 67/14* (2013.01); *A61B 5/0004* (2013.01)

(58) Field of Classification Search
None
See application file for complete search history.

(56) References Cited

U.S. PATENT DOCUMENTS

| 4,561,443 A | 12/1985 | Hogrefe et al. |
| 5,390,671 A | 2/1995 | Lord et al. |

(Continued)

FOREIGN PATENT DOCUMENTS

| EP | 2 407 094 | 1/2012 |
| EP | 2 498 196 A2 | 9/2012 |

(Continued)

OTHER PUBLICATIONS

Chuang et al., "Pilot Studies of Transdermal Continuous Glucose Measurement in Outpatient Diabetic Patients and in Patients during and after Cardiac Surgery," Journal of Diabetes Science and Technology, 595-602 (2008).
(Continued)

*Primary Examiner* — Tuan A Tran
(74) *Attorney, Agent, or Firm* — Baker Botts L.L.P.

(57) ABSTRACT

Embodiments described herein include an analyte monitoring device. The analyte monitoring device generates sensor data indicative of an analyte level measured by an analyte sensor transcutaneously positioned in contact with a bodily fluid of the subject. The analyte monitoring device initializes a communication module using an advertisement scanning related instruction set, wherein the advertisement scanning related instruction set is a subset of a communications protocol startup instruction set including the advertisement scanning related instruction set and a non-advertisement scanning related instruction set. The analyte monitoring device issues one or more advertising packets and receives a connection request from a receiving device. The analyte monitoring device completes initialization of the communication module using the non-advertisement scanning related instruction set. The analyte monitoring device selects a subset of the sensor data, prepares a data packet comprising
(Continued)

the subset of the sensor data, and transmits the data packet to the receiving device.

20 Claims, 11 Drawing Sheets

Related U.S. Application Data

(60) Provisional application No. 63/292,953, filed on Dec. 22, 2021, provisional application No. 63/252,120, filed on Oct. 4, 2021.

(51) Int. Cl.
| | |
|---|---|
| *G06F 1/26* | (2006.01) |
| *H01L 23/34* | (2006.01) |
| *H04L 12/12* | (2006.01) |
| *H04L 67/12* | (2022.01) |
| *H04L 67/14* | (2022.01) |
| *H04W 48/10* | (2009.01) |
| *H04W 52/02* | (2009.01) |
| *H04W 76/14* | (2018.01) |

(56) References Cited

U.S. PATENT DOCUMENTS

| | | | |
|---|---|---|---|
| 5,482,473 A | 1/1996 | Lord et al. | |
| 5,660,163 A | 8/1997 | Schulman et al. | |
| 5,690,119 A | 11/1997 | Rytky et al. | |
| 6,096,268 A | 8/2000 | Inbar | |
| 6,141,774 A | 10/2000 | Mattheis | |
| 6,159,181 A | 12/2000 | Crossman et al. | |
| 6,175,752 B1 | 1/2001 | Say et al. | |
| 6,266,551 B1 | 7/2001 | Osadchy et al. | |
| 6,293,925 B1 | 9/2001 | Safabash et al. | |
| 6,298,255 B1 | 10/2001 | Cordero et al. | |
| 6,560,471 B1 | 5/2003 | Heller et al. | |
| 6,565,509 B1 | 5/2003 | Say et al. | |
| 6,689,056 B1 | 2/2004 | Kilcoyne et al. | |
| 6,695,860 B1 | 2/2004 | Ward et al. | |
| 7,344,500 B2 | 3/2008 | Talbot et al. | |
| 7,643,798 B2 | 1/2010 | Ljung | |
| 7,672,722 B1 | 3/2010 | Mengotto | |
| 7,693,485 B2 | 4/2010 | Parys | |
| 8,145,279 B2 * | 3/2012 | Kim | H04W 52/0229 455/574 |
| 8,401,194 B2 | 3/2013 | Nierzwick et al. | |
| 8,488,506 B2 * | 7/2013 | Husted | G06F 1/3234 455/574 |
| 8,544,106 B2 | 9/2013 | Haider et al. | |
| 9,000,914 B2 | 4/2015 | Baker et al. | |
| 9,211,065 B2 | 12/2015 | Marsh et al. | |
| 9,344,777 B2 | 5/2016 | He et al. | |
| 9,634,496 B2 * | 4/2017 | Elad | H02J 5/005 |
| 9,678,763 B2 * | 6/2017 | Park | H04N 21/4432 |
| 9,681,381 B2 * | 6/2017 | Kang | H04W 4/80 |
| 9,687,658 B2 * | 6/2017 | Wu | A61N 1/37223 |
| 9,853,969 B2 * | 12/2017 | Enke | H04W 4/80 |
| 9,855,433 B2 * | 1/2018 | Shahandeh | A61N 1/37252 |
| 9,907,150 B2 * | 2/2018 | Roquemore, III | G06F 21/74 |
| 9,980,140 B1 | 5/2018 | Spencer et al. | |
| 9,992,439 B2 * | 6/2018 | Lee | H04N 21/42204 |
| 10,045,296 B2 * | 8/2018 | Vasishtha | H04W 4/80 |
| 10,124,176 B2 | 11/2018 | Wu et al. | |
| 10,182,336 B1 | 1/2019 | Stockton et al. | |
| 10,313,860 B2 * | 6/2019 | Montemurro | H04W 52/0212 |
| 10,375,222 B2 | 8/2019 | Mandapaka et al. | |
| 10,390,225 B2 * | 8/2019 | Mao | H04L 63/107 |
| 10,397,869 B2 * | 8/2019 | Zacchio | H04W 88/06 |
| 10,449,372 B2 | 10/2019 | Wu et al. | |
| 10,543,370 B2 | 1/2020 | Doudna et al. | |
| 10,552,614 B2 * | 2/2020 | Nguyen | G06F 9/4418 |
| 10,617,875 B2 * | 4/2020 | Demmer | H04L 43/103 |
| 10,834,563 B2 * | 11/2020 | Lo | H04W 52/0229 |
| 10,863,432 B2 * | 12/2020 | Dunsbergen | G06F 1/3206 |
| 11,007,370 B2 * | 5/2021 | Shahandeh | A61N 1/37217 |
| 11,018,071 B2 * | 5/2021 | Pinkham | G06F 1/206 |
| 11,032,686 B2 * | 6/2021 | Montemurro | H04W 36/0061 |
| 11,065,457 B2 * | 7/2021 | Wang | A61N 1/37276 |
| 11,243,595 B2 * | 2/2022 | Cheng | G06F 3/167 |
| 11,290,954 B2 * | 3/2022 | Li | H04W 52/028 |
| 11,337,151 B2 * | 5/2022 | Shaw | H04W 76/11 |
| 11,452,881 B2 * | 9/2022 | Sturman | G16H 40/63 |
| 11,457,810 B2 * | 10/2022 | Van Tassel | H04W 12/50 |
| 11,534,618 B2 * | 12/2022 | Sturman | H04W 4/06 |
| 11,991,175 B2 | 5/2024 | Rolfe et al. | |
| 12,144,580 B2 * | 11/2024 | Wu | G06F 12/0238 |
| 2002/0109621 A1 | 8/2002 | Khair et al. | |
| 2003/0028184 A1 | 2/2003 | Lebel et al. | |
| 2003/0050009 A1 | 3/2003 | Kurisko et al. | |
| 2003/0100821 A1 | 5/2003 | Heller et al. | |
| 2003/0144581 A1 | 7/2003 | Conn et al. | |
| 2003/0153900 A1 | 8/2003 | Aceti et al. | |
| 2004/0106860 A1 | 6/2004 | Say et al. | |
| 2004/0117204 A1 | 6/2004 | Mazar et al. | |
| 2004/0122353 A1 | 6/2004 | Shahmirian et al. | |
| 2004/0127958 A1 | 7/2004 | Mazar et al. | |
| 2004/0133164 A1 | 7/2004 | Funderburk et al. | |
| 2005/0027463 A1 | 2/2005 | Goode, Jr. et al. | |
| 2005/0049501 A1 | 3/2005 | Conero et al. | |
| 2005/0101912 A1 | 5/2005 | Faust et al. | |
| 2005/0177398 A1 | 8/2005 | Watanabe et al. | |
| 2005/0204134 A1 | 9/2005 | Von Arx et al. | |
| 2005/0240245 A1 | 10/2005 | Bange et al. | |
| 2005/0242479 A1 | 11/2005 | Petisce et al. | |
| 2005/0261563 A1 | 11/2005 | Zhou et al. | |
| 2005/0283114 A1 | 12/2005 | Bresina et al. | |
| 2005/0283208 A1 | 12/2005 | Von Arx et al. | |
| 2006/0016700 A1 | 1/2006 | Brister et al. | |
| 2006/0019327 A1 | 1/2006 | Brister et al. | |
| 2006/0025663 A1 | 2/2006 | Talbot et al. | |
| 2006/0081469 A1 | 4/2006 | Lee | |
| 2007/0038044 A1 | 2/2007 | Dobbles et al. | |
| 2007/0043279 A1 | 2/2007 | Mannheimer et al. | |
| 2007/0060801 A1 | 3/2007 | Neinast | |
| 2007/0073129 A1 | 3/2007 | Shah et al. | |
| 2007/0142727 A1 | 6/2007 | Zhang et al. | |
| 2007/0173710 A1 | 7/2007 | Petisce et al. | |
| 2007/0219480 A1 | 9/2007 | Kamen et al. | |
| 2007/0255116 A1 | 11/2007 | Mehta et al. | |
| 2007/0288265 A1 | 12/2007 | Quinian et al. | |
| 2008/0009805 A1 | 1/2008 | Ethelfeld | |
| 2008/0097246 A1 | 4/2008 | Stafford | |
| 2008/0129486 A1 | 6/2008 | Jeckelmann et al. | |
| 2008/0269687 A1 | 10/2008 | Chong et al. | |
| 2008/0275313 A1 | 11/2008 | Brister et al. | |
| 2008/0278333 A1 | 11/2008 | Fennell et al. | |
| 2008/0300476 A1 | 12/2008 | Stafford | |
| 2008/0312512 A1 | 12/2008 | Brukalo et al. | |
| 2008/0319414 A1 | 12/2008 | Yodfat et al. | |
| 2009/0054737 A1 | 2/2009 | Magar et al. | |
| 2009/0112626 A1 | 4/2009 | Talbot et al. | |
| 2009/0240193 A1 | 9/2009 | Mensinger et al. | |
| 2009/0291634 A1 | 11/2009 | Saarisalo | |
| 2010/0014626 A1 | 1/2010 | Fennell et al. | |
| 2010/0045425 A1 | 2/2010 | Chivallier | |
| 2010/0141400 A1 * | 6/2010 | Radulescu | H04W 52/0225 340/10.33 |
| 2010/0198034 A1 | 8/2010 | Thomas et al. | |
| 2010/0198142 A1 | 8/2010 | Sloan et al. | |
| 2010/0230285 A1 | 9/2010 | Hoss et al. | |
| 2010/0274218 A1 | 10/2010 | Yodfat et al. | |
| 2010/0302979 A1 | 12/2010 | Reunamäki | |
| 2010/0327063 A1 | 12/2010 | Medina et al. | |
| 2011/0058485 A1 | 3/2011 | Sloan | |
| 2011/0125000 A1 | 5/2011 | Rantala | |
| 2011/0177780 A1 | 7/2011 | Sato et al. | |
| 2011/0193704 A1 | 8/2011 | Harper et al. | |
| 2011/0210830 A1 | 9/2011 | Talty et al. | |
| 2011/0213225 A1 | 9/2011 | Bernstein et al. | |
| 2011/0282671 A1 | 11/2011 | Dicks et al. | |
| 2011/0320130 A1 | 12/2011 | Valdes et al. | |
| 2012/0003933 A1 | 1/2012 | Baker et al. | |

(56) References Cited

U.S. PATENT DOCUMENTS

| | | | |
|---|---|---|---|
| 2012/0078071 A1 | 3/2012 | Bohm et al. | |
| 2012/0084053 A1 | 4/2012 | Yuen et al. | |
| 2012/0123227 A1 | 5/2012 | Sun et al. | |
| 2012/0182917 A1 | 7/2012 | Edlund | |
| 2012/0237022 A1 | 9/2012 | Berson et al. | |
| 2012/0255875 A1 | 10/2012 | Vicente et al. | |
| 2012/0260323 A1 | 10/2012 | San Vicente et al. | |
| 2012/0265035 A1 | 10/2012 | Bohm et al. | |
| 2012/0309302 A1 | 12/2012 | Buhot | |
| 2013/0078912 A1 | 3/2013 | San Vicente et al. | |
| 2013/0310896 A1 | 11/2013 | Mass | |
| 2014/0206346 A1* | 7/2014 | Kiukkonen | H04W 52/028 |
| | | | 455/426.1 |
| 2014/0266776 A1 | 9/2014 | Miller et al. | |
| 2014/0266785 A1 | 9/2014 | Miller et al. | |
| 2014/0273858 A1 | 9/2014 | Panther et al. | |
| 2014/0313052 A1 | 10/2014 | Yarger et al. | |
| 2014/0379273 A1 | 12/2014 | Petisce et al. | |
| 2015/0038818 A1 | 2/2015 | Cole | |
| 2015/0065047 A1 | 3/2015 | Wu et al. | |
| 2015/0089222 A1 | 3/2015 | White et al. | |
| 2015/0118658 A1 | 4/2015 | Mayou et al. | |
| 2015/0123810 A1 | 5/2015 | Hernandez-Rosas et al. | |
| 2015/0164391 A1 | 6/2015 | Hernandez-Rosas et al. | |
| 2015/0205947 A1 | 7/2015 | Berman et al. | |
| 2015/0207796 A1 | 7/2015 | Love et al. | |
| 2015/0289124 A1 | 10/2015 | Palin et al. | |
| 2015/0319674 A1* | 11/2015 | Hughes | H04W 52/0209 |
| | | | 455/41.2 |
| 2015/0382304 A1* | 12/2015 | Park | H04W 56/001 |
| | | | 455/41.2 |
| 2016/0066826 A1 | 3/2016 | Larvenz et al. | |
| 2016/0081597 A1 | 3/2016 | Bhavaraju et al. | |
| 2016/0165649 A1 | 6/2016 | Polo et al. | |
| 2016/0210099 A1 | 7/2016 | Hampapuram et al. | |
| 2016/0234020 A1 | 8/2016 | Nix | |
| 2017/0124272 A1 | 5/2017 | Reihman et al. | |
| 2018/0027106 A1 | 1/2018 | Mandapaka et al. | |
| 2018/0078777 A1 | 3/2018 | Wu et al. | |
| 2018/0088646 A1* | 3/2018 | Chen | H04W 4/80 |
| 2018/0184380 A1* | 6/2018 | Xue | H04W 4/80 |
| 2019/0036886 A1 | 1/2019 | Wu et al. | |
| 2019/0114393 A1 | 4/2019 | Andersen | |
| 2020/0128482 A1* | 4/2020 | Daoura | H04W 4/80 |
| 2020/0375455 A1* | 12/2020 | Van Tassel | A61B 5/14532 |
| 2020/0375457 A1 | 12/2020 | Van Tassel et al. | |

FOREIGN PATENT DOCUMENTS

| | | |
|---|---|---|
| EP | 2636426 A1 | 9/2013 |
| EP | 3 158 922 A1 | 4/2017 |
| EP | 3240352 A1 | 11/2017 |
| EP | 3 435 866 | 11/2020 |
| EP | 3 943 150 A1 | 1/2022 |
| EP | 3730045 | 3/2022 |
| EP | 3 797 685 | 5/2022 |
| JP | WO2015/194381 A1 | 12/2015 |
| WO | WO 97/18639 A1 | 5/1997 |
| WO | WO 99/58190 | 11/1999 |
| WO | WO 02/15778 | 2/2002 |
| WO | WO 03/026728 | 4/2003 |
| WO | WO 2004/006982 | 1/2004 |
| WO | WO 2005/018450 | 3/2005 |
| WO | WO 2005/046780 | 5/2005 |
| WO | WO 2006/040083 | 4/2006 |
| WO | WO 2006/094513 | 9/2006 |
| WO | WO 2006/121921 | 11/2006 |
| WO | WO 2007/002189 A2 | 1/2007 |
| WO | WO 2007/097754 | 8/2007 |
| WO | WO 2007/104755 A1 | 9/2007 |
| WO | WO 2008/065646 | 6/2008 |
| WO | WO 2008/073813 | 6/2008 |
| WO | WO 2008/114223 | 9/2008 |
| WO | WO 2008/115409 | 9/2008 |
| WO | WO 2008/144325 A1 | 11/2008 |
| WO | WO 2008/157821 | 12/2008 |
| WO | WO 2009/007287 | 1/2009 |
| WO | WO 2009/035773 | 3/2009 |
| WO | WO 2009/039013 | 3/2009 |
| WO | WO 2013/019225 A1 | 2/2013 |
| WO | WO 2013/044153 A1 | 3/2013 |
| WO | WO 2013/069894 A1 | 5/2013 |
| WO | WO 2013/090731 A1 | 6/2013 |
| WO | WO 2013/090791 A1 | 6/2013 |
| WO | WO 2014/011488 A2 | 1/2014 |
| WO | WO 2014/158405 A2 | 10/2014 |
| WO | WO 2014/165172 A1 | 10/2014 |
| WO | WO 2014/179343 A1 | 11/2014 |
| WO | WO 2015/069797 A1 | 5/2015 |
| WO | WO 2016/064184 A1 | 4/2016 |
| WO | WO 2016/092448 | 6/2016 |
| WO | WO 2016/092448 A1 | 6/2016 |
| WO | WO 2016/101774 A1 | 6/2016 |
| WO | WO 2016143973 A1 | 9/2016 |
| WO | WO 2017/172781 A1 | 10/2017 |
| WO | WO 2018/017484 A1 | 1/2018 |
| WO | WO 2018/075333 A2 | 4/2018 |
| WO | WO 2019126101 A1 | 6/2019 |

OTHER PUBLICATIONS

Exhibit B-22.pdf—Opponent's Written Response in Opposition of EP 3 730 045, Sep. 27, 2023, 43 pages.
McCartney et al., "In vivo glucose sensing for diabetes management: progress towards non-invasive monitoring," BMJ, vol. 319, 4 pages (1999).
Townsend et al., "Getting Started with Bluetooth Low Energy—Tools and Techniques for Low-Power Networking," O'Reilly Media, Inc., 180 pages (2014).
Wang et al. "A Feasible IMD Communication Protocol: Security without Obscurity," School of Engineering and Computing Sciences, NYIT Research Experience for Undergraduates (REU), May 26-Jul. 30, 2015, 1 page.
U.S. Appl. No. 16/934,592, filed Jul. 21, 2020.
U.S. Pat. No. 10,375,222, issued Aug. 6, 2019, 442 pages.
NFC Forum Bluetooth Special Interest Group, Bluetooth® Secure Simple Pairing Using NFC, 39 pages (2014).
Omre, "Bluetooth Low Energy: Wireless Connectivity for Medical Monitoring," Journal of Diabetes Science and Technology, vol. 4, No. 2, pp. 457-463 (2010).
Padgette, et al., "Guide to Bluetooth Security—Recommendations of the National Institute of Standards and Technology," National Institute of Standards and Technology, U.S. Dept. of Commerce, 800-121, Rev 1, 48 pages (May 2017).
Specification vol. 0, Specification of the Bluetooth System, Experience More, Master Table of Contents & Compliance Requirements, 134 pages (2010).
Specification vol. 0, Specification of the Bluetooth System, Wireless connections made easy, Master Table of Contents & Compliance Requirements, 92 pages (2003).
Strömmer, et al., "Application of Near Field Communication for Health Monitoring in Daily Life," Proceedings of the 28th IEEE, EMBS Annual International Conference, New York City, USA, Aug. 30-Sep. 3, 2006, pp. 3246-3249.
Zhang, et al., "Bluetooth Low Energy for Wearable Sensor-based Healthcare Systems", 2014 Health Innovations and Point-of-Care Technologies Conference, pp. 251-254 (2014).
European Search Report for related European Patent Application No. 21170259.2 dated Oct. 15, 2021 (5 pages).
"Blood glucose monitoring" retrieved from "https://web.archive.org/web/20111215063153/http://en.wikipedia.org/wiki/Blood_glucose_monitoring" on Aug. 1, 2021, 6 pages.
Bluetooth Specification, Encryption and Authentication Overview, vol. 6, Version 4.0, 1 page (2010).
Bluetooth Master/Salve Communications and Sniff/Sniff Sub-Rating Modes, White Paper (2008).
Cunningham et al., "In Vivo Glucose Sensing," Wiley & Sons (2010).

(56) References Cited

OTHER PUBLICATIONS

Cornelius, "Usable Security for Wireless Body-Area Networks," Dartmouth College PhD Dissertations. 42 (2013).
Decuir, "Bluetooth 4.0:Low Energy", Standards Architect, CSR Technology, Councilor, Bluetooth Architecture Review Board, IEEE Region 6 Northwest Area Chair, 104 pages (2012).
Dementyev et al., "Power Consumption Analysis of Bluetooth Low Energy, ZigBee and ANT Sensor Nodes in a Cyclic Sleep Scenario", IEEE International Wireless Symposium (IWS), 5 pages (2013).
Diallo et al., "A Secure Authentication Scheme for Bluetooth Connection," 5th International Conference on Computer & Communication Engineering, DOI 10.1109/ICCCE.2014.29, 60-63 (2014).
Ellmerer et al., "Measurement of interstitial albumin in human skeletal muscle and adipose tissue by open-flow microperfusion," Am. J. Physiol. Endocrinol. Metab., 278: E352-E356 (2000).
Finkenzeller, "RFID Handbook: Fundamentals and Applications in Contactless Smart Cards, Radio Frequency Identification and Near-Field Communication", Third Edition, 4 pages (2010).
German Infringement Complaint (2021) with English Abstract.
German Infringement Complaint Service addressed to Dexcom Deutschland GmbH (2021).
Gomez et al., "Overview and Evaluation of Bluetooth Low Energy: An Emerging Low-Power Wireless Technology," Sensors, 12, 11734-11753 (2012).
GRID.pdf, IEEE, 36 pages, May 2012.
Guder et al., "Samples: From the Patient to the Laboratory, The impact of preanalytical variables on the quality of laboratory results," Wiley-Vch GmbH & Co. KGaA (2003).
Higson et al., "Biosensors: a viable monitoring technology?" Med. & Biol. Eng. & Comput., 32, 601-609 (1994).
Klonoff, "A Review of Continuous Glucose Monitoring Technology", Diabetes Technology & Therapeutics, 7(5):770-775 (2005).
Klonoff, "Continuous Glucose Monitoring: Roadmap for 21st century diabetes therapy", Diabetes Care, 28(5):1231-1239 (2005).
Mohanty et al., Biosensors: A tutorial review, IEEE Potentials, 35-40 (2006).
Morak et al., "Design and Evaluation of a Telemonitoring Concept Based on NFC-Enabled Mobile Phones and Sensor Devices", IEEE Transactions on Information Technology in Biomedicine, 16(1):17-23 (2012).
Movassaghi et al., "Wireless Technologies for Body Area Networks: Characteristics and Challenges", IEEE, International Symposium on Communications and Information Technologies (ISCIT), 42-47 (2012).
Near filed communication—Wikipedia, the free encyclopedia, 14 pages (2014).
Near Field Communication (NFC) Technology and Measurements, White Paper, Rohde & Schwarz, 18 pages (2011).
Near Field Communication (NFC) Technology and Measurements, White Paper, Rohde & Schwarz, 1 page (2011).
Padgette et al., "Guide to Bluetooth Security, Recommendations of the National Institute of Standards and Technology," NIST, U.S. Dept. of Commerce, Special Publication 800-121 Revision 1 (2012).
Rivest et al., "A Method for Obtaining Digital Signatures and Public-Key Cryptosystems," MIT, 15 pages (1977).
Schaupp et al., "Direct access to interstitial fluid in adipose tissue in humans by use of open-flow microperfusion," E401-E408, Downloaded from journals.physiology.org/journal/ajpendo (092.040.147.197) on Oct. 4, 2021.
Seymour et al., Bluetooth Master/Slave Communications and Sniff/Sniff Sub-rating Modes White Paper, Aug. 14, 2008.
Sola-Gazagnes et al., "Emergent technologies applied to diabetes: What do we need to integrate continuous glucose monitoring into daily practice? Where the long-term use of continuous glucose monitoring stands in 2011", Diabetes & Metabolism, vol. 37, pp. S65-S70 (2011).
Specification of the Bluetooth System, Experience More, Specification vol. 0, Covered Core Package Version: 4.0, 2302 pages (2010).
Specification of the Bluetooth System, Experience More, Specification vol. 0, Covered Core Package Version: 4.0, 89 pages (2010).
Specification of the Bluetooth System, Master Table of Contents & Compliance Requirements, Version 4.1 (2013).
Specification of the Bluetooth System, Master Table of Contents & Compliance Requirements, Version 4.2 (2014).
Stallings, "Cryptography and Network Security, Principles and Practice," 5th Ed., Prentice Hall (2011).
Strickland et al., "Continuous Glucose Monitoring Profile Bluetooth® Profile Specification," Interest Group, v1.0.1 (2015).
The New Shorter Oxford English Dictionary, p. 50 date unknown.
Townsend et al., "Getting Started with Bluetooth Low Energy," O'Reilly, 26 pages (2014).
Wikipedia, "Analyte" retrieved from https://en.wikipedia.org/w/index.php?title=Analyte&oldid=527866671 (2012).
Wikipedia, "Bluetooth", 25 pages retrieved from https://en.wikipedia.org/wiki/Bluetooth (2022).
Wikipedia, Bluetooth Low Energy, 11 pages retrieved from https://en.wikipedia.org/wiki/Bluetooth_Low_Energy (2022).
Wikipedia, Challenge-response authentication retrieved from https://en.wikipedia.org/wiki/Challenge%E2%80%93response_authentication (2013).
Wikipedia, Digital Signature, 10 pages retrieved from https://en.wikipedia.org/wiki/Digital_signature (2021).
Wikipedia, Digital Signature, 10 pages (2012).
Wikipedia, "In vivo" retrieved from https://en.wikipedia.org/w/index.php?title=In_vivo&oldid=524960105 (2012).
Wikipedia, "Near-field communication" retrieved from https://en.wikipedia.org/w/index.php?title=Near-field_communication&oldid=525308529 (2012).
Wikipedia, RSA (cryptosystem), 17 pages retrieved from https://en.wikipedia.org/wiki/RSA_(cryptosystem) (2021).
International Search Report mailed Aug. 5, 2022 in International Application No. PCT/US2022/028748.
Declaration of Dr. Sayfe Kiael, Ph.D., Inter Partes Review of U.S. Pat. No. 10,375,222, 100 pages (2024).
Diallo et al., "A Secure Authentication Scheme for Bluetooth Connection," 5th International Conference on Computer & Communication Engineering, 60-63 (2014).
File History of U.S. Pat. No. 10,375,222 issued Aug. 6, 2019, Parts 1-2 (422 pages).
Omre, "Bluetooth Low Energy: Wireless Connectivity for Medical Monitoring," Journal of Diabetes Sci Technol, vol. 4, Issue 2, 457-463, Mar. 2010.
Padgette et al., "Guide to Bluetooth Security, Recommendations of the National Institute of Standards and Technology," NET Special Publication 800421 Revision National Institute of Standards and Technology, U.S. Department of Commerce, 48 pages (2012).
Specification of the Bluetooth System Master Table of Contents & Compliance Requirements Covered Core Package version: 1.2, Current Master TOC issued: Nov. 5, 2003, 92 pages.
Specification of the Bluetooth System Experience More Master Table of Contents & Compliance Requirements Covered Core Package version: 4.0, Current Master TOC issued: Jun. 30, 2010, 134 pages.
Strömmer et al., "Application of Near Field Communication for Health Monitoring in Daily Life," Proceedings of the 28th IEEE FrC09., EMBS Annual International Conference, 3246-3249, Aug. 30-Sep. 3, 2006.
Townsend et al., "Getting Started with Bluetooth Low Energy," O'Reilly Media, 1-164, 180 pages (2014).
Wang et al., "A Feasible IMD Communication Protocol: Security without Obscurity," NYiT School of Engineering and Computing Sciences, 1 page (2015).
Zhang et al., "Bluetooth Low Energy for Wearable Sensor-based Healthcare Systems," 2014 Health Innovations and Point-of-Care Technologies Conference, 251-254 (2014).
Bluetooth Specification, Version 4.0, 2,303 pages (2010).
Compare Specification—Apple iphone 6 vs. Apple iphone 6 Plus—https://www.gsmarena.com/compare.php3?idPhone1=6378&idPhone2-6665, 2 pages, Jan. 31, 2022.
Dexcom G4® Platinum, Continuous Glucose Monitoring System, User's Guide, Dexcom, Inc., 161 pages (2015).

(56) References Cited

OTHER PUBLICATIONS

Dexcom G5 User Guide, Dexcom, Inc., 265 pages (2015).
Dexcom G5™ Mobile, Continuous Glucose Monitoring System, User Guide, Dexcom, Inc., 264 pages (2015).
Dexcom News Releases—FDA Approves Dexcom G4 Platinum Continuous Glucose Monitoring System with Share—https:/www.dexcom.com/en-us/news/fda-approves-dexcom-g4-platinum-continuous-glucose-monitoring-system-share, Dexcom, Inc., 2 pages, Jan. 26, 2015.
Dexcom Press Release—FDA Approves Dexcom G5® Mobile Continuous Glucose Monitoring System—https://www.dexcom.com/news/1257506247-fda-approves-dexcom-g5®-mobile-continuous-glucose-monitoring-system, Dexcom, Inc., 4 pages, Aug. 24, 2015.
Encyclopedia Britannica, Science & Tech, Bluetooth Definition, 5 pages, (Oct. 14, 2023).
Excerpts from the "German Health Report Diabetes 2023" of the German Diabetes Society, 14 pages (2022) (with an English Abstract).
Ferro, et al., "Bluetooth and Wi-fi Wireless Protocols: A Survey and a Comparison", IEEE Wireless Communications, pp. 1-24 (2004).
Ferro, et al., "Bluetooth and Wi-fi Wireless Protocols: A Survey and a Comparison", IEEE Wireless Communications, 12(1):12-26 (2005).
FreeStyle Libre Flash Glucose Monitoring System, User's Manual, Abbott Diabetes Care Ltd., 124 pages (2014).
Hamblen, "A short history of NFC: Where Near Field Communication has come from.", 2 pages, Dec. 19, 2012.
Klueh, et al., "Inflammation and Glucose Sensors: Use of Dexamethasone to Extend Glucose Sensor Function and Life Span in Vivo", Journal of Diabetes Science and Technology, 1(4):496-504 (2007).
Press Coverage of FreeStyle Libre launch, Antonia Giese, retrieved from https://www.bild.de/ratgeber/gesundheit/diabetes/hightech-zucker-sensor-diabetes-test-freestyle-libre-flash-37732134.bild.html, 8 pages Sep. 20, 2014 (with an English Translation).
Specification of the Bluetooth System, Experience More, Specification vol. 0, Covered Core Package Version: 4.0, 41 pages (2010).
Specification of the Samsung Galaxy Alpha, Samsung Newsroom Deutschland—http://www.samsung.de/galaxyalpha. 7 pages, Aug. 13, 2014 (with an English Abstract).
Wikipedia, The Free Encyclopedia, "Continuous glucose monitor", retrieved from https://en.wikipedia.org/w/index.php?title=Continuous_glucose_monitor&oldid=1180606331, 10 pages (Oct. 1, 2023).
Wikipedia, The Free Encyclopedia, "Radio-frequency identification", retrieved from https://en.wikipedia.org/wiki/Radio-frequency_identification, 30 pages (Oct. 23, 2023).
U.S. Appl. No. 60/587,787, filed Jul. 13, 2004, Brister, et al.
"Within Definition & Meaning" retrieved from "https://www.dictionary.com/browse/within" on Sep. 9, 2022, 5 pages.
U.S. Appl. No. 60/587,787, filed Jul. 13, 2004, 69 pages.
U.S. Appl. No. 60/614,683, filed Sep. 30, 2004, Brister, et al.
"Setting Your Sensor Settings" retrieved from "https://web.archive.org/web/20160803065621/http://www.medtronicdiabetes.com:80/customer-support/device-settings-and-features/sensor-settings/setting-sensor-settings" on Nov. 18, 2022, 5 pages.
Dexcom G5 Mobile Continuous Glucose Monitoring System, Advisory Committee Briefing Materials, Clinical Chemistry and Clinical Toxicology Devices Panel, 283 pages (2016).
Dowla, "The Basics of Radio Frequency Identification (RFID) Technology", Handbook of RF & Wireless Technologies, Chapter 14, 44 pages (2004).
Evans, et al., "Clinical temperature acquisition using proximity telemetry", J. Biomed. Eng., 13:83-86 (1991).
Finkenzeller, "RFID Handbook: Fundamentals and Applications in Contactless Smart Cards and Identification", Second Edition, 114 pages (2003).
Heller, et al., "Electrochemical Glucose Sensors and Their Applications in Diabetes Management", Chemical Reviews, 108(7):2482-2505 (2008).
Lee, "RFID Coil Design", Microchip Technology Inc., DS00678B, pp. 1-19 (1998).
Liang, et al., "An implantable bi-directional wireless transmission system for transcutaneous biological signal recording", Physiological Measurement, 26:83-97 (2005).
Radio Frequency Identification RFID, Aim Inc., White Paper, Document Version 1.2, 17 pages (2001).
Sorrells, "Passive RFID Basics", Microchip Technology Inc., DS00680B, pp. 1-5 (1998).
Morak et al., "Design and Evaluation of a Telemonitoring Concept Based on NFC-Enabled Mobile Phones and Sensor Devices," IEEE Transactions on Information Technology in Biomedicine, Nov. 2011, 8 pgs.
Padgette et al., "Guide to Bluetooth Security. Recommendations of the National Institute of Standards and Technology," NIST Special Publication 800-121, Revision 1, Jun. 2012, 47 pgs.
A Dictionary of Computer Science for "authentication", Seventh Edition, Oxford University Press, 3 pages (2016).
BBC News, Technology, Bluetooth rival unveiled by Nokia, 2 pgs. (Oct. 4, 2006).
Bloodborne pathogens, Occupational Safety and Health Admin., Labor, 29 CFR Ch. XVII (Jul. 1, 2003 Edition) § 1910.1030, pp. 260-273 date unknown.
Bluetooth Specification V 2.1, Jul. 26, 2007, pp. 1-541.
Bluetooth Specification V 2.1, Jul. 26, 2007, pp. 542-906.
Burr, et al., Electronic Authentication Guideline, NIST Special Publication 800-63-2, Computer Security, NIST National Institute of Standards and Technology, U.S. Department of Commerce, 123 pages (2013).
Dexcom STS 7 Plus User's Guide, 2011, 144 pgs.
Dexcom STS 7 User Guide, 2007, 74 pgs.
Diglas et al., "Reduced pain perception with Pen Mate™ an automatic needle insertion device for use with an insulin pen," Practical Diabetes Int 16(2):39-41 (1999).
Expert Statement of Professor Pantelis Georgiou, Aug. 9, 2024, 52 pgs.
Freestyle Navigator User Guide, 2008, 195 pgs.
Guardian Real Time User Guide, 2006, 181 pgs.
Hirsch, "Realistic Expectations and Practical Use of Continuous Glucose Monitoring for the Endocrinologist," J Clin Endocrinol Metab 94:2232-2238 (2009).
Hughes, "The Business of Self-Monitoring of Blood Glucose: A Market Profile," Journal of Diabetes Science and Technology, 3(5):1219-1223 (2009).
IEEE 100, The Authoritative Dictionary of IEEE Standards Terms for "authentication", Seventh Edition, Standards Information Network IEEE Press, 3 pages (2000).
Moore, "The Potential Use of Radio Frequency Identification Devices for Active Monitoring of Blood Glucose Levels," Journal of Diabetes Science and Technology 3(1):180-183 (2009).
Newton's Telecom Dictionary for "authenticate", 30th Updated, Expanded, Anniversary Edition, Harry Newton, 4 pages (2016).
Expert Statement of Andrew Varde, Aug. 9, 2024, 87 pgs.
Feature-by-Feature comparison of claims 1 and 5 of EP921 in relation to D2 and D3, Nov. 12, 2024, 7 pgs.
UPC Annex A34-Second Expert Opinion of Dr. Michael Schoemaker, Exhibits MS-5 to MS-8, Nov. 8, 2024 (43 pgs.).
UPC Exhibit MS-5 to Second Expert Opinion of Dr. Michael Schoemaker, Nov. 8, 2024 (9 pgs.).
UPC Exhibit MS-6 to Second Expert Opinion of Dr. Michael Shoemaker, Nov. 8, 2024, Part 1 (63 pgs.).
UPC Exhibit MS-6 to Second Expert Opinion of Dr. Michael Shoemaker, Nov. 8, 2024, Part 2 (63 pgs.).
UPC Exhibit MS-7 to Second Expert Opinion of Dr. Michael Shoemaker, Nov. 8, 2024 (44 pgs.).
UPC Exhibit MS-8 to Second Expert Opinion of Dr. Michael Shoemaker, Nov. 8, 2024 (25 pgs.).

* cited by examiner

600

610

620

TRANSMITTING ANALYTE DATA USING LOW-POWER INSTRUCTION SETS

PRIORITY

This application is a continuation-in-part under 35 U.S.C. § 120 of U.S. patent application Ser. No. 16/934,592, filed 21 Jul. 2020, which is incorporated herein by reference. This application claims the benefit, under 35 U.S.C. § 119(e), of U.S. Provisional Patent Application No. 63/252,120, filed 4 Oct. 2021, and U.S. Provisional Patent Application No. 63/292,953, filed 22 Dec. 2021, which are incorporated herein by reference.

BACKGROUND

Field of the Disclosed Subject Matter

The disclosed subject matter relates to a system for transmitting data between an analyte sensor and one or more receiving devices in an external environment of the analyte sensor.

Description of Related Art

Certain analyte sensor devices can wirelessly transmit data to, and receive data from, other computing devices. While some of these analyte sensor devices are equipped with powerful processors and operate using a permanent power supply, other analyte sensor devices are designed to operate efficiently, using little power. Low-power analyte sensor devices can also have less computational capabilities or resources than the devices with which these analyte sensor devices are communicating. The low-power analyte sensor devices can rely on more powerful devices to perform more complex processing of the data the low-power analyte sensor devices are collecting. In some cases, these low-power analyte sensor devices have restricted communication abilities as well, typically limited to short-range communication with devices that are within the same room. To offload data to another device, the low-power analyte sensor device can establish a communication session with the other device and transmit, for example, collected analyte data for analysis. However, to ensure real-time processing of data, such that the most relevant data is available to a user of the low-power analyte sensor device, some low-power analyte sensor devices must maintain the communication session for data processing to be performed. The communication session can still use the short-range communication. If the low-power analyte sensor device or other device are moved out of range, the communication session can terminate, and data can be left unprocessed. In addition to inconveniencing the users of the low-power analyte sensor device, maintaining a communication session with another analyte sensor device can drain the battery of the low-power analyte sensor device, reducing the operational lifetime of the device.

In other low-power analyte sensor devices, communication sessions are not constantly maintained. Instead, these low-power analyte sensor devices can establish a communication session when there is a backlog of historical data that has yet to be offloaded to a more powerful device. To conserve battery life, once the data has been uploaded, the communication session ends. After collecting more data, the low-power analyte sensor device can periodically check whether one or more appropriate receiving devices are within range to reestablish a communication session, or can rely on the user to request such data using the receiving device. If a receiving device is in range, the low-power analyte sensor device establishes a new communication session to upload the additional data. If the receiving device is out of range or otherwise unavailable while the low-power analyte sensor device is looking for it, the data cannot be uploaded. Moreover, once the receiving device returns within range of the analyte sensor device, the receiving device and analyte sensor device re-establish a communication session, which can take additional time before additional data can be transferred such that the latest analyte data may not be immediately available to the user.

Accordingly, there is an opportunity for methods and systems that can be implemented by low-power, and low-cost, analyte sensor devices to efficiently provide current or high priority analyte data to other devices for processing and output.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the drawings.

To achieve these and other advantages and in accordance with the purpose of the disclosed subject matter, as embodied and broadly described, the disclosed subject matter includes systems and methods for expedited delivery of high-priority data from an analyte sensor to one or more receiving devices by repurposing reserved communication channels. Exemplary systems and methods can include a method for monitoring a subject using an analyte monitoring device. One or more processors of the analyte monitoring device generate sensor data indicative of an analyte level measured by an analyte sensor. At least a portion of the analyte sensor can be transcutaneously positioned in contact with a bodily fluid of the subject. The one or more processors of the analyte monitoring device can identify a subset of the sensor data based on a priority level associated with the sensor data. The one or more processors of the analyte monitoring device can prepare a data packet that includes the identified subset of the sensor data and connection data associated with establishing a communication session with the analyte monitoring device. The one or more processors of the analyte monitoring device can cause a transceiver of the analyte monitoring device to transmit the data packet to one or more user devices within a communication range of the transceiver. The one or more processors of the analyte monitoring device can receive, through the transceiver and from a first user device of the one or more user devices, an acknowledgement signal indicating receipt of the sensor data. In particular embodiments, the data packet further includes identification data for the first user device for directing the data packet to the first user device. In particular embodiments, prior to causing the transceiver of the analyte monitoring device to transmit the data packet, the one or more processors of the analyte monitoring device can receive an activation command from the first user device. In particular embodiments, the one or more processors of the analyte monitoring device can cause the transceiver to transmit the data packet by identifying one or more communication channels that are associated, by a specified communication protocol, with establishing connections between devices and generating a signal based on the data packet using the one or more identified communication channels. In particular embodiments, after receiving the acknowledgement signal from the first user device, the one or more processors of the analyte monitoring device can establish the communication session with the first user device using the transceiver. The one or more processors of the analyte monitoring device can cause the transceiver to transmit a second subset of the sensor data to the first user device through the communication session. The second subset of the sensor data was not included in the data packet. In particular embodiments, the one or more processors of the analyte monitoring device can encrypt the identified subset of the sensor data using an encryption key shared between the analyte monitoring device and the first user device. In particular embodiments, the encryption key can be dynamically determined or identified using a key-rotation scheme. In particular embodiments, the priority level associated with the sensor data can be based on a time elapsed since the sensor data was collected. The sensor data with a highest priority level can be the most recently collected. In particular embodiments, the priority level associated with the sensor data is based on a condition of the subject determined from the sensor data. In particular embodiments, the one or more processors of the analyte monitoring device prepares connection data associated with establishing the communication session with the analyte monitoring device based on a periodically occurring window of time. In particular embodiments, the analyte can be, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. In particular embodiments, the data packet further includes a temperature, heart rate, blood pressure, or movement data of the subject.

According to other aspects of the disclosed subject matter, systems and methods can include a method for monitoring analyte levels of a subject using a user device. One or more processors of the user device can send, using a communication module of the user device, an activation command to an analyte monitoring device associated with the subject. The one or more processors of the user device can receive, using the communication module and during a first communication session with the analyte monitoring device, a first set of sensor data from the analyte monitoring device. The first set of sensor data can be indicative of a first analyte level measured by the analyte monitoring device at a first time. The one or more processors of the user device can close the first communication session. The one or more processors of the user device can receive, using the communication module, a data packet from the analyte monitoring device. The data packet can include connection data associated with establishing a second communication session with the analyte monitoring device. The data packet can include a second set of sensor data from the analyte monitoring device indicative of a second analyte level measured by the analyte monitoring device at a second time. The one or more processors of the user device can output the second set of sensor data in an interface of the user device. In particular embodiments, outputting the second set of sensor data include causing, by the one or more processors of the user device, the interface of the user device to indicate that the second set of sensor data corresponds to a current or most recently determined analyte level measured by the analyte monitoring device. In particular embodiments, the one or more processors of the user device can output an alarm based on the second set of sensor data. In particular embodiments, the one or more processors of the user device can send, using the communication module, an acknowledgement signal to the analyte monitoring device. The acknowledgement signal can indicate that the second set of sensor data has been received. In particular embodiments, the one or more processors of the user device can establish the second communication session with the analyte monitoring device based on the connection data of the data packet. The one or more processors of the user device can receive a third set of sensor data indicative of a third analyte level measured by the analyte monitoring device during a period of time between the first time and the second time. In particular embodiments, the second set of sensor data is included in an encrypted data payload of the data packet. The one or more processors of the user device can decrypt the encrypted data payload of the data packet using an encryption key shared between the analyte monitoring device and the user device and extract the second set of sensor data from the decrypted data payload. In particular embodiments, the user device is associated with a user who has been approved by the subject to receive the sensor data on behalf of the subject.

According to other aspects of the disclosed subject matter, systems and method can include an analyte monitoring device that includes one or more processors, an analyte sensor, a communication module, and one or more memories communicatively coupled to the one or more processors, the analyte sensor, and the communication module. The one or more processors can be configured to generate sensor data indicative of an analyte level measured by the analyte sensor. At least a portion of the analyte sensor is transcutaneously positioned in contact with a bodily fluid of the subject. The one or more processors can be configured to store the sensor data in the one or more memories. The one or more processors can identify, from the one or more memories, a first subset of the sensor data corresponding to a first time. The one or more processors can prepare a data packet including the identified subset of the sensor data and connection data associated with establishing a communication session with the analyte monitoring device. The one or more processors can cause the communication module to transmit the data packet to one or more user devices within a communication range of the communication module. The one or more processors can receive, through the communication module, a communication session request from a first user device of the one or more user devices. The one or more processors can cause the communication module to transmit a second data packet to the first user device, the second data packet including a second subset of the data corresponding to a second time.

To further advantages and in accordance with the purpose of the disclosed subject matter, as embodied and broadly described, the disclosed subject matter further includes systems and methods for establishing, maintaining, and transmitting data to multiple receiving devices using concurrent communication sessions. Exemplary systems and methods can include an analyte monitoring device for monitoring a subject using an analyte monitoring device. The analyte monitoring device can include one or more processors, an analyte sensor, a communication module, and one or more memories communicatively coupled to the one or more processors, the analyte sensor, and the communication module. The one or more memories include instructions executable by the one or more processors to configure the one or more processors to perform operations in accordance with the techniques disclose herein. One or more processors of the analyte monitoring device generate sensor data indicative of an analyte level measured by an analyte sensor of the analyte monitoring device. At least a portion of the analyte sensor is transcutaneously positioned in contact with a bodily fluid of the subject. The one or more processors of the analyte monitoring device receive a first request for the sensor data from a first device and a second request for the sensor data from a second device. The one or more processors of the analyte monitoring device select a first subset of the sensor data responsive to the first request. The one or more processors of the analyte monitoring device select a second subset of the sensor data responsive to the second request. The one or more processors of the analyte monitoring device prepare a first data packet including the first subset of the sensor data and a second data packet including the second subset of the sensor data. The one or more processors of the analyte monitoring device cause the communication module of the analyte monitoring device to transmit the first data packet to the first device. The one or more processors of the analyte monitoring device cause the communication module of the analyte monitoring device to transmit the second data packet to the second device.

In particular embodiments, prior to causing the communication module of the analyte monitoring device to transmit the second data packet to the second device, the one or more processors of the analyte monitoring device receive, through the communication module and from the first device, an acknowledgement signal indicating receipt of the first subset of the sensor data. In particular embodiments, the first request and the second request include criteria for selecting the first subset of the sensor data and the second subset of the sensor data, respectively. In particular embodiments, the one or more processors of the analyte monitoring device select the first subset of the sensor data or the second subset of the sensor data based on a priority level associated with the sensor data. In particular embodiments, the one or more processors of the analyte monitoring device cause the communication module to transmit the first data packet to the first device before causing the communication module to transmit the second data packet to the second device based on the analyte monitoring device receiving the first request for the sensor data before receiving the second request for the second data. In particular embodiments, the first device or the second device is a fitness monitor or fitness device. In particular embodiments, the first device or the second device includes medical components for use by the subject based on the first subset of the sensor data or the second subset of the sensor data. In particular embodiments, the first device or the second device includes networking components to transmit the first subset of the sensor data or the second subset of the sensor data to one or more remote devices. In particular embodiments, the first device is a smartphone and the second device is a smartwatch.

In particular embodiments, the one or more processors of the analyte monitoring device establish, a communication session with the second device through communication with the first device by: receiving, from the first device and via the communication module, a connection request including identification information for the second device and information to facilitate a communication session with the second device, where the identification information was received by the first device from the second device during a communication session between the first device and the second device; transmitting an acknowledgement of the connection request to the second device using the information to facilitate the communication session with the second device; and performing a mutual authentication with the second device to generate a shared encryption key for subsequent communication sessions. In particular embodiments, the first request for the sensor data includes an identifier for the first device. The identifier is an index in a mapping table stored by the analyte monitoring device. The one or more processors of the analyte monitoring device identify the first device based on querying the mapping table using the index from the first request. In particular embodiments, the one or more processors of the analyte monitoring device encrypt the first subset of the sensor data using a first encryption key shared between the analyte monitoring device and the first device and encrypt the second subset of the sensor data using a second encryption key shared between the analyte monitoring device and the second device. In particular embodiments, the first encryption key and second encryption key are dynamically determined or identified using a key-rotation scheme. In particular embodiments, the analyte includes glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, or uric acid.

An analyte sensor can exchange data with other devices, referred to as receivers, controlled by users. The receivers can use commercial operating systems that communicate through wireless bi-directional communication links with the analyte sensor. As one example, mobile devices with Bluetooth Low Energy (BLE) circuitry are available for communication with certain analyte sensors. The bi-directional communication links can be formed using a wireless communication protocol that includes connection requests or advertisement notices received by the receivers. The advertisement notices are broadcast by the analyte device at predetermined constant frequencies. The use of the advertising notices to facilitate the establishment of wireless communications involves a significant power consumption for the analyte sensor.

During a typical advertising operation, an analyte sensor configured to operate with a short-range wireless communication protocol such as BLE, transmits advertisement notices and searches for scan requests from receivers. In some cases, the analyte sensor is in a sleep state, in which the analyte sensor consumes relatively little power, when it is time to perform an advertising operation. The analyte sensor wakes up from the sleep state before the analyte sensor is able to transmit an advertisement notice and searches for a scan request. Each time the analyte sensor awakes from the sleep state, the analyte sensor performs a predetermined set of startup and initialization actions or tasks. The analyte sensor utilizes a certain amount of power to perform all of the startup and initialization tasks associated with waking up. Over the lifetime of an analyte sensor, the analyte sensor will go to sleep and awake from the sleep state a substantially large number of times (e.g., several times each hour). Consequently, the actions and tasks that are performed during every wake-up operation, even if just to perform an advertising operation, utilize a relatively large amount of power over the life of the device.

According to other aspects of the disclosed subject matter, an analyte sensor can include a communication module with communication circuitry configured to wirelessly communicate with at least one other device, such as a receiver. The communication circuitry can be configured to transition between a sleep state, a partial awake state and a fully awake state. When in the fully awake state, the communication circuitry can be configured to execute tasks and actions associated with a communications protocol startup (CPS) instruction set that includes an advertisement scanning related (ASR) instruction subset and a non-ASR instruction subset. When in the partially awake state, the communication circuitry can be configured to execute functions, such as the ASR instruction subset. The partially awake state can be implemented as a limited-functionality branch of a programming and hardware stack directed to operating certain aspects of a communication protocol. The functions can include to prepare and transmit advertising notices, which can include payloads configured with specialized information as discussed herein, over one or more channels according to a wireless communications protocol and to scan the one or more channels for a connection request from another device. When a connection request is not received, the communication circuitry can return to the sleep state without performing actions or tasks associated with the non-ASR instruction subset of the CPS instruction set. Therefore, by implementing the partially awake state and only performing actions or tasks associated with the non-ASR instruction subset when a connection request is received, the total and average power consumption of the communication circuitry is reduced when the most common operation is to wake and send advertisement notices.

According to other aspects of the disclosed subject matter, an analyte monitoring device can include one or more processors, an analyte sensor, a communication module, and one or more memories communicatively coupled to the one or more processors, the analyte sensor, and the communication module. The one or more processors can be configured to generate sensor data indicative of an analyte level measured by the analyte sensor. At least a portion of the analyte sensor is transcutaneously positioned in contact with a bodily fluid of the subject. The one or more processors can be configured to initialize the communication module using an advertisement scanning related instruction set. The advertisement scanning related instruction set is a subset of a communications protocol startup instruction set including the advertisement scanning related instruction set and a non-advertisement scanning related instruction set. The one or more processors can cause the communication module to issue one or more advertising packets and receive a connection request from a receiving device. The one or more processors can complete initialization of the communication module using the non-advertisement scanning related instruction set. The one or more processors can select a subset of the sensor data, prepare a data packet comprising the subset of the sensor data, and cause the communication module to transmit the data packet to the receiving device.

In particular embodiments the communication module can be initialized responsive to the detection of expiration of a wakeup timer. In particular embodiments, initializing the communication module includes transitioning the communication module from a sleep state to an active state. In particular embodiments, after causing the communication module to issue the one or more advertising packets, the one or more processors are further configured to determine that the connection request has not been received from the receiving device for a period of time, transition the communication module from the awake state to the sleep state, and initialize the communication module using an advertisement scanning related instruction set a second time, wherein the connection request is received from the receiving device after the communication module has been initialized the second time. In particular embodiments, the communication module is transitioned from the awake state to the sleep state without executing the non-advertisement scanning related instruction set. In particular embodiments, the non-advertisement scanning related instruction set includes instructions related to initialization of a random access memory segment or block, initialization of sensing hardware; or initialization of an operating system service. In particular embodiments, the advertisement scanning related instruction set includes instructions related to detecting expiration of a wake-up timer, processor startup, initialization of a transmit circuit, formation of advertising data packets, transmission of advertising data packets, scanning one or more channels for a connection request from the receiving device, or validating or denying an incoming connection request. In particular embodiments, the connection request includes criteria for selecting the subset of the sensor data. In particular embodiments, the one or more processors are further configured to select the subset of the sensor data based on a priority level associated with the sensor data.

In another aspect, a computer implemented method is provided. Under control of one or more processors of an analyte sensor, where the one or more processors are configured with specific executable instructions, the method can include collecting signals related to detected analyte levels, and implementing program instructions to analyze the signals and/or manage storage of the signals and/or deliver a therapy. The method can also include communicating wirelessly with at least one other device and executing tasks and actions associated with a communications protocol startup (CPS) instruction set that includes an advertisement scanning related (ASR) instruction subset and a non-ASR instruction subset when in the fully awake state. When in a partially awake state, the method can include executing functions such as the ASR instruction subset. The functions can include transmitting advertising notices over one or more channels according to a wireless communications protocol, scanning the one or more channels for a connection request from another device (e.g., a suitably-configured receiver), and returning to a sleep state, without performing actions or tasks associated with the non-ASR instruction subset of the CPS instruction set when a connection request is not received.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the methods and systems of the disclosed subject matter. Together with the description, the drawings explain the principles of the disclosed subject matter.

BRIEF DESCRIPTION OF THE DRAWINGS

The details of the subject matter set forth herein, both as to its structure and operation, may be apparent by study of the accompanying figures, in which like reference numerals refer to like parts.

DETAILED DESCRIPTION OF EXAMPLE EMBODIMENTS

Figure 1:
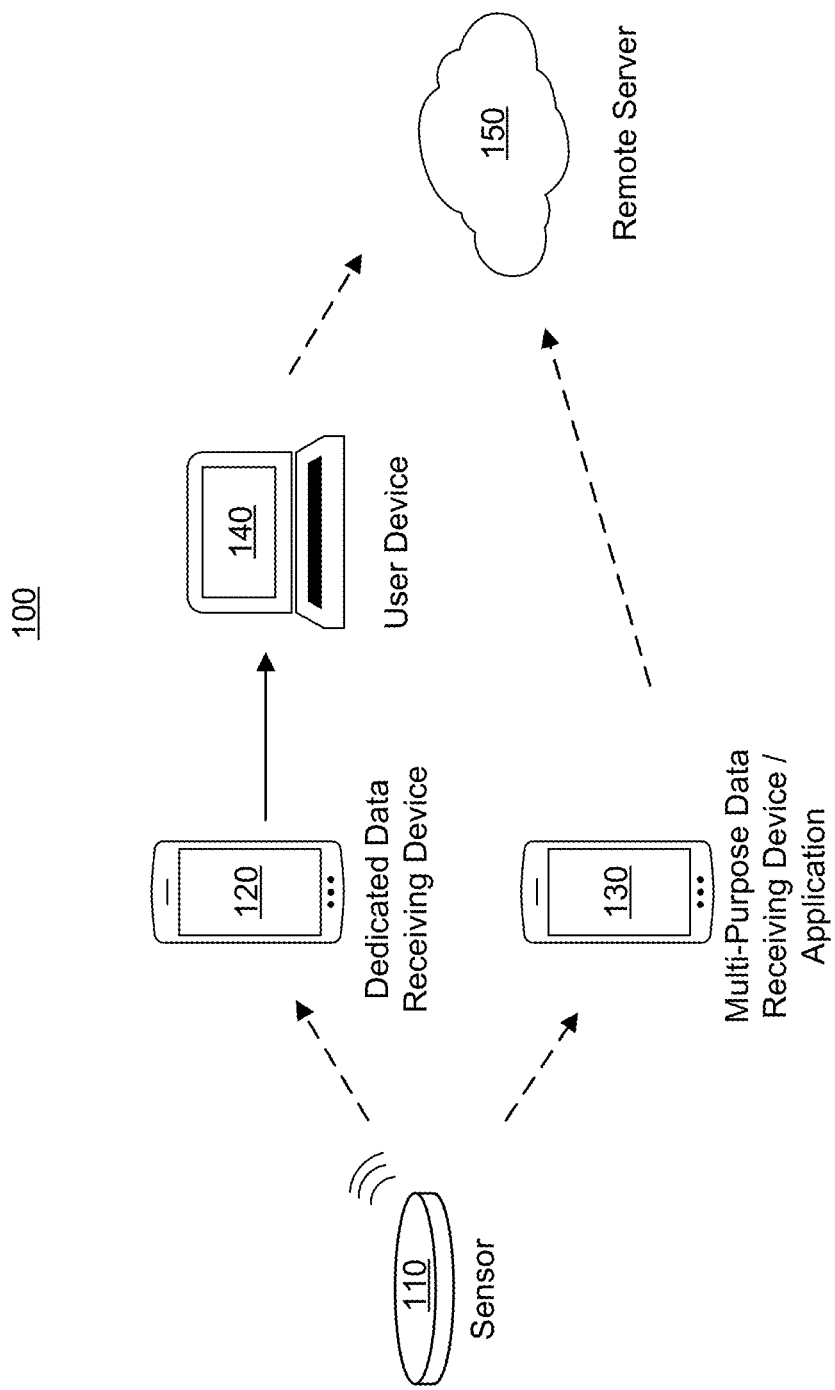
FIG. 1 is a diagram illustrating an operating environment of an example analyte monitoring system for use with the techniques described herein.

Reference will now be made in detail to the various exemplary embodiments of the disclosed subject matter, exemplary embodiments of which are illustrated in the accompanying drawings. The structure and corresponding method of operation of the disclosed subject matter will be described in conjunction with the detailed description of the system The systems and methods presented herein can be used for operations of a sensor used in an analyte monitoring system, such as but not limited to wellness, fitness, dietary, research, information or any purposes involving analyte sensing over time. As used herein, "analyte sensor" or "sensor" can refer to any device capable of receiving sensor information from a user, including for purpose of illustration but not limited to, body temperature sensors, blood pressure sensors, pulse or heart-rate sensors, glucose level sensors, analyte sensors, physical activity sensors, body movement sensors, or any other sensors for collecting physical or biological information. Analytes measured by the analyte sensors can include, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. The purpose and advantages of the disclosed subject matter will be set forth and apparent from the description that follows. Additional advantages of the disclosed subject matter will be realized and attained by the methods, apparatus, and devices particularly pointed out in the written description and claims thereof, as well as from the appended drawings.

For purpose of illustration and not limitation, this disclosure includes methods for expedited delivery of high-priority data from an analyte sensor to one or more receiving devices by repurposing reserved communication channels in accordance with the disclosed subject matter. Exemplary systems and methods can include a method for monitoring a subject using an analyte monitoring device. One or more processors of the analyte monitoring device generate sensor data indicative of an analyte level measured by an analyte sensor. At least a portion of the analyte sensor can be transcutaneously positioned in contact with a bodily fluid of the subject. The one or more processors of the analyte monitoring device can identify a subset of the sensor data based on a priority level associated with the sensor data. The one or more processors of the analyte monitoring device can prepare a data packet that includes the identified subset of the sensor data and connection data associated with establishing a communication session with the analyte monitoring device. The one or more processors of the analyte monitoring device can cause a transceiver of the analyte monitoring device to transmit the data packet to one or more user devices within a communication range of the transceiver. The one or more processors of the analyte monitoring device can receive, through the transceiver and from a first user device of the one or more user devices, an acknowledgement signal indicating receipt of the sensor data. In particular embodiments, the data packet further includes identification data for the first user device for directing the data packet to the first user device. In particular embodiments, prior to causing the transceiver of the analyte monitoring device to transmit the data packet, the one or more processors of the analyte monitoring device can receive an activation command from the first user device. In particular embodiments, the one or more processors of the analyte monitoring device can cause the transceiver to transmit the data packet by identifying one or more communication channels that are associated, by a specified communication protocol, with establishing connections between devices and generating a signal based on the data packet using the one or more identified communication channels. In particular embodiments, after receiving the acknowledgement signal from the first user device, the one or more processors of the analyte monitoring device can establish the communication session with the first user device using the transceiver. The one or more processors of the analyte monitoring device can cause the transceiver to transmit a second subset of the sensor data to the first user device through the communication session. The second subset of the sensor data was not included in the data packet. In particular embodiments, the one or more processors of the analyte monitoring device can encrypt the identified subset of the sensor data using an encryption key shared between the analyte monitoring device and the first user device. In particular embodiments, the encryption key can be dynamically determined or identified using a key-rotation scheme. In particular embodiments, the priority level associated with the sensor data can be based on a time elapsed since the sensor data was collected. The sensor data with a highest priority level can be the most recently collected. In particular embodiments, the priority level associated with the sensor data is based on a condition of the subject determined from the sensor data. In particular embodiments, the one or more processors of the analyte monitoring device prepares connection data associated with establishing the communication session with the analyte monitoring device based on a periodically occurring window of time. In particular embodiments, the analyte can be, by way of example and not limitation, glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc. In particular embodiments, the data packet further includes a temperature, heart rate, blood pressure, or movement data of the subject.

According to other aspects of the disclosed subject matter, systems and methods can include a user device receiving a data packet from an analyte sensor associated with a subject. The user device can identify a data payload of the data packet. The user device can decrypt the data payload using an encryption key shared between the analyte sensor and the user device. The user device can extract analyte data for the subject from the decrypted data payload. The extracted analyte data can correspond to a most recently generated subset of analyte data gathered from the subject. The user device can output the extracted analyte data in an interface of the user device. In particular embodiments, while outputting the extracted analyte data, the interface of the user device can indicate that the extracted analyte data corresponds to a current or most recently generated analyte reading of the subject by the analyte sensor. In particular embodiments, the user device can output an alarm based on the analyte data. In particular embodiments, the user device can extract identification information for the analyte sensor from the data payload of the data packet. The user device can send an acknowledgement signal to the analyte sensor that indicates that the extracted analyte data has been received. The user device can establish a communication session with the analyte sensor based on the identification information for the analyte sensor. The user device can receive a collection of analyte data for the subject from the analyte sensor. In particular embodiments, the communication session is associated with a current time and when the analyte sensor and the user device have established a previous communication session, the previous communication session corresponds to a previous time. The historical collection of analyte data includes analyte data for the subject collected by the analyte sensor between the previous time and the current time. In particular embodiments, the user device can be associated with a user who has been authenticated by the subject to receive the analyte data on behalf of the subject.

According to other aspects of the disclosed subject matter, systems and method can include an analyte monitoring device that includes one or more processors, an analyte sensor, a communication module, and one or more memories communicatively coupled to the one or more processors, the analyte sensor, and the communication module. The one or more processors can be configured to generate sensor data indicative of an analyte level measured by the analyte sensor. At least a portion of the analyte sensor is transcutaneously positioned in contact with a bodily fluid of the subject. The one or more processors can be configured to store the sensor data in the one or more memories. The one or more processors can identify, from the one or more memories, a first subset of the sensor data corresponding to a first time. The one or more processors can prepare a data packet including the identified subset of the sensor data and connection data associated with establishing a communication session with the analyte monitoring device. The one or more processors can cause the communication module to transmit the data packet to one or more user devices within a communication range of the communication module. The one or more processors can receive, through the communication module, a communication session request from a first user device of the one or more user devices. The one or more processors can cause the communication module to transmit a second data packet to the first user device, the second data packet including a second subset of the data corresponding to a second time.

To further advantages and in accordance with the purpose of the disclosed subject matter, as embodied and broadly described, the disclosed subject matter further includes systems and methods for establishing, maintaining, and transmitting data to multiple receiving devices using concurrent communication sessions. Exemplary systems and methods can include an analyte monitoring device for monitoring a subject using an analyte monitoring device. The analyte monitoring device can include one or more processors, an analyte sensor, a communication module, and one or more memories communicatively coupled to the one or more processors, the analyte sensor, and the communication module. The one or more memories include instructions executable by the one or more processors to configure the one or more processors to perform operations in accordance with the techniques disclose herein. One or more processors of the analyte monitoring device generate sensor data indicative of an analyte level measured by an analyte sensor of the analyte monitoring device. At least a portion of the analyte sensor is transcutaneously positioned in contact with a bodily fluid of the subject. The one or more processors of the analyte monitoring device receive a first request for the sensor data from a first device and a second request for the sensor data from a second device. The one or more processors of the analyte monitoring device select a first subset of the sensor data responsive to the first request. The one or more processors of the analyte monitoring device select a second subset of the sensor data responsive to the second request. The one or more processors of the analyte monitoring device prepare a first data packet including the first subset of the sensor data and a second data packet including the second subset of the sensor data. The one or more processors of the analyte monitoring device cause the communication module of the analyte monitoring device to transmit the first data packet to the first device. The one or more processors of the analyte monitoring device cause the communication module of the analyte monitoring device to transmit the second data packet to the second device.

In particular embodiments, prior to causing the communication module of the analyte monitoring device to transmit the second data packet to the second device, the one or more processors of the analyte monitoring device receive, through the communication module and from the first device, an acknowledgement signal indicating receipt of the first subset of the sensor data. In particular embodiments, the first request and the second request include criteria for selecting the first subset of the sensor data and the second subset of the sensor data, respectively. In particular embodiments, the one or more processors of the analyte monitoring device select the first subset of the sensor data or the second subset of the sensor data based on a priority level associated with the sensor data. In particular embodiments, the one or more processors of the analyte monitoring device cause the communication module to transmit the first data packet to the first device before causing the communication module to transmit the second data packet to the second device based on the analyte monitoring device receiving the first request for the sensor data before receiving the second request for the second data. In particular embodiments, the first device or the second device is a fitness monitor or fitness device. In particular embodiments, the first device or the second device includes medical components for use by the subject based on the first subset of the sensor data or the second subset of the sensor data. In particular embodiments, the first device or the second device includes networking components to transmit the first subset of the sensor data or the second subset of the sensor data to one or more remote devices. In particular embodiments, the first device is a smartphone and the second device is a smartwatch.

In particular embodiments, the one or more processors of the analyte monitoring device establish, a communication session with the second device through communication with the first device by: receiving, from the first device and via the communication module, a connection request including identification information for the second device and information to facilitate a communication session with the second device, where the identification information was received by the first device from the second device during a communication session between the first device and the second device; transmitting an acknowledgement of the connection request to the second device using the information to facilitate the communication session with the second device; and performing a mutual authentication with the second device to generate a shared encryption key for subsequent communication sessions. In particular embodiments, the first request for the sensor data includes an identifier for the first device. The identifier is an index in a mapping table stored by the analyte monitoring device. The one or more processors of the analyte monitoring device identify the first device based on querying the mapping table using the index from the first request. In particular embodiments, the one or more processors of the analyte monitoring device encrypt the first subset of the sensor data using a first encryption key shared between the analyte monitoring device and the first device and encrypt the second subset of the sensor data using a second encryption key shared between the analyte monitoring device and the second device. In particular embodiments, the first encryption key and second encryption key are dynamically determined or identified using a key-rotation scheme. In particular embodiments, the analyte includes glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, or uric acid.

For purpose of illustration and not limitation, reference is made to the exemplary embodiment of an analyte monitoring system 100 for use with the disclosed subject matter as shown in FIG. 1. FIG. 1 illustrates an operating environment of a, preferably, low-power analyte monitoring system 100 capable of embodying the techniques described herein. The analyte monitoring system 100 can include a system of components designed to provide monitoring of parameters, such as analyte levels, of a human or animal body or can provide for other operations based on the configurations of the various components. For example, the analyte monitoring system 100 can provide continuous glucose monitoring to users or can provide for the delivery of drugs and other medicants. As embodied herein, the system can include a low-power analyte sensor 110, also referred to as a sensor worn by the user or attached to the body for which information is being collected. As embodied herein, the analyte sensor 110 can be a sealed, disposable device, to improve ease of use and reduce risk of tampering, as discussed further herein. The low-power analyte monitoring system 100 can further include a dedicated reading device 120 configured as described herein to facilitate retrieval and delivery of data, including analyte data, from the analyte sensor 110.

As embodied herein, the analyte monitoring system 100 can, additionally or alternatively, include a software or firmware library or application provided to a third-party and incorporated into a multi-purpose hardware device 130 such as a mobile phone, tablet, personal computing device, or other similar computing device capable of communicating with the analyte sensor 110 over a communication link. Multi-purpose hardware can further include embedded devices, including, but not limited to insulin pumps or insulin pens, having an embedded library configured to communicate with the analyte sensor 110. Multi-purpose device 130 embodying and executing the software library can be referred to as a data receiving device for communicating with the analyte sensor 110. As used herein, a dedicated data receiving device 120 refers to a hardware device specifically manufactured for communicating with the analyte sensor 110 within the analyte monitoring system 100 whereas a multi-purpose data receiving device 130 refers to a suitably configured hardware device which incorporates the software or firmware library or is executing the application. As used herein, a data communicating device refers to either or both of a dedicated data receiving device 120 or a multi-purpose data receiving device 130. It will be understood that the security architecture and design principles discussed herein are equally applicable to any suitably configured system involving an analyte sensor 110, a suitably configured dedicated data receiving device 120 or multi-purpose data receiving device 130, and other similar components as those described herein. The role of the analyte sensor 110 can be defined by the nature of the sensing hardware embodied in the analyte sensor 110.

As embodied herein, the analyte sensor 110 can include small, individually-packaged disposable devices with a predetermined active use lifetime (e.g., 1 day, 14 days, 30 days, etc.). Sensors 110 can be applied to the skin of the user body and remain adhered over the duration of the sensor lifetime. As embodied herein, sensors 110 can be designed to be selectively removed and remain functional when reapplied.

Although the illustrated embodiments of the analyte monitoring system 100 include only one of each of the analyte sensor 110, dedicated data receiving device 120, multi-purpose data receiving device 130, user device 140, and remote server 150, this disclosure contemplates the analyte monitoring system 100 incorporate multiples of each components interacting throughout the system. For example, the embodiments disclosed herein include multiple sensors 110 that can be associated with multiple users which are in communication with the remote server 150. Additionally, the remote server is illustrated as a single entity 150, however will be understood that it can encompass multiple networked servers that can be geographically distributed to reduce latency and introduce deliberate redundancy to avoid monitoring system downtime.

Figure 2:
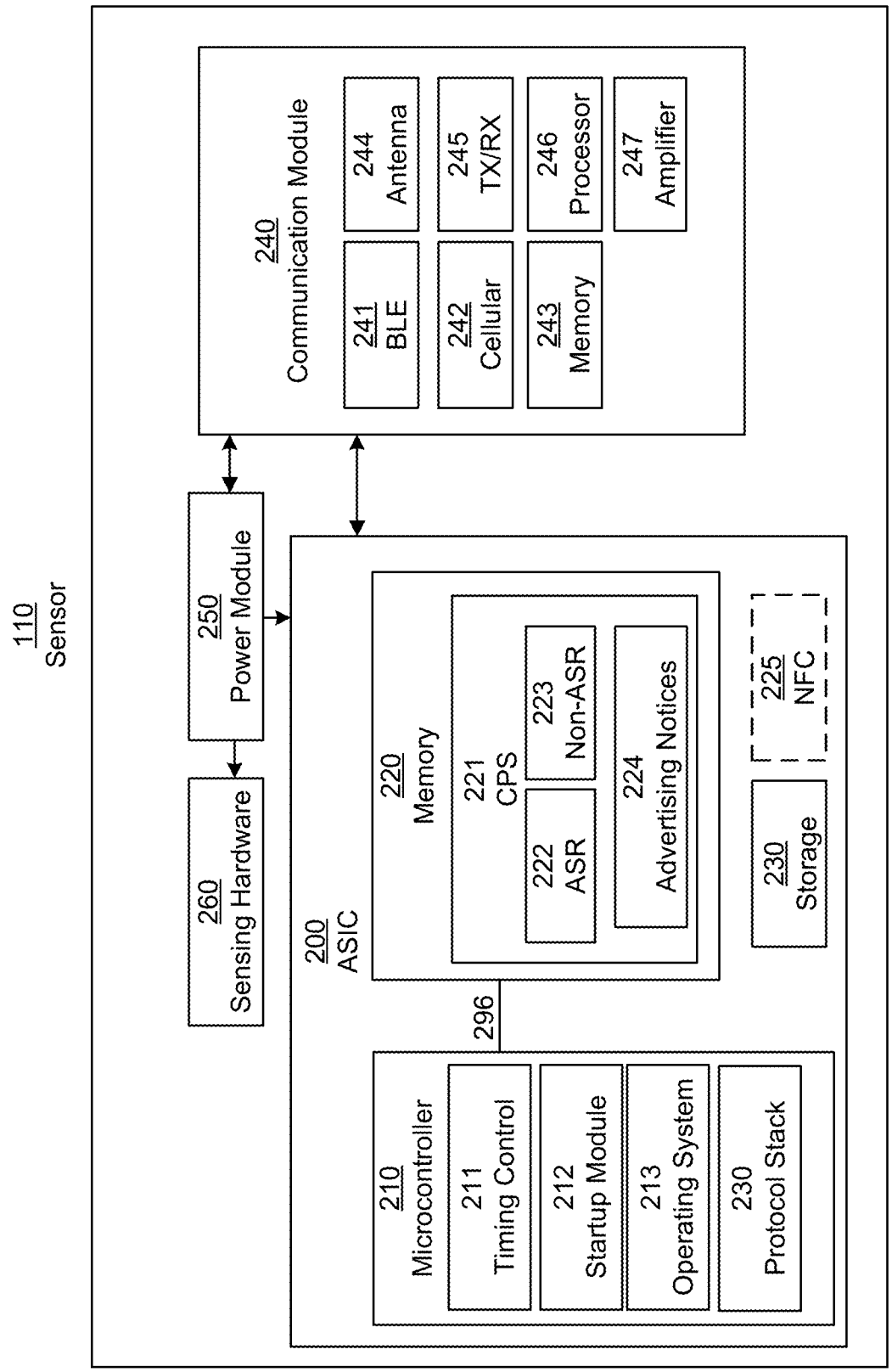
FIG. 2 is a block diagram illustrating an example analyte sensor according to exemplary embodiments of the disclosed subject matter.

For purpose of illustration and not limitation, reference is made to the exemplary embodiment of an analyte sensor 110 for use with the disclosed subject matter as shown in FIG. 2. FIG. 2 illustrates a block diagram of an example analyte sensor 110 according to exemplary embodiments compatible with the security architecture and communication schemes described herein. As embodied herein, the analyte sensor 110 can include an Application-Specific Integrated Circuit ("ASIC") 200 communicatively coupled with a communication module 240. As an example only and not by way of limitation, example communication modules 240 can include a Bluetooth Low-Energy ("BLE") chipset 241, Near-Field Communication ("NFC") chipset, or other chipsets for use with similar short-range communication schemes, such as a personal area network according to IEEE 802.15 protocols, IEEE 802.11 protocols, infrared communications according to the Infrared Data Association standards (IrDA), etc. The communication module 240 can transmit and receive data and commands via interaction with similarly-capable communication modules of a dedicated data receiving device 120 or multi-purpose data receiving device 130. As embodied herein, certain communication chipsets can be embedded in the ASIC 200 (e.g., an NFC antenna 225).

As embodied herein, as the analyte sensor 110 is designed to be power-efficient, low-cost, and possibly disposable, the ASIC 200 can include a microcontroller core 210, on-board memory 220, and storage memory 230. The storage memory 230 can store data used in an authentication and encryption security architecture. The data can have various elements and uses, including as described in the examples herein. The ASIC 200 can receive power from a power module 250, such as an on-board battery or from an NFC pulse. The power module 250 can store only a relatively small charge. As embodied herein, the analyte sensor 110 can be a disposable device with a predetermined life span, and without wide-area network communication capability. As embodied herein, the communication module 240 can provide for communication under battery power.

The microcontroller 210 further includes timing control circuitry 211 used, among other things, to wake the sensor 110 from a sleep state. The timing control circuitry 211 can include a clock for synchronizing the timing of advertising or connection events and for entering a sleep state between the advertising or connection events. The clock can determine when the sensor 110 should wake up next after processing the advertising or connection events before going to sleep. The timing circuitry 211 can then set an event to wake up in time for the next advertising or connection events. Additionally, the microcontroller 210 can include a startup module 212. The startup module can include program instructions saved in ROM that, when executed, are utilized to control modules within the sensor 110, such as the memory 220, communication module 240, and the like. Additionally or alternatively, the startup module 212 can be located on another circuit within the sensor 110. The microcontroller 210 includes an operating system module 213. The operating system module 213 supports the applications or other individual functions that run within the sensor 110. Additionally or alternatively, the operating system module 213 can be located on another circuit. The sensor 110 can include a protocol stack 230, which can include a controller and a host, each containing various communication layers. The protocol stack 230 can include or embody the operations for the sensor 110 to communicate with other device using one or more communication protocols. Additionally or alternatively, the protocol stack 230 can be located on another circuit within the sensor 110 such as within the communication module 240.

Although this disclosure is described with respect to exemplary configurations of the analyte sensor 110 and the ASIC 200, other suitable configurations are envisioned. As an example, processing hardware of the analyte sensor 110 can be implemented as another type of special-purpose processor, such as a field programmable gate array (FPGA). As embodied herein, the processing hardware of the analyte sensor 110 can include a general-purpose processing unit (e.g., a CPU) or another programmable processor that is temporarily configured by software to execute the functions of the analyte sensor 110. More generally, the processing hardware can be implemented using hardware, firmware, software, or a suitable combination of hardware, firmware, and software. For purpose of illustration and not limitation, the processing hardware of the analyte sensor 110 can be defined by one or more factors including computational capability, power capacity, memory capacity, availability of a network connection, etc.

As embodied herein, the communication module 240 of the sensor 100 can be or include one or more modules to support the analyte sensor 110 communicating with other devices of the analyte monitoring system 100. In certain embodiments, the analyte sensor 110 can communicate, for example, with a dedicated data receiving device 120 or user device 140. The communication module 240 can include, for example, a cellular radio module. The cellular radio module can include one or more radio transceivers and/or chipsets for communicating using broadband cellular networks, including, but not limited to third generation (3G), fourth generation (4G), and fifth generation (5G) networks. Using the cellular radio module the analyte sensor 110 can communicate with the remote devices (e.g., remote server 150) to provide analyte data (e.g., sensor readings) and can receive updates or alerts for the user.

As another example, the communication module 240 can include a BLE module 241 and/or an NFC module to facilitate communication with a dedicated data receiving device 120 or user device 140 acting as an NFC scanner or BLE endpoint. As used throughout this disclosure, Bluetooth Low Energy ("BLE") refers to a short-range communication protocol optimized to make pairing of Bluetooth devices simple for end users. The communication module 240 can include additional or alternative chipsets for use with similar short-range communication schemes, such as a personal area network according to IEEE 802.15 protocols, IEEE 802.11 protocols, infrared communications according to the Infrared Data Association standards (IrDA), etc. The communication module 240 can transmit and receive data and commands via interaction with similarly-capable communication modules of a dedicated data receiving device 120 or user device 140. Certain communication chipsets can be embedded in the ASIC 200 (e.g., an NFC antennae loop). Additionally, although not illustrated, the communication module 240 of the analyte sensor 110 can include a radio for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)). The communication module 243 can further include a memory 243 of its own that is coupled with a microcontroller core for the communication module 240 and/or is coupled with the microcontroller core 210 of the ASIC 200 of the analyte sensor 110.

The communication module 240 can include communication circuitry, such as an antenna 244, a transceiver 245, memory 243, a processor 246 and a collection of one or more transmit amplifiers and receive amplifiers (shown collectively as amplifiers 247). Although not illustrated, the communication module 240 can include multiple sets of communication circuitry (e.g., one for each supported communication protocol). For brevity, only a single set of the communication circuitry is illustrated. In certain cases, the processor 246 of the communication circuitry can be similar to the microcontroller 210. Optionally, the transceiver 245 can be provided as a single component or a separate transmitter and a separate receiver. The one or more transmit amplifiers 247 are configured to be selectively connected between an output of the transmitter of the transceiver 245 and the antenna 244. The one or more receive amplifiers 247 are configured to be selectively connected between the antenna 244 and an input of the receiver of the transceiver 245.

As explained herein, the transmitter and receiver of the transceiver 245 exhibit certain power and sensitivity limits based on the components and design of a particular implementation, without the addition of transmit or receive amplifiers 247. One or more transmit amplifiers 247 can be provided to be selectively connected between the output of the transmitter in the antenna to boost the transmit power, such as up to 10 dBm. As another example, the receiver of the transceiver 245 can exhibit a receive sensitivity down to −85 dBm when operated alone without the addition of a separate receive amplifier 247. One or more receive amplifiers 247 can be provided to be selectively connected between the antenna 244 and the input of the receiver of the transceiver 245 to boost the receive sensitivity, such as down to −100 dBm.

As explained herein, while the communication module 240 is initialized, the transmitter of the transceiver 245 can transmit advertisement notices (e.g., communication packets comprising at least a payload including information to facilitate the initiation of discovery and a communication session with another device) arranged in complexes, followed by sleep states in accordance with an advertisement interval. The receiver of the transceiver 245 performs scan operations, during a receive window, to scan for connection requests. Connection requests can be sent in response to advertisement notices or independently by other devices. The scan operation, during an individual receive window, can be performed during the same period of time as transmission of the advertisement notices 224 over corresponding advertisement channels. Optionally, the receive window and scan operation can continue after completion of transmission of the advertisement notices. Hence, the scan operation and receive window can temporarily align with the complex of advertisement notices or extend beyond the complex of advertisement notices 224 into the sleep state of the advertisement interval.

As embodied herein a first layer of security for communications between the analyte sensor 110 and other devices can be established based on security protocols specified by and integrated in the communication protocols used for the communication (e.g., BLE security protocols, Wi-Fi 5 security protocols). Another layer of security can be based on communication protocols that necessitate close proximity of communicating devices. Furthermore certain packets and/or certain data included within packets can be encrypted while other packets and/or data within packets is otherwise encrypted or not encrypted. As an example, connection data and/or connection packets devoted to establishing communication connections between devices can be largely unencrypted—sensitive analyte data can be encrypted, even if included in a connection packet in order to facilitate discovery by other devices.

Additionally or alternatively, another layer of security can be based on used, by the analyte sensor 110 and other devices in communication, of application layer encryption using one or more block ciphers to establish mutual authentication and encryption of other devices in the analyte monitoring system 100. The use of a non-standard encryption design implemented in the application layer has several benefits. One benefit of this approach is that in certain embodiments the user can complete the pairing of an analyte sensor 110 and another device with minimal interaction, e.g., using only an NFC scan and without requiring additional input, such as entering a security pin or confirming pairing.

To perform its functionalities, the sensor 100 can further include suitable sensing hardware 260 appropriate to its function. As embodied herein, the sensing hardware 260 can include an analyte sensor transcutaneously or subcutaneously positioned in contact with a bodily fluid of a subject. The analyte sensor can generate sensor data containing values corresponding to levels of one or more analytes within the bodily fluid. Additionally or alternatively, the sensing hardware 260 can include, for example, an autoinjector prescribed to a user for self-administering a drug or other medicament. Accordingly, the sensing hardware 260 can include a mechanism that drives a needle or a plunger of a syringe in order to subcutaneously deliver a drug. The syringe can be pre-filled with the drug and can operate in response to a triggering event. For example, the mechanism can drive the needle into the user and advance the plunger to deliver the drug subcutaneously via the needle.

As embodied herein, the analyte sensor 110 can be configured as an on-body injector attachable to a user's body tissue (e.g., skin, organ, muscle, etc.) and capable of automatically delivering a subcutaneous injection of a fixed or user-selected dose of a drug over a controlled or selected period of time. In such embodiments, the sensing hardware 260 or analyte sensor can include, for example, an adhesive or other means for temporarily attaching the sensing hardware 260 to the user's body tissue, a primary container for storing a drug or medicament, a drive mechanism configured to drive or permit the release of a plunger to discharge the drug from the primary container, a trocar (e.g., a solid core needle), a flexible cannula disposed around the trocar, an insertion mechanism configured to insert the trocar and/or flexible cannula into the user and optionally retract the trocar leaving the flexible cannula in the user, a fluid pathway connector configured to establish fluid communication between the primary container and the flexible cannula upon device activation, and an actuator (e.g., a user displaceable button) configured to activate the device. As embodied herein, the on-body injector can be pre-filled and/or pre-loaded.

In addition to mechanical components, the sensing hardware 260 can include electric and/or electronic components. For example, an electronic switch can be coupled to the mechanism. The analyte sensor 110 can establish an authenticated communication, receive an encrypted signal, decrypt the signal using the techniques of this disclosure, determine that the signal includes a command to operate the switch, and cause the switch to drive the needle. Thus, the analyte sensor embodied herein can be configured to perform an analyte function using the sensing hardware 260 in response to a remote command.

As embodied herein, the sensing hardware 260 can include a travel sensor and an analog-to-digital converter to generate a digital signal indicative of the distance travelled by the needle or plunger. Upon delivering the medicament, the low-power analyte sensor 110 can obtain a reading from the sensor, encrypt the reading using the techniques of this disclosure, and securely report the reading to another device. Additionally or alternatively, the analyte sensor 110 can report other measurements or parameters, such as a time at which the medicant was delivered, volume of medicant delivered, any issues encountered while delivering the medicament, etc. The analyte sensor 110 can be configured to provide data related to the operation of the sensing hardware 260 to a remote device.

The sensing hardware 260 can be configured to implement any suitable combination of one or more analyte functions and can include one or more sensing components. Sensing components can be configured to detect an operational state of the analyte sensor 110 (e.g., unpackaged/ready for administration, sterile barrier removal, contact with user's body tissue, cannula and/or needle insertion, drug delivery initiation, actuator or button displacement, drug delivery completion, plunger position, fluid pathway occlusion, etc.), a condition of the analyte sensor 110 or drug contained therein (e.g., temperature, shock or vibration exposure, light exposure, drug color, drug turbidity, drug viscosity, geographic location, spatial orientation, temporal information, ambient air pressure, etc.), and/or physiological information about the user (e.g., body temperature, blood pressure, pulse or heart rate, glucose levels, physical activity or movement, fingerprint detection, etc.). This detected information can be offloaded from the analyte sensor 110 to facilitate storage and analysis, for example to a dedicated data receiving device 120, multi-purpose data receiving device 130, or remote server 150. As embodied herein, the analyte sensor 110 can be configured to both receive encrypted data from other devices and transmit encrypted data to the other devices.

Referring still to FIG. 2, the ASIC 200 of the analyte sensor 110 can be configured to dynamically generate authentication and encryption keys using the data retained within the storage memory 230. The storage memory 230 can also be pre-programmed with a set of valid authentication and encryption keys to use with particular classes of devices. The ASIC 200 can be further configured to perform authentication procedures with other devices (e.g., handshake, mutual authentication, etc.) using received data and apply the generated key to sensitive data prior to transmitting the sensitive data, such as sending the sensitive data to the remote server 150 via the communication module 240. The generated key can be unique to the analyte sensor 110, unique to a pair of devices (e.g., unique to a particular pairing of an analyte sensor 110 and a dedicated data receiving device 120), unique to a communication session between an analyte sensor 110 and other device, unique to a message sent during a communication session, or unique to a block of data contained within a message. The techniques implemented by the ASIC 200 and communication module 240 of the analyte sensor 110 are discussed in more detail herein.

Figure 3:
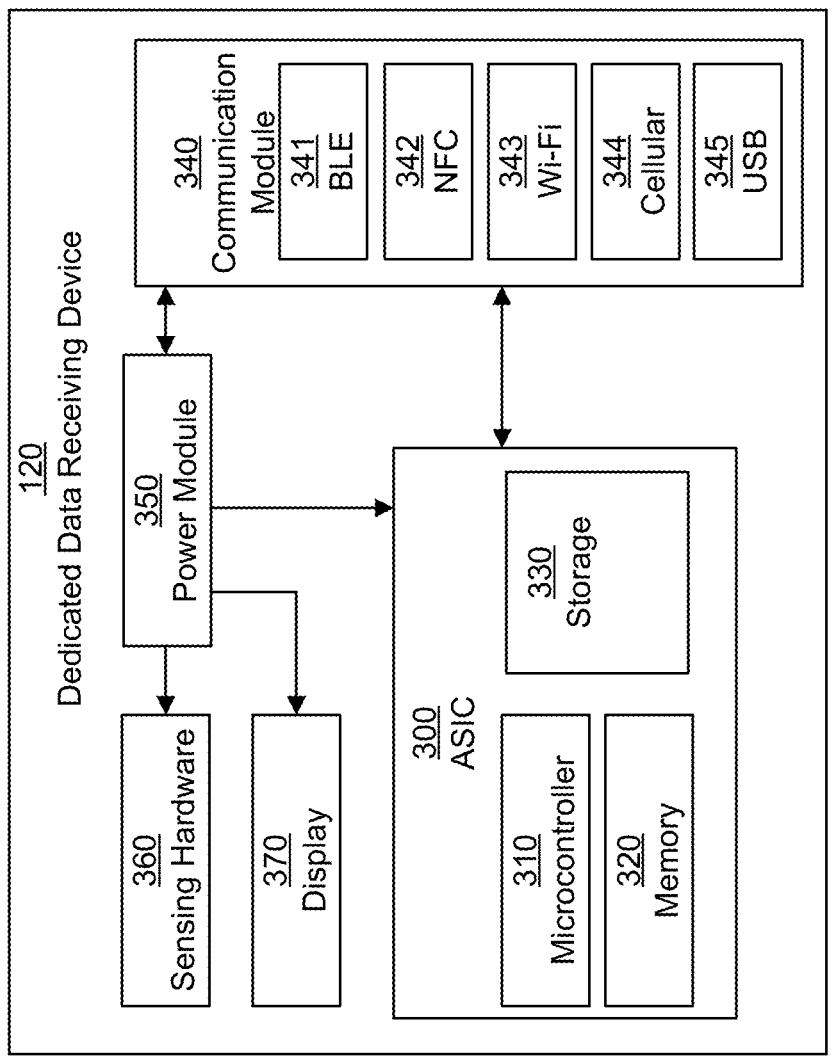
FIG. 3 is a block diagram illustrating an example dedicated data receiving device for communicating with the sensor according to exemplary embodiments of the disclosed subject matter.

For purpose of illustration and not limitation, reference is made to the exemplary embodiment of a dedicated data receiving device 120 for use with the disclosed subject matter as shown in FIG. 3. The dedicated data receiving device 120, and the related multi-purpose data receiving device 130, includes components germane to the discussion of the analyte sensor 110 and its operations and additional components can be included. In particular embodiments, the dedicated data receiving device 120 and multi-purpose data receiving device 130 can be or include components provided by a third party and are not necessarily restricted to include devices made by the same manufacturer as the sensor 110.

FIG. 3 illustrates an example dedicated data receiving device 120 compatible with the security and computing architecture described herein with respect to exemplary embodiments. As embodied herein, the dedicated data receiving device 120 can include a small-form factor device. The dedicated data receiving device 120 can optionally not be as memory- or processing-power constrained as the analyte sensor 110, and as embodied herein, the dedicated data receiving device 120 can include sufficient memory for operational software storage and data storage, and sufficient RAM for software execution to communicate with analyte sensor 110 as described herein. As illustrated in FIG. 3, the dedicated data receiving device 120 includes an ASIC 300 including a microcontroller 310, memory 320, and storage 330 and communicatively coupled with a communication module 340. As embodied herein, the ASIC 300 can be identical to the ASIC 200 of the analyte sensor 110. Alternatively, the ASIC 300 can be configured to include additional computing power and functionality. Power for the components of the dedicated data receiving device 120 can be delivered by a power module 350, which as embodied herein can include a rechargeable battery, allowing for sustained operations and continued use.

The dedicated data receiving device 120 can further include a display 370 for facilitating review of analyte data received from an analyte sensor 110 or other device (e.g., user device 140 or remote server 150). The display 370 can be a power-efficient display with a relatively low screen refresh rate to conserve energy use and further reduce the cost of the dedicated data receiving device 120. The display 370 can be a low-cost touch screen to receive user input through one or more user interfaces. Although not illustrated, the dedicated data receiving device 120 can include separate user interface components (e.g., physical keys, light sensors, microphones, etc.). Power for the components of the dedicated data receiving device 120 can be delivered by a power module 350, which as embodied herein can include a rechargeable battery, allowing for sustained operations and continued use.

Although illustrated as separate components, in particular embodiments, a processor of the communication module 340 can perform the processing operations ordinarily performed by the microcontroller 310 of the ASIC 300. Therefore, the ASIC 300 can be removed, and memory and other storage added to the communication module to simplify the hardware required of the dedicated data receiving device 120.

The communication module 340 can include a BLE 341 module and an NFC module 342. The dedicated data receiving device 120 can be configured to wirelessly couple with the analyte sensor 110 and transmit commands to and receive data from the analyte sensor 110. As embodied herein, the dedicated data receiving device 120 can be configured to operate, with respect to the analyte sensor 110 as described herein, as an NFC scanner and a BLE end point via specific modules (e.g., BLE module 342 or NFC module 343) of the communication module 340. For example, the dedicated data receiving device 120 can issue commands (e.g., activation commands for a data broadcast mode of the sensor; pairing commands to identify the dedicated data receiving device 120 with the analyte sensor 110) to the analyte sensor 110 using a first module of the communication module 340 and receive data from and transmit data to the analyte sensor 110 using a second module of the communication module 340.

As embodied herein, the dedicated data receiving device 120 can be configured for communication via a Universal Serial Bus (USB) module 345 of the communication module 340. The dedicated data receiving device 120 can communicate with a user device 140 for example over the USB module 345. The dedicated data receiving device 120 can, for example, receive software or firmware updates via USB, receive bulk data via USB, or upload data to the remote server 150 via the user device 140. USB connections can be authenticated on each plug event. Authentication can use, for example, a two-, three-, four, or five-pass design with different keys. The USB system can support a variety of different sets of keys for encryption and authentication. Keys can be aligned with differential roles (clinical, manufacturer, user, etc.). Sensitive commands that can leak security information can trigger authenticated encryption using an authenticated additional keyset.

As another example, the communication module 340 can include, for example, a cellular radio module 344. The cellular radio module 344 can include one or more radio transceivers for communicating using broadband cellular networks, including, but not limited to third generation (3G), fourth generation (4G), and fifth generation (5G) networks. Using the cellular radio module 344 the dedicated data receiving device 120 can communicate with the remote server 150 to receive analyte data or provide updates or input received from a user (e.g., through one or more user interfaces). Additionally, the communication module 340 of the dedicated data receiving device 120 can include a Wi-Fi radio module 343 for communication using a wireless local area network according to one or more of the IEEE 802.11 standards (e.g., 802.11a, 802.11b, 802.11g, 802.11n (aka Wi-Fi 4), 802.11ac (aka Wi-Fi 5), 802.11ax (aka Wi-Fi 6)).

As used throughout this disclosure, Bluetooth Low Energy ("BLE") refers to a short-range communication protocol optimized to make pairing of Bluetooth devices simple for end users. As described herein, the use of BLE on the analyte sensor 110 can optionally not rely on standard BLE implementation of Bluetooth for security but can instead use application layer encryption using one or more block ciphers to establish mutual authentication and encryption. The use of a non-standard encryption design implemented in the application layer has several benefits. One benefit of this approach is that the user can complete the pairing of the analyte sensor 110 and dedicated data receiving device 120 with only an NFC scan and without involving the user providing additional input, such as entering a security pin or confirming BLE pairing between the data receiving device and the analyte sensor 110. Another benefit is that this approach mitigates the potential to allow devices that are not in the immediate proximity of the analyte sensor 110 to inadvertently or intentionally pair, at least in part because the information used to support the pairing process is shared via a back-up short-range communication link (e.g., NFC) over a short range instead of over the longer-range BLE channel. Furthermore, as BLE pairing and bonding schemes are not involved, pairing of the analyte sensor 110 can avoid implementation issues by chip vendors or vulnerabilities in the BLE specification.

As embodied herein, the on-board storage 330 of the dedicated data receiving device 120 can be capable of storing analyte data received from the analyte sensor 110 over an extended period of time. Further, the multi-purpose data receiving device 130 or a user computing device 140 as embodied herein can be configured to communicate with a remote server 150 via a wide area network. As embodied herein, the analyte sensor 110 can provide sensitive data to the dedicated data receiving device 120 or multi-purpose data receiving device 130. The dedicated data receiving device 120 can transmit the sensitive data to the user computing device 140. The user computing device 140 (or the multi-purpose data receiving device 130) can in turn transmit that data to a remote server 150 for processing and analysis. In communicating with the remote server 150, multi-purpose data receiving device 130 and user computing device 140 can generate unique user tokens according to authentication credentials entered by a user and stored at the respective device. The authentication credentials can be used to establish a secure connection to the remote server 150 and can be further used to encrypt any sensitive data provided to the remote server 150 as appropriate. As embodied herein multi-purpose data receiving device 130 and user computing device 140 can optionally not be as restricted in their use of processing power, and therefore, standard data encryption and transmission techniques can be used in transmitted to the remote server 150.

As embodied herein, the dedicated data receiving device 120 can further include sensing hardware 360 similar to, or expanded from, the sensing hardware 260 of the analyte sensor 110. As an example only, and not by way of limitation, in an embodiment in which the sensing hardware 260 of the analyte sensor 110 is configured for continuous glucose monitoring, the sensing hardware 360 of the dedicated data receiving device 120 can be configured with a blood glucose meter, compatible for use with blood glucose test strips, thus expanding on the blood glucose monitoring of the analyte sensor 110. In particular embodiments, the compatible device 130 can be configured to operate in coordination with the analyte sensor 110 and based on analyte data received from the analyte sensor 110. As an example, where the analyte sensor 110 glucose sensor, the compatible device 130 can be or include an insulin pump or insulin injection pen. In coordination, the compatible device 130 can adjust an insulin dosage for a user based on glucose values received from the analyte sensor.

Figure 4:
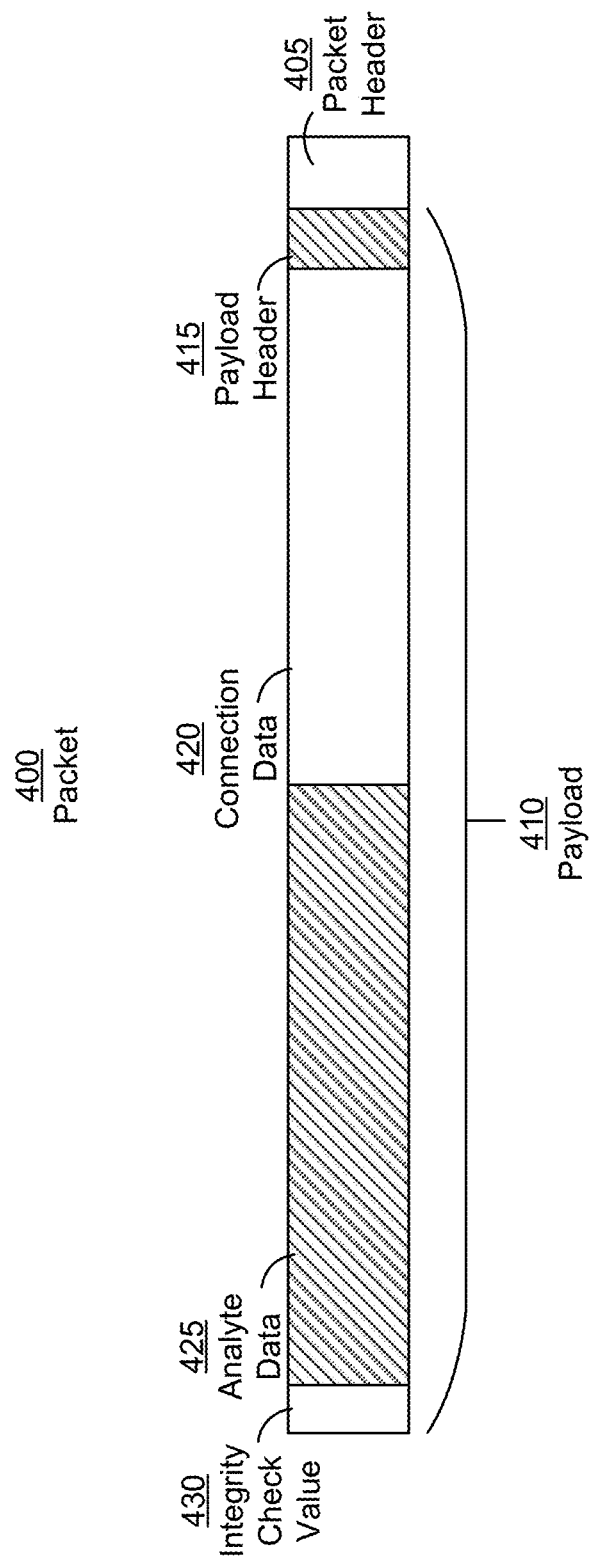
FIG. 4 is a diagram illustrating an example packet.

FIG. 4 illustrates an example packet according to certain embodiments. In particular, FIG. 4 illustrates a layout for a packet 400 that be used to transmit both analyte data and connection data (e.g., advertising data or data otherwise used to establish a connection between devices). The packet 400 can be prepared according to the techniques disclosed herein. In particular embodiments, the packet 400 can include a packet header 405. The packet header 405 can include, as an example and not limitation, information that will be used by receiving devices (e.g., dedicated data receiving device 120 or user device 140) to identify how the payload 410 should be interpreted. As an example, the packet header 405 can identify that the packet 400 includes connection data. As another example, the packet header 405 can identify that the packet 400 includes analyte data. The packet header 405 can include one or more identifying values designated by the manufacturer of the analyte sensor 110 or selected in accordance with a communication protocol. The identifying values can uniquely indicate to receiving devices, that are configured to interpret the identifying values, the purpose and potential usage of the packet 400. The identifying values can be unique among manufacturers using, for example, a specific communication protocol compatible with the communication module of the analyte sensor 110. For example, the identifying values can indicate that the packet 400 is a data connection packet or advertising packet. As another example, the identifying values can indicate that the packet 400 is an enhanced connection packet or advertising packet that includes manufacturer-specific information, such as encrypted analyte data 425.

Additionally or alternatively, as embodied herein, the packet header 405 can include information signifying that the packet 400 originated from an analyte sensor 110. The packet 400 can indicate the manufacturer of the analyte sensor 110. In particular embodiments, the amount and extent of identifying information included in the packet header 405 can be selected in order to ensure that the payload 410 can be interpreted by receiving devices while still preserving the security of the identity of the subject, the identity of the analyte sensor 110, the analyte data included in the packet, etc.

Referring still to FIG. 4, the packet 400 can include a payload 410. The format of the payload 410 can be predetermined by the manufacturer of the analyte sensor 110 to correspond to the information included in the packet header 405. The packet header 405, therefore, can be used by receiving devices to interpret the data in the payload 410. In particular embodiments, the payload 410 can include a payload header 415, connection data 420, and analyte data 425. The payload header 415 can include further information facilitating the interpretation of the data included in the payload 410. For example, the payload header 415 can indicate an expected size of the payload 410 or categorize or otherwise indicate what information is included in the payload 410. As embodied herein, the analyte sensor 110 can operate in different modes relating to the preparation and broadcast of different categories or types of packets that include corresponding categories or types of payloads. Aspects of the data included in a given payload, such as, for example, the type of data, the format of the data, or the arrangement or layout of the data, can vary based on the category of the payload. As an example, and not limitation, in a connectable packet mode, the analyte sensor 110 can include connection data 420 in a payload 410. The connectable packet mode can be configured to facilitate the analyte sensor 110 establishing a communication session with a receiving device to offload stored data. While operating in the connectable packet mode, the analyte sensor 110 can allocate more space to connection data 420 than the analyte sensor 110 would allocate otherwise. As another example, and not limitation, in an informational packet mode, the analyte sensor 110 can include analyte data 425. The informational packet mode can be configured to facilitate the analyte sensor 110 broadcasting a selected subset of analyte data for a receiving device to receive and interpret, with a reduced focus on establishing a subsequent communication session. While operating in the informational packet mode, the analyte sensor 110 can allocate more space to analyte data 425 than the analyte sensor 110 would allocate otherwise. As another example, and not limitation, in a mixed packet mode, the analyte sensor 110 can include both connection data 420 and analyte data 425. In addition to or as an alternative to the connectable packet mode, informational packet mode, and mixed packet mode, an analyte sensor 110 can operate in various other modes and/or include additional information within the payload 410. As an example, the analyte sensor 110 can operate in a low power mode in which the analyte sensor 110 can adjust the number of packets broadcast and include data corresponding to a low power alert. The payload header 415 can specify the category of the payload 410 included in the packet 400. After a receiving device receives a packet 400, the receiving device can interpret the payload header 415 of the received packet 400 to determine the category of the payload 410 of the received packet. The receiving device can efficiently determine how to interpret the payload 410 of the received packet based on determining the category of the payload 410. Additionally or alternatively, the receiving device can detect errors in the payload 410, for example based on data retrieved from the payload 410 failing to correspond to an expected format or arrangement.

In particular embodiments, the payload 410 can include connection data 420. The connection data 420, can include a set of parameters to facilitate a receiving device establishing a connection with the analyte sensor 110. For example, the connection data 420 can include information detailing the connection procedure expected by the analyte sensor 110. The connection procedure can include an encoding scheme that will be used by the analyte sensor 110. In particular embodiments the connection data 420 can include an identifier for the analyte sensor 110 and/or for the device the analyte sensor 110 intends to connect with, if known. As an example only and not limitation, the identifier can include a unique device identifier, an identifier associated with the communication protocol (e.g., a Bluetooth identifier or BLE identifier), an identifier associated with networking and/or communication hardware of the analyte sensor 110 (e.g., a media access control address ("MAC address"), or other suitable identifier. If the communication protocol used by the analyte sensor (e.g., the communication protocol compatible with the communication module 240 of the analyte sensor 110) supports the use of multiple communication channels and/or channel hopping, the connection data can include information for the receiving device to initiate a communication session accordingly. In particular embodiments, the packet 400 can be configured to appear as a data packet or advertising packet conforming to an established communication protocol or standard supported by the communication module 240 of the sensor 110. For example, to facilitate wide compatibility with the analyte sensor 110, the analyte sensor 110 can use one or more connection-facilitating or advertising data formats as specified by the communication protocol. The connection data 420 included in the payload 410 can be configured according to those formats.

In particular embodiments, the payload 410 can further include analyte data 425. As described herein, the analyte sensor 110 can include sensing hardware 260, which can include one or more sensors. The analyte data 425 can include data received from one or more of the sensors. As an example, and not limitation, the data can include raw data from one or more components of the sensing hardware 260 (e.g., a signal value read from an analog-to-digital converter), data used to process raw data from the components of the sensing hardware 260 (e.g., a temperature level, noise level, etc.), data that has been processed by the analyte sensor 110 into another usable format (e.g., human-readable data), etc. The data can further include derivative values calculated from the sensor data, such as calculated rates of changes, trending values, projected values, etc. Additionally or alternatively, the sensing hardware 260 can include components to deliver a therapy to the subject analyte data. For example, the analyte sensor 110 can include an insulin pump and the sensing hardware 260 can include hardware to inject an amount of insulin. The analyte data 425 can include information relating to the therapy delivered, including, but not limited to, the frequency of therapy, the cumulative amount or effect of the therapy delivered, the remaining capability of the sensing hardware 260 to deliver the therapy, the time the therapy was most recently delivered, etc.

In particular embodiments, the payload 410 can further include an integrity check value 430. The integrity check value 430 can be a value computed or derived from the data included in the payload 410 or packet 400 that can serve as an way for a receiving device to efficiently determine whether the data in the payload 410 has been intentionally or unintentionally modified during transmission, encryption/decryption, etc. As described, the data stored in the payload 410 can include analyte data 425 or other sensitive data of the subject. Especially where the data can be used to generate alerts or inform diagnoses regarding the health of the subject, ensuring the integrity of the data is an important feature of the analyte monitoring system 100. In particular embodiments, when a receiving device receives the packet 400 (and decrypts the payload 410, if the integrity check value 430 is stored in the payload 410), the receiving device can compare to the value of the integrity check value 430 to a counterpart check value 430. If the received integrity check value 430 does not correspond to the counterpart check value 430, the receiving device can disregard the payload 410 or inform the analyte sensor 110, subject, or user of the receiving device of a possible error. In particular embodiments, the counterpart check value can include a value calculated by the received device after receiving the packet 400 using the same algorithm or formula and input data as would have been used by the analyte sensor 110 in preparing the integrity check value 430 prior to transmission. As an example and not limitation, the integrity check value 430 can include an error detection code with a size determined based on the size of the payload 410 and/or the packet 400. As another example and not limitation, the integrity check value 430 can include a checksum or other cryptographic hash value derived from the data in the payload 410 or packet 430.

The packet 400 can include other values not shown in FIG. 4. As an example, the packet 400 can include a counter value corresponding to the total uptime of the analyte sensor 110. The packet 400 can include a value representing the expected remaining functional life of the analyte sensor 110 (e.g., the expected remaining battery life of the analyte sensor 110, the expected remaining usefulness of any limited-time use materials within the analyte sensor 110, etc.). The packet 400 can include a timestamp corresponding, for example, to the time the analyte data 425 was collected or the time the packet 400 was sent. A receiving device can use the timestamp to verify that the analyte data 425 corresponds to data that can be useful to the subject and/or user of the receiving device. For example, if the timestamp associated with the packet 400 has an age greater than a threshold age, the receiving device can determine not to represent the analyte data 425 as containing current values for the analyte data 425, but instead represent the analyte data 425 as containing merely most recent values for the analyte data 425. In particular embodiments, the packet 400 can include manufacturer specific data that is set or requested by the manufacturer of the analyte sensor 110 and/or operator of the analyte monitoring system 100.

In particular embodiments, some or all of the data included in the data payload 410 can be encrypted. For example, the entirety of the payload 410 can be encrypted, the data included in the payload 410 besides the payload header 415 can be encrypted, only the analyte data 425 or the connection data 420 can be encrypted, etc. In particular embodiments, the analyte sensor 110 can encrypt the appropriate data prior to preparing the payload 410 and packet 400. As described herein, encryption performed by the analyte sensor 110 can be informed by balancing the computational complexity of a cipher with the lower-cost components used in the analyte sensor 110.

Figure 5:
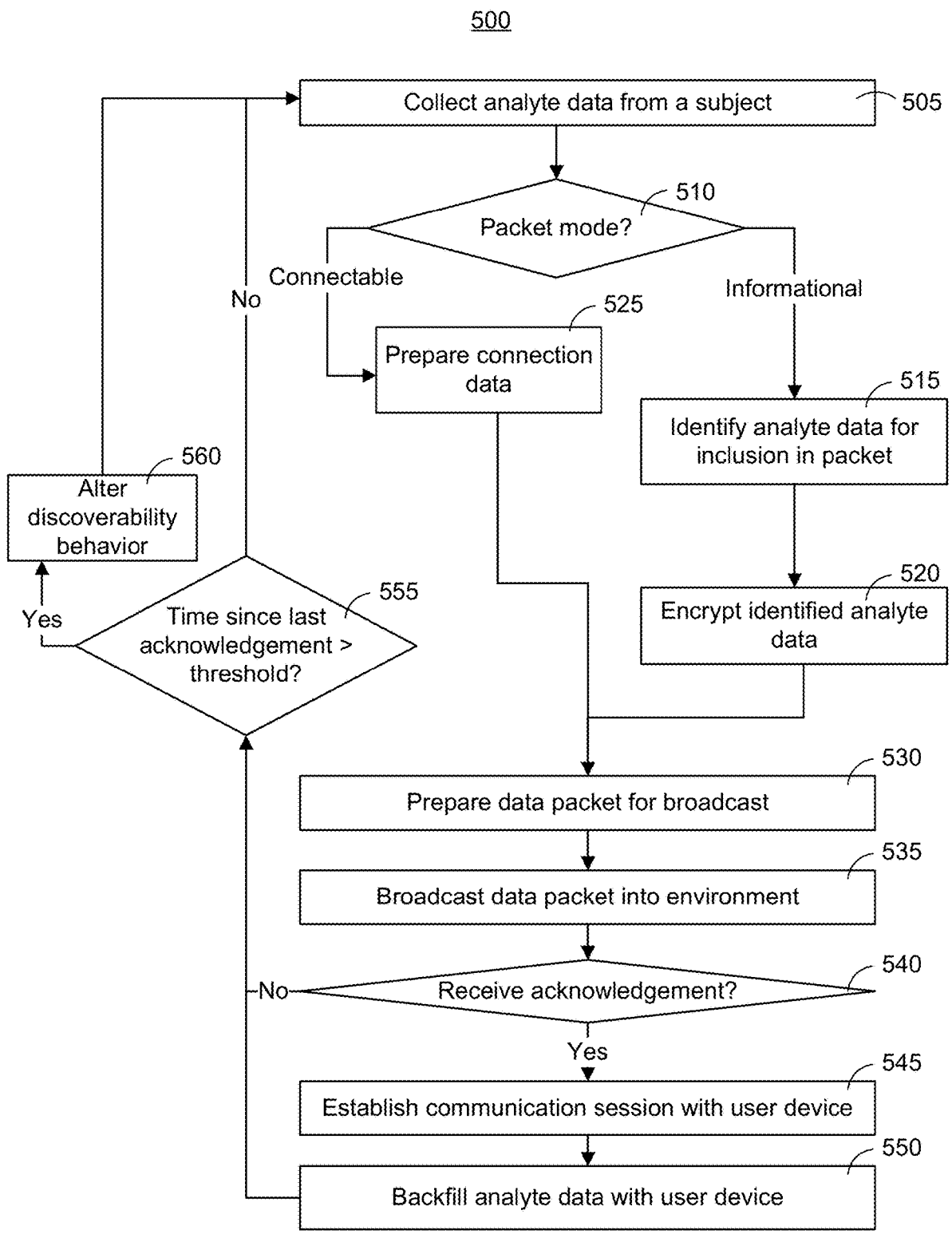
FIG. 5 is a diagram illustrating an example operational flow of an analyte sensor according to the disclosed subject matter.

FIG. 5 illustrates an example process 500 for transmitting analyte data within connection packets from an analyte sensor 110, such as an analyte monitoring device, according to the embodiments disclosed herein. The example process 500 further includes actions that can be taken by the analyte sensor 110 after the analyte data has been transmitted. Through the process 500, the analyte data is transmitted in an encrypted payload of a data packet and through communication channels used for device discoverability, expediting delivery of high-priority analyte data. As illustrated, the process 500 can be repeated, and each iteration of process 500 can follow one or more paths based, at least in part, on the behavior of the analyte sensor 110 and other devices of the analyte monitoring system 100.

At 505, the analyte sensor 110 can collect analyte data from a subject. As described herein, the analyte sensor 110 can include sensing hardware that is useful for monitoring the health status of the subject (e.g., the wearer of the analyte sensor 110). In particular embodiments, the sensing hardware can include an analyte sensor for measuring the levels of an analyte (e.g., glucose, lactate, oxygen, etc.) in a bodily fluid of the subject (e.g., blood, sweat, extracellular or interstitial fluid, etc.). In particular embodiments, the sensing hardware can include a temperature sensor, an activity or motion sensor, a heart rate sensor, or other sensing hardware. The analyte sensor 110 can receive input from the sensing hardware (e.g., analyte sensor, temperature sensor, etc.) in a streaming manner that can include or correspond to a health feature or status of the subject (e.g., levels of the analyte, blood or skin temperature, etc.). In particular embodiments, the input from the sensing hardware can be processed by the analyte sensor. The input can be temporarily stored into a memory of the analyte sensor 110 (e.g., a volatile memory or RAM of an ASIC or other control unit). As described, the analyte sensor 110 can be a relatively low-cost sensor 110 that may lack significant computing power, storage, or output capabilities (e.g., to output information relating to the analyte data). The analyte sensor 110 can therefore offload the received data, after it has been stored in the memory of the analyte sensor 110, to another device, e.g., for further processing or display.

At 510, the analyte sensor 110 can determine an operating mode of the analyte sensor 110 relating, as described herein, to the preparation and broadcast of different categories or types of packets that include corresponding categories or types of payloads. In particular, the analyte sensor 110 can periodically broadcast data from the sensing hardware and/or information to facilitate a connection between the analyte sensor 110 and a receiving device (e.g., dedicated data receiving device 120, multi-purpose data receiving device 130, or user device 140). The analyte sensor 110 can prepare and broadcast a packet, e.g., packet 400, including selected data. As an example, the analyte sensor 110 can prepare and broadcast the packet once every second, once every two seconds, once every 5 seconds, etc. As embodied herein, the analyte sensor 110 can select which information to include in the packet. For example, the analyte sensor 110 can select which information to include on a periodic basis (e.g., packets with connection data are split evenly between packets with analyte data, packets with analyte data five times for every packet with connection data, a pattern of 50 packets with analyte data followed by 5 packets of connection data, etc.). The analyte sensor 110 can select which information to include based on the last time the analyte sensor 110 connected with a receiving device or offloaded data included in the memory of the analyte sensor to a receiving device, the amount of battery life remaining or term of usefulness of the analyte sensor 110, etc.

If, at 510, the analyte sensor 110 determines that it is operating in an informational packet mode, then at 515, the analyte sensor 110 identifies analyte data for inclusion in the data packet. The analyte sensor can select analyte data from the memory of the analyte sensor 110 for inclusion in the packet. In particular embodiments, the amount of space available in the packet (e.g., in the payload 410 of the packet 400) can be adjusted in order to reduce the computational cost of preparing and sending the packet frequently and reduce the chance that only a portion of the packet can be received by a receiving device. Therefore, a subset of the analyte data stored by the analyte sensor 110 can be identified for inclusion in the packet.

In particular embodiments, the analyte sensor 110 can use a prioritization scheme to determine which analyte data to include in the packet. The analyte sensor 110 can determine a priority level for analyte data and select data for inclusion in the packet based on the priority level. As an example, the priority level can relate to an age of the analyte data (e.g., a time since the analyte data was collected). In particular embodiments, the analyte sensor 110 can set the highest priority level for the most recently collected data to ensure that, if the receiving device receives the packet and outputs the analyte data, the user of the receiving device can see the most recent or current analyte data. As another example, the analyte sensor 110 can set the highest priority level for the severity or urgency of the analyte data. For example, the analyte data can include levels of an analyte in a fluid of the subject. The levels of the analyte can be associated with one or more thresholds that indicate, for example, a range of safe levels, levels that are higher or lower than is determined to be safe, levels that are dangerously high or low, etc. The priority levels of analyte data can be determined by comparing the analyte data to the one or more thresholds. Then, if the receiving device receives the packet and outputs the analyte data, the user of the receiving device can receive the most urgent or critical data. One more prioritization schemes can be used together. For example, all analyte data of the same urgency priority level can be ordered according to the age of the analyte data.

At 520, the analyte sensor 110 can encrypt the analyte data identified for inclusion in the data packet. As described herein, the analyte data can include sensitive information about the health or identity of the subject. To protect the sensitive information, the analyte sensor 110 can use one or more block ciphers or other encryption schemes to encrypt the analyte data. In particular embodiments, the analyte sensor 110 can use, as an encryption key, a private key stored by the analyte sensor 110. As described herein, user devices that are configured (and optionally authorized) to receive and process the analyte data from the subject, can be provided a public key, related to the private key of the analyte sensor 110 to decrypt the data upon receipt. In embodiments where the analyte sensor 110 and receiving device have been identified to each other (e.g., where the analyte sensor 110 and receiving device have previously established a communication session or the receiving device issued an activation command to the analyte sensor 110), the analyte sensor 110 and receiving device can agree on a encryption key to use for subsequent iterations of the process. In particular embodiments, the encryption key can be dynamically generated, for example, based on a device secret or private value and a deterministically-changing value (e.g., a monotonically-increasing value or a timestamp). The receiving device can use the same device secret and deterministically-changing value to calculate a decryption key. In particular embodiments, the encryption key can be selected using a key-rotation scheme.

As embodied herein, the public keys shared by the analyte sensor 110 and receiving devices can be established through the use of multi-step processes in which the analyte sensor 110 authenticates itself to the receiving device and the receiving device authenticates itself to the analyte sensor 110. This is used to verify that the analyte sensor 110 is an authentic sensor compatible with the receiving device and that the receiving device is approved to receive data from the analyte sensor 110. For example, the receiving device can provide, to the analyte sensor 110, a valid certificate or token that has been digital signed by the manufacturer of the analyte sensor 110 or receiving device or the operator of the analyte monitoring system 100. The certificate or token can be validated by confirming that it has been digitally signed using a key associated with the appropriate manufacturer or operator. Similarly, the analyte sensor 110 can provide, to the receiving device, a valid certificate or token that has similar been digitally signed using a key associated with the appropriate manufacturer or operator. Each certificate or token can include a public key uniquely paired with a private key known to the device offering the certificate or token. The private key can also be established by the appropriate manufacturer or operator of the analyte monitoring system. Once a validated certificate or token is received, the device that offers the certificate or token can also prove that it has control of the private key. Proof of control can be established by decrypting selected information (e.g., a randomized or non-sequential value) that was encrypted using the public key included in the validated certificate. That information can be used to generate a shared symmetric authentication key which can be used for subsequent authentication and encryption.

If, at 510, the analyte sensor determines that it is operating in a connectable packet mode or a non-informational packet mode, then, at 525, the analyte sensor 110 prepares connection data 525 to be included in the data. As described herein, the connection data 525 can include data to facilitate a receiving device requesting and opening a communication session with the analyte sensor 110. The connection data 525 can include data specifying the protocol that can be used by the analyte sensor 110 to accept communication session requests.

In particular embodiments, the analyte sensor 110 can include either one or both of the connection data and analyte data in a single packet, e.g., while operating in a mixed packet mode (not illustrated in FIG. 5). For example, rather than determine which of the analyte data or the connection data to include, the decision at 510 can include determining whether or not to include the connection data, where every packet includes analyte data. The decision at 510 can include determining whether or not to include the analyte data where every packet includes connection data. In particular embodiments, the size allotted for the packet can be restricted to facilitate a reduction in transmission errors. The decision for which data to include (e.g., connection data or analyte data) can result from a programmed or dynamic determination of whether the analyte sensor 110 is to prioritize establishing connections or broadcasting packets with analyte data. Additionally or alternatively, other types of data can be optionally included the in the packet, and the decision at 510 can include determining whether or not to include the other types of data with the analyte data or connection data.

At 530, the analyte sensor 110 can prepare a data packet for broadcast. Depending on the operating mode determined at 510, the data packet can include analyte data, connection data, or other data. The analyte sensor 110 can prepare the selected data into a payload by arranging the collected data into a predetermined format that can be interpreted by a receiving device. The analyte sensor 110 can prepare a header for the payload that provides information to the receiving device so that it can determine how to interpret the payload. The analyte sensor 110 can validate the payload, such as by preparing one or more integrity check values for the payload. The analyte sensor 110 can prepare a header for the data packet which includes the payload to facilitate receiving devices in the environment of the analyte sensor 110 that are not configured to interpret the payload 110 in determining whether or not it will be able to use the data in the packet. In particular embodiments, such as where the analyte sensor 110 has been previously paired with a receiving device, as described herein, the header of the data packet can include identification data for the receiving device to direct the data packet to the receiving device.

At 535, the analyte sensor 110 can broadcast the data packet into an environment of the analyte sensor and/or transmit the data packet to one or more receiving devices within a communication range of the analyte sensor using a communication module of the analyte sensor. The environment can include multiple receiving devices (e.g., dedicated data receiving devices 120, multi-purpose data receiving device 130, user devices 140, etc.). Broadcasting can involve causing one or more transceivers (e.g., of the communication module 240 of the analyte sensor) to transmit a signal including the data packet in the environment using one or more communication channels that are specified by the communication protocol used by the communication module. The signal can be undirected, or not directed towards a particular receiving device in the environment. The communication channels can be reserved specifically for broadcast packets that can include connection information to facilitate the discovery and establishing of communication sessions between device.

At 540, for a determined period of time after broadcasting the data packet into the environment, the analyte sensor 110 can wait to receive an acknowledgement signal from a user device in the environment. As described herein, the environment of the analyte sensor 110 can include multiple receiving devices. Each of the receiving devices can receive the signal including the packet broadcast by the analyte sensor 110. Each receiving device can attempt to process the packet to determine whether it can or should use the data of the packet. For example, a receiving device can analyze the header of the data packet to determine if the data packet is directed to it or is undirected. If the data packet is not directed to another device, the receiving device can attempt to read the payload, for example, according to protocols set out in the header of the data packet. Where the payload is encrypted, the receiving device can attempt to decrypt the data packet using, for example, a stored encryption key. If the receiving device has a suitable decryption key, the receiving device can decrypt the payload and process the data included therein. For example, if the data of the payload includes analyte data, the receiving device can extract the analyte data for the subject from the decrypted data payload, process the extracted analyte data if needed, and output the analyte data to a user of the receiving device (e.g., provide the analyte data to a display of the receiving device, output one or more alerts or alarms based on the analyte data, upload the analyte data to a remote server, etc.). While outputting the extracted analyte data, the receiving device can indicate that the analyte data corresponds to highest priority data (e.g., most recently collected data, most urgent data according to the condition of the user, etc.).

After processing the data packet and payload, the receiving device can attempt to transmit an acknowledgement signal to the analyte sensor 110 to indicate that the payload of the data packet has been received. As an example, if the payload did not include connection data, the receiving device can broadcast an undirected packet that includes information interpretable by the analyte sensor 110. The undirected packet can include an encrypted payload, encrypted using the shared encryption key or scheme, that includes information for the analyte sensor 110 to confirm that the payload has been received. As another example, if the payload did include connection data, the receiving device can attempt to send the acknowledgement signal with a connection request, for example, using the connection protocol specified by the connection data.

If, at 540, the analyte sensor 110 receives an acknowledgement signal during the period of time during which the analyte sensor 110 is open to receiving the acknowledgement signal, the analyte sensor 110 can take further action based on the acknowledgement signal. For example, and as illustrated, at 545, the analyte sensor 110 can establish a communication session with the receiving device from which the acknowledgement signal was received. Establishing the communication session can include employing a multi-step device authentication and handshake, which can re-use the shared encryption key, and, additionally or alternatively, can use an additional communication session key to encrypt data exchanged between the analyte sensor 110 and receiving device in transmission.

At 550, the analyte sensor 110 can use the communication session to backfill analyte data with the receiving device. For example, the analyte sensor 110 can use the communication session to offload analyte data stored by the analyte sensor that has not previously been offloaded to one or more receiving devices for processing and/or reporting. As described herein, the analyte sensor can collect analyte data in a streaming manner, for example continuously or periodically, such as once per minute over a lifespan of the analyte sensor 110. The analyte sensor 110 can be disconnected or out of range from the receiving device. The analyte sensor 110 therefore stores an amount of analyte data (e.g., over a predetermined period of time). When the analyte sensor 110 reconnects with a receiving device, the analyte sensor can determine which data has not yet been offloaded, prepare that data for transmission over the communication session, and send the data to the receiving device. In particular embodiments, the analyte sensor 110 can, for example, delete all analyte data offloaded to a receiving device after it has been sent. Additionally or alternatively, the analyte sensor 110 can include sufficient memory to store the analyte data generated during its lifetime, particularly if the analyte sensor 110 is designed with a limited term of use. Additionally or alternatively, the analyte sensor 110 can preserve analyte data until space is required and overwrite certain segments of data first (e.g., the oldest, lowest priority, or least relevant data can be deleted or overwritten first).

In certain embodiments, the receiving device can determine the data to be backfilled by the analyte sensor 110 after the communication session is established by the analyte sensor 110. As an example, the receiving device can track the analyte data that has been received over time (e.g., over one or more communication sessions). As another example, the received analyte data can also be stored with a timestamp associated with when the analyte data was generated and/or the date and time associated with the analyte reading that was used to generate the analyte data. As another example, the received analyte data can be stored with a counter value uniquely attributed to a set of analyte data. For example, the counter value can be incremented with each additional reading of analyte data by the analyte sensor 110. The receiving device can determine, based on the timestamp and/or counter value that gaps in the stored analyte data are present. The receiving device can request the analyte sensor 110 to send the missing data, for example, by specifying the missing timestamp range and/or counter value range. In response, the analyte sensor 110 can identify the analyte data corresponding to the timestamp range and/or counter value range and transmit the analyte data to the receiving device. Once all analyte data specified by the range are provided the analyte sensor 110 and/or the receiving device, a confirmation that all specified data has been received is provided.

Additionally or alternatively, the analyte sensor 110 determines the data to backfill after establishing the communication session. When identifying the analyte data to backfill, the analyte sensor 110 can offload all stored data besides the highest priority data (which was included in the broadcast data packet). As another example, the analyte sensor can store a timestamp of the last time analyte data was offload from the analyte sensor 110. The analyte sensor can identify analyte data records between that timestamp and a current timestamp and transmit the identified analyte data. In particular embodiments, the backfill procedure can also use a data prioritization scheme (e.g., first in first out; last in first out; highest priority, most severe, other prioritization scheme, or a combination thereof).

As embodied herein, the analyte sensor 110 can maintain a record for the time elapsed since the analyte sensor 110 has received an acknowledgement signal from the user device and/or a time elapsed since a successful communication session has been completed. As an example, the analyte sensor 110 can associate a timestamp with an acknowledgment signal and upon receiving an acknowledgement signal, update the timestamp accordingly. Additionally, or alternatively, the analyte sensor 110 can maintain other records indicative of the status of the analyte data stored on the analyte sensor 110 and of the communication history between the analyte sensor 110 and the receiving device. As an example, the analyte sensor 110 can include a record of the time since the last communication session, the oldest analyte data record stored on the analyte sensor, etc. After the communication session is closed, the analyte sensor 110 can update the record associated with the time since the last communication session. Note that the analyte sensor 110 can store separate timestamps associated with acknowledgement signals and with communication sessions. By maintaining two timestamps (or other records indicative of the communication between the analyte sensor 110 and the receiving device), the analyte sensor 110 can track the presence of the receiving device in the environment of the analyte 110 and also track the historical completeness of the data offloaded from the analyte sensor 110. As described herein, the indication, or lack, of presence of the receiving device in the environment can be used by the analyte sensor 110 to alter its behavior to attempt to facilitate a connection.

If, at 540, the analyte sensor determines that it has not received an acknowledgement from a receiving device, the analyte sensor 110 can, at 555, determine whether the time since the analyte sensor 110 last received an acknowledgement satisfies a threshold time. Additionally or alternatively, analyte sensor 110 can determine whether a time since the last communication session or the age of the latest analyte record received satisfies a threshold. Other metrics can also be used to determine whether the analyte sensor 110 should alter its behavior to attempt to facilitate a connection. The metrics can indicate, for example, that there is a connection issue between the analyte sensor 110 and receiving device, that the analyte sensor 110 and receiving device have not been within a suitable proximity (e.g., a distance based on the communication range of the communication module 240 of the analyte sensor 110), that the receiving device is disabled, etc. In embodiments where connection data is included in only a subset of the packets sent by the analyte sensor 110, the inability to receive an acknowledgement signal can be a function of the analyte sensor 110 and receiving device not being within a requisite range at the appropriate time (e.g., when a packet including connection data is being broadcast).

If, at 555, the analyte sensor 110 determines that the time since the last acknowledgement or communication session does exceed the threshold, or other indicia of a potential communication issue are present, at 560, the analyte sensor 110 can be configured to alter its discoverability behavior to attempt to increase the probability of the receiving device receiving an appropriate data packet and/or provide an acknowledgement signal or otherwise reduce restrictions that can be causing an inability to receive an acknowledgement signal. Altering the discoverability behavior of the analyte sensor 110 can include, for example and without limitation, altering the frequency at which connection data is included the data packet, altering how frequently data packets are transmitted generally, lengthening or shortening the broadcast window for data packets, altering the amount of time that the analyte sensor 110 listens for acknowledgement signals after broadcasting, including directed transmissions to one or more devices (e.g., through one or more attempted transmissions) that have previously communicated with the analyte sensor 110 and/or to one or more devices on a whitelist of known or authorized devices, altering a transmission power associated with the communication module when broadcasting the data packets (e.g., to increase the range of the broadcast or decrease energy consumed and extend the life of the battery of the analyte sensor), altering the rate of preparing and broadcasting data packets, or a combination of one or more other alterations. Additionally, or alternatively, the receiving device can similarly adjust parameters relating to the listening behavior of the device to increase the likelihood of receiving a data packet including connection data. For example, after a threshold period of time elapses in which the receiving device does not receive a data packet, the receiving device can increase the amount of time or the frequency that the communication hardware of the receiving device is active and capable of receiving connection data (e.g., increasing the window of performing scans for data packets, in particular data packets including connection data). The analyte sensor 110 and receiving device can revert back to original settings if the attempts to increase discoverability are not successful after a specific period of time.

As embodied herein, the analyte sensor 110 can be configured to broadcast data packets using two types of windows. The first window refers to the rate at which the analyte sensor 110 is configured to operate the communication hardware. The second window refers to the rate at which the analyte sensor 110 is configured to be actively transmitting data packets (e.g., broadcasting). As an example, the first window can indicate that the analyte sensor 110 operates the communication hardware to send and/or receive data packets (including connection data) during the first 2 seconds of each 60 second period. The second window can indicate that, during each 2 second window, the analyte sensor 110 transmits a data packet every 60 milliseconds. The rest of the time during the 2 second window, the analyte sensor 110 is listening. The analyte sensor 110 can lengthen or shorten either window to modify the discoverability behavior of the analyte sensor 110. For example, the 2 second window can be expanded to 4 seconds (e.g., the first 4 seconds in each 60 second period) or shortened to 1 second (e.g., the first second in each 60 second period). As another example, the 60 second period can be lengthened (e.g., to conserve battery by reducing the amount of time the communication hardware is active) or shortened (e.g., to increase the likelihood that the communication hardware is active while a receiving device is in range). As another example, the 60-millisecond period can be lengthened or shortened.

In particular embodiments, the discoverability behavior of the analyte sensor can be stored in a discoverability profile, and alterations can be made based on one or more factors, such as the status of the analyte sensor 110 and/or by applying rules based on the status of the analyte sensor 110. For example, when the battery level of the analyte sensor 110 is below a certain amount, the rules can cause the analyte sensor 110 to decrease the power consumed by the broadcast process. As another example, configuration settings associated with broadcasting or otherwise transmitting packets can be adjusted based on the ambient temperature, the temperature of the analyte sensor 110, or the temperature of certain components of communication hardware of the analyte sensor 110. For example, when the temperature of the analyte sensor 110 or communication hardware thereof reaches a first threshold temperature (e.g., falls below the threshold or alternatively exceeds the threshold), the transmission power associated with the broadcast process can be lowered. Additionally, when the temperature reaches a second threshold temperature, the process of transmitting packets including connection data (e.g., advertising packets) can be paused altogether. The process can be restarting and/or the transmission power can be adjusted after the temperature reverts to satisfy another threshold. In addition to modifying the transmission power, other parameters associated with the transmission capabilities or processes of the communication hardware of the analyte sensor 110 can be modified, including, but not limited to, transmission rate, frequency, and timing. As another example, when the analyte data indicates that the subject is, or is about to be, experiencing a negative health event, the rules can cause the analyte sensor 110 to increase its discoverability to alert the receiving device of the negative health event. As the process 500 repeats multiple times, and can repeat throughout the operative life of the analyte sensor 110, alterations made to device discoverability can be propagated and affect future iterations of process 500.

If, at 555, the analyte sensor 110 determines that the time since last acknowledgement does not exceed the threshold, or that other indicia of a communication issue are not present, the analyte sensor returns to 505 where analyte data 110 continues to be collected and process 500 is repeated.

In particular embodiments, the analyte sensor 110 can receive an activation command from a particular user device. In particular embodiments, the activation command can be received over a first communication interface (e.g., NFC), while the analyte sensor 110 can broadcast packets over a second communication interface (e.g., BLE). The activation command can be received prior to the analyte sensor 110 beginning to collect analyte data, prior to the analyte sensor broadcasting data, or at any point during the process 500. The activation command can be used by the analyte sensor 110 and receiving device to affirmatively identify each device to the other. The activation command can include instructions relating to the broadcast or discoverability behavior of the analyte sensor 110. The instructions can affect, for example, the rate at which the analyte sensor prepares data (including but not limited to connection data, analyte data, or other data), the rate at which the analyte sensor broadcasts packets, whether the packets are directed to the particular user device or broadcast into the environment external to the analyte sensor, or other related parameters of the analyte sensor 110 performing the process 500 illustrated in FIG. 5. The activation command can further include instructions as to whether the process 500 should be used at all. For example, prior to receiving the activation command, the analyte sensor 110 can be configured to operate in a connectable packet mode and not transmit analyte data in packets (e.g., every packet includes connection data and not analyte data). Then, after receiving the activation command, the analyte sensor 110 can be configured to selectively operate in an informational packet mode to transmit analyte data in broadcast packets, which can be transmitted, for example, according to a predetermined schedule or a user-defined schedule, as described herein. As embodied herein, the analyte sensor 110 and the receiving device can use the activation command to initiate a first communication session during which analyte data (e.g., currently stored by the analyte sensor 110) is offloaded to the receiving device. This first communication session can be a preliminary step performed prior to the process 500 illustrated in FIG. 5. The analyte sensor 110 and the receiving device can close the communication session prior to the process 500.

As an example, a subject (or user of a receiving device) can instruct the receiving device to send an activation command to the analyte sensor 110 to cause the analyte sensor to enter a broadcast mode where current analyte data is sent via data packets according to the embodiments disclosed herein. The analyte sensor 110 can continue operating in the broadcast mode for a fixed or specified amount of time or until the analyte sensor 110 receives a deactivation command. As an example, an athlete running around a track can be wearing an analyte sensor 110 and desire for analyte data to be sent to a receiving device that is kept substantially stationary around the track (e.g., being held by a coach or other observer). In an ordinary (e.g., non-broadcast) mode, the analyte sensor 110 cannot establish a communication session with the receiving device to send pertinent analyte data to be output by the receiving device. Prior to the athlete beginning to run around the track, the athlete can cause the receiving device to issue an activation command to the analyte sensor 110 to initiate the broadcast mode and identify the receiving device. Then, while the athlete runs around the track, the analyte sensor 110 can broadcast analyte data to be received by the receiving device. The receiving device can process the analyte data, output current analyte data, issue alerts as to the health of the athlete using the embodiments disclosed herein to quickly send the highest-priority analyte data.

By inserting the analyte data into a data packet that is broadcast on or with communication channels ordinarily used only for the discovery and establishing of communication sessions, the analyte sensor 110, as embodied herein, can increase the speed and reliability that high priority or current analyte data is delivered to a user of a receiving device. Rather than waiting for a communication session to be established and the appropriate data to be offloaded from the analyte sensor 110 to the receiving device, the analyte sensor 110 and receiving device can exchange the most relevant data first and allow the user of the receiving device to review the most relevant data while the rest of the data stored on the analyte sensor 110 is offloaded. Thus, in addition to increasing the actual speed of delivery of the most relevant data, the user's perception of the speed of delivery of the rest of the data is also improved.

According to aspects of the disclosed subject matter, and as embodied herein, a sensor 110 can be configured to communicate with multiple devices concurrently by adapting the features of a communication protocol or medium supported by the hardware and radios of the sensor 110. As an example, the BLE module 241 of the communication module 240 can be provided with software or firmware to enable multiple concurrent connections between the sensor 110 as a central device and the other devices as peripheral devices, or as a peripheral device where another device is a central device. Although examples described herein reference BLE terminology, this is to balance brevity with a complete explanation of the techniques of this disclosure and should not be interpreted as a limiting to only a particular technology protocol or standard.

Connections, and ensuing communication sessions, between two devices using a communication protocol such as BLE can be characterized by a similar physical channel operated between the two devices (e.g., a sensor 110 and dedicated data receiving device 120). The physical channel can include a single channel or a series of channels, including for example and without limitation using an agreed upon series of channels determined by a common clock and channel- or frequency-hopping sequence. The common clock can be governed by a hardware clock of a controlling device in the pair. The channel- or frequency-hopping sequence can be determined based on unique attributes of one or more devices of the communication session, such as an identifier for the device (e.g., unique identifier, BLE identifier, etc.). Communication sessions can use a similar amount of the available communication spectrum, and multiple such communication sessions can exist in proximity. In certain embodiment, each collection of devices in a communication session uses a different physical channel or series of channels, to manage interference of devices in the same proximity. In certain embodiments, devices in the same proximity can share a channel through channel multiplexing schemes, such as those based on code-division or time-division algorithms.

To participate in multiple concurrent communication sessions, a BLE device, such as a sensor 110 and dedicated data receiving device 120 or multi-purpose data receiving device 130 switches between channels on a time-division multiplexing basis. In certain embodiments, to avoid collisions, a device can be prevented from controlling multiple communication sessions concurrency. In addition to being classified as controlling or participating devices in a communication session, devices can be categorized as advertisers or scanners. Advertisers are devices that invite connections with other devices by broadcasting connection packets on common communication channels. Devices that are able to interpret the connection packets can initiate communications with the advertiser. Scanners are devices that listen for connection packets transmitted by advertisers.

Figure 6A:
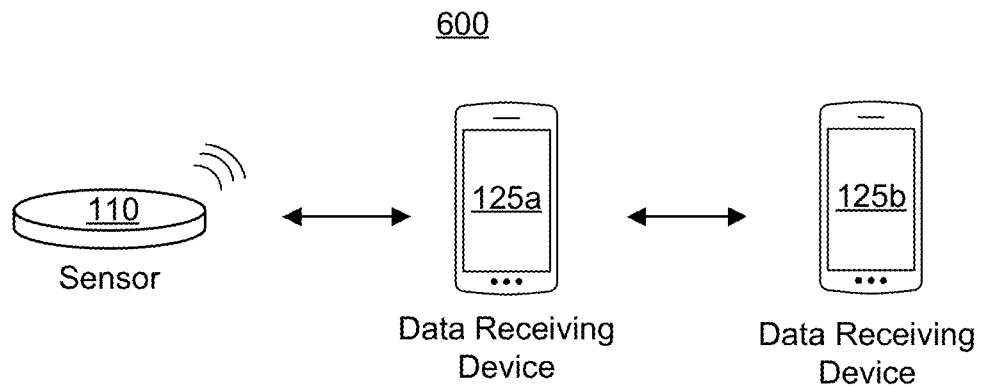
FIGS. 6A-6C are diagrams illustrating operating environments of an example analyte sensor with multiple data receiving devices.
Figure 6B:
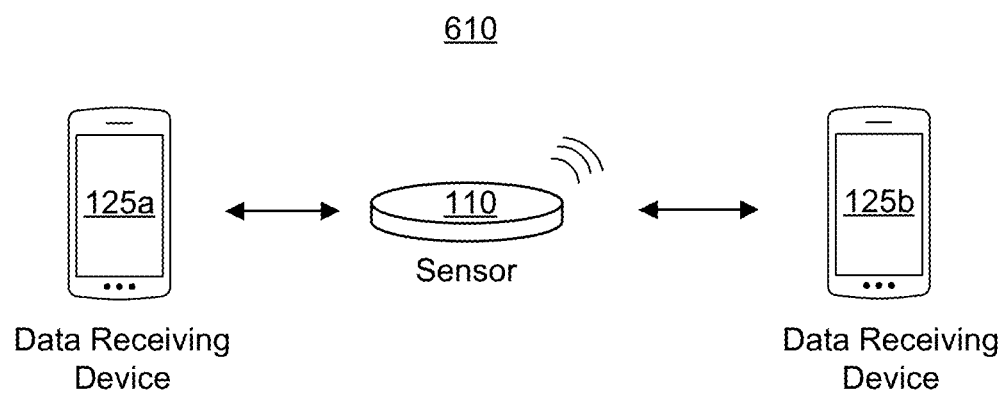
Figure 6C:
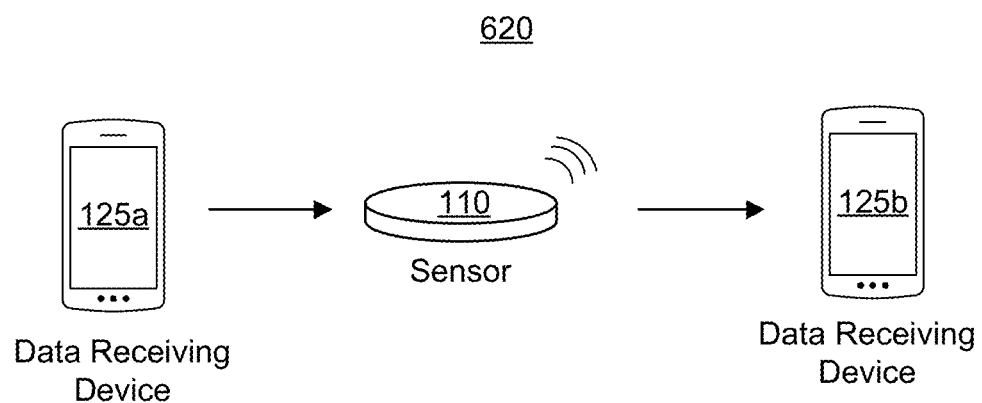

FIGS. 6A-6C are diagrams illustrating operating environments of an example analyte sensor with multiple data receiving devices. FIGS. 6A-6C illustrate environments in which the sensor 110 initiates or maintains concurrent communication sessions with both data receiving device 125a and data receiving device 125b. One or more of data receiving device 125a and data receiving device 125b can be a dedicated data receiving device 120 as described herein or a multi-purpose data receiving device 130 as described herein. As an example, data receiving device 125a can be a dedicated data receiving device 120 provided by the manufacturer of the analyte sensor 110 to facilitate monitoring of output of the sensor 110. Data receiving device 125b can be a second dedicated data receiving device 120, for example, associated with a different user from the user or available as a backup device (e.g., in case the user loses the data receiving device 125b). As another example, data receiving device 125b can be multi-purpose data receiving device 130 in a different form factor from data receiving device 125a, such as a smartphone, tablet, smartwatch, wearable fitness monitor, or a health device such as an insulin pump or insulin, cardiac device, wearable health monitor, or other device that would benefit from the availability of output provided by the analyte sensor 110. In particular embodiments, one or more of data receiving device 125a or data receiving device 125b can be a home monitor or server relay configured to provide output from the analyte sensor 110 to a remote device such as a user device 140 or remote server 150. In this way, using the techniques described herein, and using a short-range communication protocol such as a BLE or high-frequency Wi-Fi, the analyte sensor 110 can provide output to both a local data receiving device 125a and secondary remote device concurrently. The techniques described herein can be used with data receiving device 125a and 125b that include medical functions and non-medical functions. In particular, the techniques described herein can be used with data receiving devices 125a without medical functions that are being used for evaluative purposes, such as consumer fitness monitors, whether stand-alone or incorporated into other, multi-purpose devices. Although only two data receiving devices are illustrated, the environments can be extended to encompass situations where more than two data receiving devices communicate with the sensor 110, where multiple sensors 110 communicate, or where multiple data receiving devices communicate with each other.

FIG. 6A illustrates an environment 600 in which the sensor 110 communicates with data receiving device 125b through data receiving device 125a. In this environment, data receiving device 125a acts as a relay between sensor 110 and data receiving device 125b, allowing the other devices to piggyback on a connection between the sensor 110 and data receiving device 125a and data receiving device 125a and data receiving device 125b. The data receiving device 125a is a trusted third-party or middleman device between the sensor 110 and data receiving device 125b. The data receiving device 125a can act as a gateway or router of the data between the sensor 110 and data receiving device 125b. For example, the data receiving device 125a can perform security checks to authenticate the sensor 110 and data receiving device 125b (and in some cases, as described herein, can enable further communications between sensor 110 and data receiving device 125b directly).

The data receiving device 125a can assist one or more of the sensor 110 and data receiving device 125b with preparing requests for the other device and responding to requests issued by the other device. As an example, the data receiving device 125a can receive a request from the data receiving device 125b for the sensor 110 and interpret or translate the request into a format usable by the sensor 110. In translating the request for the sensor 110 on behalf of the data receiving device 125b, the data receiving device 125a acting as a router for the requests can enable the sensor 110 and data receiving device 125b to operate more efficiently or expand their functionalities with minimal additional overhead. Additionally, the data receiving device 125a can present a device-agnostic interface for both devices, increasing the interoperability of the sensor 110 and data receiving device 125b.

In particular embodiments, one or more of sensor 110 and data receiving device 125b are not aware of the other device in the environment 600. For example, the sensor 110 can provide output data to the data receiving device 125a as part of normal operations. The data receiving device 125b can request access to data corresponding to output from the sensor 110. However, the data receiving device 125b can request the data without knowing the origin of the data, such as the identity of sensor 110 in the environment 610. This arrangement can be advantageous where, for example, data receiving device 125a is a central hub or common device to systems involving the sensor 110 and data receiving device 125a and sensor 110 and data receiving device 125b. Furthermore, through this system, the privacy and security of the user and other potential users of the sensor 110 and data receiving device 125b can be protected because the identity of the device can be protected. Even if the sensor 110 and data receiving device 125b are aware of the other device, data receiving device 125a can process output and data from sensor 110 on behalf of data receiving device 125b. For example, the sensor 110 can output raw values to the data receiving device 125a and data receiving device 125a can apply one or more algorithms to the data so that it can more effectively be used by data receiving device 125b. Additionally, the data receiving device 125a can generate data or instructions for display by data receiving device 125b. As an example, data receiving device 125a can generate instructions to modify a user interface of data receiving device 125b based on data from sensor 110. In such an example, data receiving device 125b does not directly access the data from sensor 110, but instead accesses the user interface instructions or passes the data directly through to the user interface for review by a user.

FIG. 6B illustrates an environment 610 in which the sensor 110 communicates with data receiving device 125a and data receiving device 125b through individual communication sessions. In environment 610, the sensor 110 can maintain more than one concurrent communication session. Maintaining more than one concurrent communication session can involve, in certain embodiments, receiving requests from each of the data receiving device 125a and data receiving device 125b, determining the identity of the requesting device (e.g., whether the request was issued by the data receiving device 125a or data receiving device 125b), determining the appropriate response (which can, for example and without limitation, be dependent on the identity of the requesting device), and transmitting the response in a format understood by the requesting device. In certain embodiments, security measures can be taken to reduce the risk of crosstalk, interference, or data snooping between the data receiving device 125a and data receiving device 125b (e.g., data receiving device 125a unintentionally interfering with communications between the sensor 110 and data receiving device 125b or data receiving device 125b attempting to access communications between sensor 110 and data receiving device 125a). These security measures can include the use of unique encryption keys to secure data packets sent between sensor 110 and data receiving device 125a or data receiving device 125b, unique communication channels or channel-hopping procedures for communication sessions between sensor 110 and data receiving device 125a or data receiving device 125b, and other similar measures.

In particular embodiments, the sensor 110 identifies the device that has issued a request based on the communication medium of the request. For example, the sensor 110 and data receiving device 125a can have agreed upon use of a particular communication channel for the sensor 110 to receive requests and the sensor 110 and data receiving device 125b can have agreed upon use of a different communication channel or the sensor 110 to receive requests. Then, the sensor 110 can assume that a request received on the particular communication channel is from the data receiving device 125a. In particular embodiments, the sensor 110 identifies the device that has issued a request based on the request itself. For example, the request can include information to identify the device that has issued the request. A request from the data receiving device 125a can include a unique identifier for the data receiving device 125a while a request from the data receiving device 125b can include a unique identifier for the data receiving device 125b. Upon receiving the request, the sensor 110 reviews the information provided in the request to identify the device that has issued the request. The sensor 110 can store a library or mapping of unique identifiers to data receiving devices. Using this mapping, requests from the data receiving device 125a and data receiving device 125b can avoid including plaintext identifiers. As an example, during an initiation stage of a pairing between the sensor 110 and data receiving device 125a, the sensor 110 and data receiving device 125a can agree on an identifier for the data receiving device 125a or a scheme for determining an identifier for the data receiving device 125a. Upon receiving a request, the sensor 110 can reference the mapping to positively determine that the data receiving device 125a has issued the request. A third party without access to the mapping would be unable to determine the identity of the data receiving device 125a.

FIG. 6C illustrates an environment 620 in which the sensor 110 acts as a relay for the data receiving devices 125a and 125b by, for example, receiving input or commands from data receiving device 125a and, in response, transmitting data to data receiving device 125b. Sensor 110 therefore facilitates indirect communication between data receiving device 125a and data receiving device 125b. In environment 620, the data receiving device 125a and data receiving device 125b can operate without direct knowledge of the other device. In some embodiments, data receiving device 125a and data receiving device 125b can be incompatible or unable to communicate directly. However, because the sensor 110 is able to create secured communication sessions with each, the sensor 110 is able to facilitate the devices exchange information. As an example, data receiving device 125a can be a connected medical device such as an insulin pump and data receiving device 125b can be a smartphone configured with a software application to facilitate monitoring of output from sensor 110. As embodied herein, data receiving device 125a and data receiving device 125b would not be configured to communicate. However, it can be advantageous for the software application to be made aware of medical interventions initiated by the insulin pump. Therefore, the insulin pump (data receiving device 125a) can inform the sensor 110 when it is dispensing insulin and the sensor 110 can relay this information to the software application (data receiving device 125b) so that the smartphone can record the event directly, rather than, for example, inferring the existence of the event indirectly. As demonstrated, a sensor 110 configured to operate in an environment such as environment 620 can increase the interoperability of data receiving device 125a and data receiving device 125b.

Figure 7:
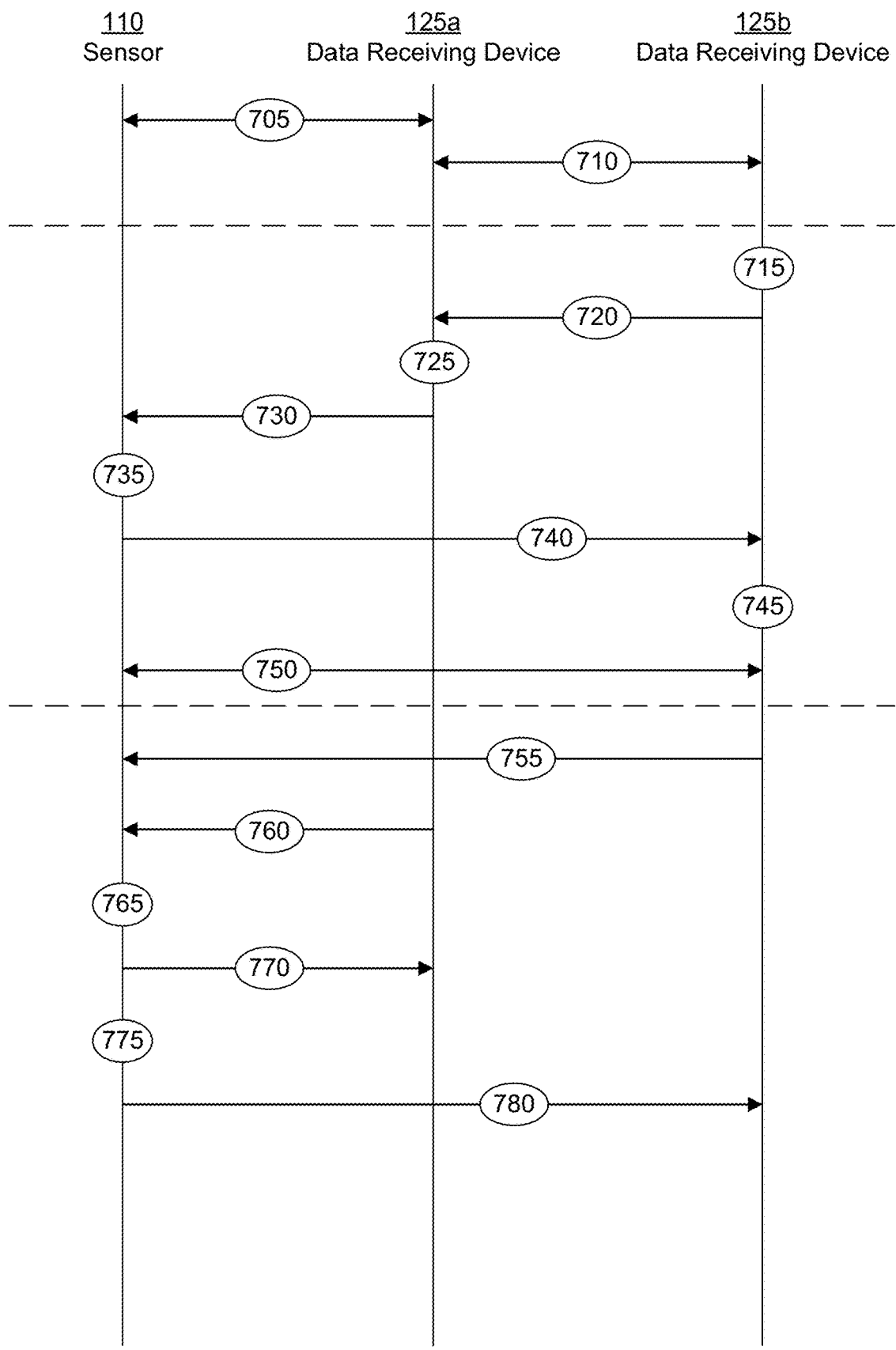
FIG. 7 is a diagram illustrate an example operational flow of an analyte sensor according to the disclosed subject matter.

FIG. 7 illustrates a process of establishing a communication session between a sensor 110 and a data receiving device 125b using data receiving device 125a and transmitting analyte data pursuant to the communication session.

At 705, the data receiving device 125a and sensor 110 establish a connection or communication session. In particular embodiments, the sensor 110 and data receiving device 125a can use a first communication protocol for short-range wireless communication, such as Bluetooth or BLE. The connection can be performed though a pairing process supported by the communication protocol. As an example, the sensor 110 can be configured to periodically broadcast connection packets to facilitate other devices discovering and connecting to the sensor 110. The data receiving device 125a can receive a connection packet and, using the information contained therein, establish a connection and mutual authentication with the sensor 110. As another example, the data receiving device 125a can use a second communication protocol to establish the communication session between the sensor 110 and data receiving device 125a. For example, the data receiving device 125a can, upon being brought within a suitably close range, initiate an NFC communication session to exchange information allow the sensor 110 and data receiving device 125a to pair and mutually authenticate.

At 710, the data receiving device 125a and data receiving device 125b establish a connection or communication session. For purpose of illustration and not limitation, as described herein, the data receiving device 125a and data receiving device 125b can be different instances of the same kind of data receiving device (e.g., two data receiving devices comprising a multi-purpose data receiving device 130 configured with a downloaded library or software application), two separate data receiving devices owned by the same user (e.g., a multi-purpose data receiving device 130 and a smartwatch), two separate data receiving devices owned by a user wearing the sensor 110 and by an authorized monitor such as a parent, coach, or medical caretaker, a data receiving device for monitoring the output of the sensor 110 and a data receiving device for acting based on the output of the sensor 110, such as a connected medical device like an insulin pump or pen, or a connected exercise equipment like a treadmill, fitness bike, or a variety of other suitable combinations. The data receiving device 125a and data receiving device 125b can communicate using one or more short- or medium-range communication protocols.

At 715, the data receiving device 125b receives a request to connect with the sensor 110. The request to connect with the sensor 110 can be initiated by a user of the data receiving device 125b. The request can indicate that that user wishes to use the data receiving device 125b to monitor the output of the sensor 110 or to pair the data receiving device 125b and sensor 110 to enable additional functionality of the data receiving device 125b. In some embodiments, the request can be initiated automatically in response to a user indicating that they have an available sensor 110 for use with the data receiving device 125b. In response to receiving the request, the data receiving device 125b determines that it is unable to connect directly with the sensor 110 and must use an existing connection between the data receiving device 125a and sensor 110 to establish the connection with the sensor 110.

At 720, the data receiving device 125b sends a connection request to the data receiving device 125a. In response to determining that it will use the existing connection between the data receiving device 125a and sensor 110 to establish a connection with the sensor 110, the data receiving device 125b prepares a connection request indicating to the data receiving device 125a the request to use the existing connection. For example, the data receiving device 125b can include in the request information identifying the data receiving device 125b (e.g., an address of the data receiving device 125b, a BLE handle for the data receiving device 125b), the user of the data receiving device 125b, or the sensor 110 (e.g., a unique identifier for the user, or a public authentication key prepared by or for the data receiving device 125b or sensor 110), information identifying how the sensor 110 and data receiving device 125b will initiate the connection (e.g., a communication channel or channel-hopping protocol to be used by the devices), and other information to validate and act on the request.

At 725, the data receiving device 125a receives the connection request and prepares a connection request for the sensor 110. In certain embodiments, the data receiving device 125a can perform steps to validate the request and authenticate the data receiving device 125b and user of the data receiving device 125b. For example, the data receiving device 125a can interrogate the information included in the connection request from the data receiving device 125b. The data receiving device 125a can provide the information to a remote server 150 associated with the sensor 110. The remote server 150 can confirm the validity of the information and take other security-related actions to, for example, determine that the data receiving device 125b is not attempting to reuse expired credentials or establish a connection with an incorrect sensor 110. Additionally or alternatively, the data receiving device 125a can be configured to perform operations to validate the connection request.

At 730, the data receiving device 125a sends the connection request to the sensor 110. After validating the connection request from the data receiving device 125b, the data receiving device 125a can repackage the information from the connection request from the data receiving device 125b for use by the sensor 110. With the connection request, the data receiving device 125a can include information asserting or confirming the validity of the data receiving device 125b and the connection request. The sensor 110 can use the information asserting the validity of the data receiving device 125b to confirm the request and streamline the process of initiating the connection between the sensor 110 and the data receiving device 125b.

At 735, the sensor 110 receives the connection request from the data receiving devices 125a. From the connection request, the sensor 110 identifies the data receiving device 125b (e.g., using a BLE handle for the data receiving device 125b included in the connection request) and a mechanism to use to initiate the connection. For example, the connection request can include a security algorithm type to be used for the connection or a communication channel or channel-hopping scheme to use to facilitate the connection. The sensor 110 can determine if the data receiving device 125b has previously initiated a connection with the sensor 110 to expedite the connection procedure. For example, the sensor 110 can store a mapping table of devices with which it has connected. The mapping table can include identifiers or handles for the devices and a locally assigned identifier (e.g., an index in the table) generated by the sensor 110 to act as a shorthand to reference the device in the future. If the identifier for the data receiving device 125b is found in the table, or if the data receiving device 125b has provided valid locally assigned identifier, then the sensor 110 can conclude that the data receiving device 125b can communicated with the sensor 110 before. If the identifier for the data receiving device 125b does not appear in the mapping table, the sensor 110 can generate a new entry for the data receiving device 125b and proceed to establish a pairing with the data receiving device 125b.

At 740, the sensor 110 sends a connection acknowledgement to the data receiving device 125b. The connection acknowledgement can indicate to the data receiving device 125b that the sensor 110 has received the connection request. The connection acknowledge can further identify the sensor 110 to the data receiving device 125b. The connection acknowledgement can further include information that will be used to initiate a mutual authentication between the sensor 110 and data receiving device 125b. As an example, the connection acknowledgement can include a public key for the sensor 110 or a shared authentication key generated based on information included in the connection request from the data receiving device 125b.

At 745, the data receiving device 125b receives the connection acknowledgement. In response to receiving the connection acknowledgement, the data receiving device 125b confirms that the connection acknowledgement is from the correct sensor 110. For example, the connection acknowledge can include information identifying the sensor 110 which the data receiving device 125b compares against information stored by the data receiving device 125b identifying the sensor 110. In certain embodiments, the data receiving device 125b confirms the identity of the sensor 110 by presenting information identifying the sensor 110 that has responded to the connection request to a user of the data receiving device 125b. The user confirms the identity of the sensor 110 by responding to a prompt at the data receiving device 125b.

At 750, the sensor 110 and data receiving device 125b can conduct a mutual authentication. Based on information exchanged between the sensor 110 and data receiving device 125b (for example, in the connection request and connection acknowledgement), the sensor 110 and data receiving device 125b can independently generate a shared secret. The shared secret can be based on public keys and private keys of the sensor 110 and the data receiving device 125b as applied to a piece of random data that is agreed-upon by the sensor 110 and the data receiving device 125b. The shared secret can be selected such that only a device with both a public key of the sensor 110 and data receiving device 125b and a private key (e.g., a non-shared key) of at least one of the sensor 110 or data receiving device 125b would be able to generate the shared secret. Using the shared secret, the sensor 110 and data receiving device 125b can verify the identity of the other device by confirming that the other device has access to the private key corresponding to a shared public key. After confirming the identity of the other device, the sensor 110 and data receiving device 125b can generate a mutual encryption value or scheme for subsequent communication sessions between the sensor 110 and data receiving device 125b.

After performing the mutual authentication, the sensor 110 and data receiving device 125b are ready to initiate a secured communication session. In particular embodiments, the sensor 110 can store an identifier for the data receiving device 125b that facilitates the sensor 110 recognizing connection requests from the data receiving device 125b. For example, the sensor 110 can store, in local storage 230 or memory 220, a mapping between the identifier for the data receiving device 125b and the mutual encryption value.

With reference to 715-750 of FIG. 7, these actions can be performed when a data receiving device 125b is unable to connect directly to a sensor 110 on its own. For example, data receiving device 125b can have user-input capabilities such that a user uses data receiving device 125a to control data receiving device 125b. In cases where the data receiving device 125b can initiate a connection to the sensor 110 directly, the process of establishing and communication session between the sensor 110 and data receiving device 125b follows the standard procedure and can be performed without data exchanged between data receiving device 125a and data receiving device 125b to facilitate the request.

At 755, the data receiving device 125b initiates a request for data from the sensor 110 and at 760, the data receiving device 125a initiates a request for data from the sensor 110. Although the requests are shown in a particular order, this is for illustrative purposes only, and the data receiving device 125a can initiate a request for data from the sensor 110 prior to the data receiving device 125b. In particular embodiments, the request from the data receiving device 125a or data receiving device 125b can be initiated periodically. For example, the data receiving device 125a and data receiving device 125b can be configured to transmit a request for data addressed to the sensor 110 according to a preset schedule (e.g., once every 60 seconds, once every 10 seconds, twice every second, etc.). The schedule can be determined based on the computational abilities of the device as well as factors such as the power or battery level of the device. The schedule can be further determined based on the amount of data to be requested or the amount of time since the requesting device was last able to retrieve data from the sensor 110. In some embodiments, the schedule is determined between the sensor 110 and each of the data receiving device 125a and data receiving device 125b independently, that is data receiving device 125a and data receiving device 125b are not aware of the scheduled time for the other. In other embodiments, the schedule is determined with input from data receiving device 125a and data receiving device 125b, allowing the two devices to negotiate on the schedule and avoid interfering with each other's requests. This approach, though adding some computational complexity and requiring the devices to, in some way, be aware of each other, allows for load balancing for the sensor 110 and minimizes the appearance of parallel requests and processing.

In particular embodiments, the request from the data receiving device 125a or data receiving device 125b can be initiated upon the data receiving device 125a or data receiving device 125b coming into communicative range of the sensor 110. For example, the data receiving device 125a and data receiving device 125b can be configured to send polling requests to determine the identity of nearby devices. Additionally or alternatively, the sensor 110 can be configured to periodically send advertising or connection requests to all nearby devices. Upon receiving an advertising request, the data receiving device 125a or data receiving device 125b can initiate the request for data.

At 765, the sensor 110 processes the requests for data from the data receiving device 125a and the data receiving device 125b. In particular embodiments, to process the requests for data, the sensor 110 first confirms the authentication of the data receiving device 125a or data receiving device 125b. As an example, the sensor 110 first identifies which device sent a request. As an example, and as described above, the requests can each include information to identify the requesting device, such as a unique or local identifier (e.g., BLE handle or a shorthand for the handle managed internally by the sensor 110) for the data receiving device 125a or data receiving device 125b. The sensor 110 then confirms that the requesting device has permission or has otherwise been authenticated to request data from the sensor 110. If the device does not have the requisite permission, then the request can be either rejected or converted to a request to establish a connection directly with the sensor 110. Determining that the requesting device has permission can include, by way of example, comparing the identifier for the requesting device with identifiers stored by the sensor 110 as a result of previous connection requests and identifying a set of permissions granted to that device. Once the identity and the permissions for the requesting device are established, the sensor 110 proceeds to determine how to response to the requests.

In particular embodiments, the requests for data from the data receiving device 125a and data receiving device 125b can include information to indicate what type of data each device is requesting. As an example, the sensor 110 can process and store data related to levels of specified analytes detected in the user. The data can be stored according to a key or queue system in which the data can be easily indexed to a specific event or a period of time. As such, the data related to the levels of the specified analytes can be stored with a timestamp unique to each data record. The requests for data from the data receiving device 125a and data receiving device 125b can be associated with a key representing a range of analyte data requested by the device. As an example, the request can include a timestamp, range of timestamp, unique identifier, or life count associated with data records requested by the requesting device. In response to each request, the sensor 110 can retrieve the requested data from its storage 230.

In particular embodiments, the sensor 110 can track which data has been provided to which data receiving devices. As an example, each entry comprising analyte levels (or other sensed levels) can be annotated with information including the identity of data receiving devices that have requested and receiving that data, a timestamp or count associated with the request, and a timestamp or a count associated with the data receiving device receiving a response to the request. In such cases, unless specified otherwise, a request for data from a data receiving device 125 or data receiving device 125b can be interpreted as a request to provide all missing data. In preparing information to provide to the data receiving device, the sensor 110 can determine which data records have not yet been provided to the requesting device.

Once the appropriate records have been identified, the sensor 110 packages the data into a response to the request for data. As an example, the sensor 110 prepares a response message include a payload comprising the requested data (or data otherwise identified for the data receiving device that initiated the request). The sensor 110 can receive requests and send responses asynchronously, and the sensor 110 can further note which data receiving device the response message is intended for. As such, the data requested by the data receiving device 125a and data receiving device 125b can be different. As an example, the data receiving device 125a can be updated more frequently, so individual responses are smaller. As another example, the data receiving device 125b can request only subsets of data associated with specified times (e.g., during nights or after meals), so the data receiving device 125b does not request all data from the sensor 110.

At 770, the sensor 110 responds to the request from the data receiving device 125a. To respond to the request, the sensor 110 transmits the response packet prepared for the data receiving device 125a to the data receiving device 125a using, for example, an agreed communication scheme between the two devices or using the establish communication session.

At 775, the sensor 110 processes the request for data from the data receiving device 125b. Although illustrated as a separate step, much of the processing for processing the request from the data receiving device 125b can be similar to processing the request from the data receiving device 125a, the difference being that the sensor 110 identifies data for the data receiving device 125b and prepares the packet for reception by the data receiving device 125b. At 780, the sensor 110 responds to the request from the data receiving device 125b.

As discussed, the sensor 110 can respond to the request in a variety of orders, such as in the same order as received, according to a pre-established priority (e.g., request from data receiving device 125a always take priority over requests from data receiving device 125b), based on the time since the request has been received, based on a schedule (e.g., pending requests from data receiving device 125a are responded to on every $10^{th}$ second of the minute and pending requests from data receiving device 125b are responded to on every $40^{th}$ second of the minute), the size of the request, the size of the pending response, and other suitable response schemes.

Data receiving device 125a and data receiving device 125b can continue to initiate requests from the sensor 110 to maintain an active communication session. In certain embodiments, communication session can time out through inactivity to preserve the battery life of the sensor 110 and possibly data receiving device 125a and data receiving device 125b. Data receiving device 125a and data receiving device 125b therefore can, while they are within a communication range of the sensor 110, initiate requests to the sensor 110 to keep the connection active. If the connection is deactivated through inactivity, data receiving device 125a or data receiving device 125b can initiate a new communication session with the sensor 110 using the shared secret or and existing authentication key or can request and generate a new authentication key using the techniques described herein.

To further manage the battery life of the sensor 110, the sensor 110 can alter aspects of the hardware operation. As an example, when the sensor 110 expects to communicate with two or more data receiving devices in concurrent communication sessions, the sensor 110 monitors additional channels correlating with the communication session information set by the data receiving devices. This additional monitoring uses more battery life. To perform additional communication sessions with additional devices, the sensor 110 uses even more battery life. The monitoring on additional channels involves certain hardware processes that can be dynamically altered based on the number of potential communication sessions that the sensor 110 is monitoring. As an example, the sensor 110 can adjust the number of connection packets sent as advertising packets, adjust the amount of time each transmission is active, adjusting the number of transmission cycles or the rate of iteration of the transmission cycles, adjust the amount of time in an active receiving mode or the frequency of transition to the active receiving mode, or make other dynamic adjustments as appropriate to balance the ability of the sensor 110 to initiate and maintain communication sessions with the adjust battery life of the sensor 110.

The communication module 240 of the sensor 110 can be configured to handle or manage the bi-directional communication link between the sensor 110 and a receiver 120. The communication module 240 can include communication circuitry configured to transition between a sleep state, a partial awake state, and a fully awake state. For example, when in the fully awake state, the communication circuitry can be configured to execute tasks and actions associated with a communications protocol startup (CPS) instruction set 221 that can include an advertisement scanning related (ASR) instruction subset 222 and a non-ASR instruction subset 223. The communication circuitry, when in the partially awake state, is configured to execute the ASR instruction subset 222. The ASR instruction subset 222 can include transmitting advertising notices 224 over one or more channels according to a wireless communications protocol (e.g., BLE) and scanning the one or more channels for a connection request from a receiver or other device. Alternatively, the advertising notices 224 can be stored in the communication module 240. Conversely, when a connection request is not received, the communication circuitry can return to the sleep state without performing actions or tasks associated with the non-ASR instruction subset 223 of the CPS instruction set 221. In the example of FIG. 2, the CPS instruction set 221 can be stored in memory 220 and/or 243, which is accessed by the microcontroller 210 and/or processor 246 of the communication module 240, respectively. The CPS instruction set 221 can provide the wireless protocol syntax for the microcontroller 210 and/or processor 246 to assemble data packets, advertisement notices, connection requests, connection responses, establish communication links, and/or partition data received from the receiver 120. Additionally or alternatively, the CPS instruction set 221 can be stored in ROM, RAM, firmware or other memory on the communication module 240 or sensor 110 generally. As a further example, the CPS instruction set 221 can be "stored" through settings of hardware circuitry within the communication module 240 or sensor 110.

In an embodiment, the communication circuitry of the communication module 240, when executing the CPS instruction set 221 with the BLE peripheral application in the fully awake state, can utilize a first amount of power. Also, when executing the ASR instruction subset 222 with the BLE peripheral application in the partially awake state, the CPS instruction set 221 can utilize a second amount of power that is less than the first amount of power. The CPS instruction set 221 can include more tasks and actions that take a longer period of time and more power to implement in comparison to the tasks and actions of the ASR instruction subset 222. For example, the second amount of power and amount of time, to implement the ASR instruction subset, can be between 40%-80% of the first amount of power and time to implement the entire CPS instruction set. As another example, the second amount of power and amount of time, to implement the ASR instruction subset, can be between 50%-65% of the first amount of power and time to implement the entire CPS instruction set.

The communication module 240 includes a receiver that scans for connection requests from the receiver 120. As described herein, the communication module 240 can be controlled by the microcontroller 210 and can support one or more wireless communication protocols while communicating with the receiver 120, such as Bluetooth low energy (e.g., using BLE module 241), Bluetooth, Medical Implant Communication Service (MICS), Wi-Fi, cellular communication, or other similar protocols. The communication module 240 can include a transmitter, receiver, and/or a transceiver. Optionally, the communication module 240 can be electrically coupled to an antenna.

The microcontroller 210 is coupled to the memory 220 by a suitable data/address bus 296. The memory 220 can store the programmable operating parameters used by the microcontroller 210. The microcontroller 210 can modify the operating parameters, as required, in order to customize the operation of sensor 110 to suit the needs of a particular wearer. The memory 220 can also store data sets (raw data, summary data, historical data, trends, histograms, etc.), such as the levels of one or more analytes over a period of time (e.g., 1 hour, 24 hours, 7 days, 1 month). The data sets stored in the memory 220 can be selected and packaged into data packets (e.g., data packet 400) and sent to receiving devices (e.g., receiver 120). The memory 220 can store instructions to direct the microcontroller 210 to analyze the electrical signals from the sensing hardware 260 to identify characteristics of interest and derive values for storage and presentation.

In addition, the memory 220 stores CPS instruction set 221. The CPS instruction set 221 can be loaded in the memory 220 at the time of manufacture, at the time of activation, at the time of installation, or throughout operation. For example, during a communication session, a receiver 120 can provide updates to the CPS instruction set stored in the memory 220. The CPS instruction set 221 includes the ASR instruction subset 222 and non-ASR instruction subset 223. The ASR instruction subset 222 can include instructions related to at least two of the following: expiration of a wake-up timer; processor startup; initialization of a transmit circuit; formation of advertising data packets; transmission of advertising data packets; scanning one or more channels for a connection request from another device (e.g., receiver 120); and validating or denying an incoming connection request. The non-ASR instruction subset 223 can include instructions related to at least two of the following: initialization of a random-access memory (RAM) segment/block; initialization of sensing hardware 260; initialization of an operating system service; and initialization of the CPS instruction set 221. In one embodiment, the ASR instruction subset 222 does not include instructions related to at least two of the following: initialization of a random-access memory (RAM) segment/block; initialization of sensing hardware 260; initialization of an operating system service; and initialization of the CPS instruction set 221.

In accordance with embodiments herein, advertisement schedules included in the CPS instruction set 221 can balance fast advertisement at low power and low sensitivity in conjunction with slow advertisement at high power and high sensitivity. The balance can be taken to afford quick communications and longer range automatic connections for remote monitoring. As explained herein, once a connection is made between the receiver 120 and the sensor 110, the communication module 240 can set the transmit power and receive sensitivity to a desired communications session level (e.g., high) for a duration of the communication session. The transmit power and receive sensitivity can be set to the desired communications session level regardless of whether the connection was established using short or long range advertisement, thereby affording a desired communications distance during an active communications session. For example, if a subject wanted to force a communication session, the patient can hold the receiver 120 close to the sensor 110 in order to begin the communications session in accordance with short range advertisement. Then, once the connection is made, the communication module 240 adjusts the transmit power and receive sensitivity to a communications session level (e.g., max power settings), thereby allowing the subject to leave the receiver 120 on a table or otherwise out of hand without experiencing any disruption of the communication session.

Additionally or alternatively, one or more separate advertisement schedules included in the CPS instruction set 221 can be stored in the memory 220 to be used in connection with individual corresponding receivers 120. For example, when an sensor 110 initially begins communicating with a particular receiver 120, the receiver 120 can download a corresponding advertisement schedule included in the CPS instruction set 221, along with the instruction to utilize the advertisement schedule included in the CPS instruction set 221 until otherwise instructed. Subsequently, the sensor 110 can communicate with another receiver 120 that downloads a corresponding new advertisement schedule included in the CPS instruction set 221, along with an instruction to utilize the new advertisement schedule included in the CPS instruction set 221 until otherwise instructed. As a further example, the sensor 110 can update the advertisement schedule included in the CPS instruction set 221 throughout operation, such as based upon the success rate at which communications links are established, based on delays when establishing communications links and the like.

The operating parameters of the sensor 110, including but not limited to the CPS instruction set 221, can be non-invasively programmed into the memory 220 through the communication module 240 in bi-directional wireless communication with the receiver 120. In some embodiments, the communication module 240 can be controlled by the microcontroller 210 and receives data for transmission from the microcontroller 210. The communication module 240 allows data from the sensing hardware 260 and status information relating to the operation of the sensor 110 (as contained in the microcontroller 210, memory 220, or storage 230) to be sent to the receiver 120 through an established bi-directional communication link. The communication module 240 also allows the receiver 120 to program new parameters and advertisement schedules for the sensor 110.

The communication module 240 transmits one or more advertisement notices or advertisement packets 400 on one or more advertisement channels. Each advertisement channel is a point to multipoint, unidirectional, channel to carry a repeating pattern of system information messages such as network identification, allowable RF channels to establish the communication link, or the like that is included within the advertisement notice. As described herein, in certain embodiments, the advertisement notice can include analyte data 425 in addition to connection data 420 within its payload 410. The advertisement notice can be repeatedly transmitted after a set duration or an advertisement interval based on an advertisement schedule stored in the memory 220 until the communication link is established with the receiver 120.

Figure 8:
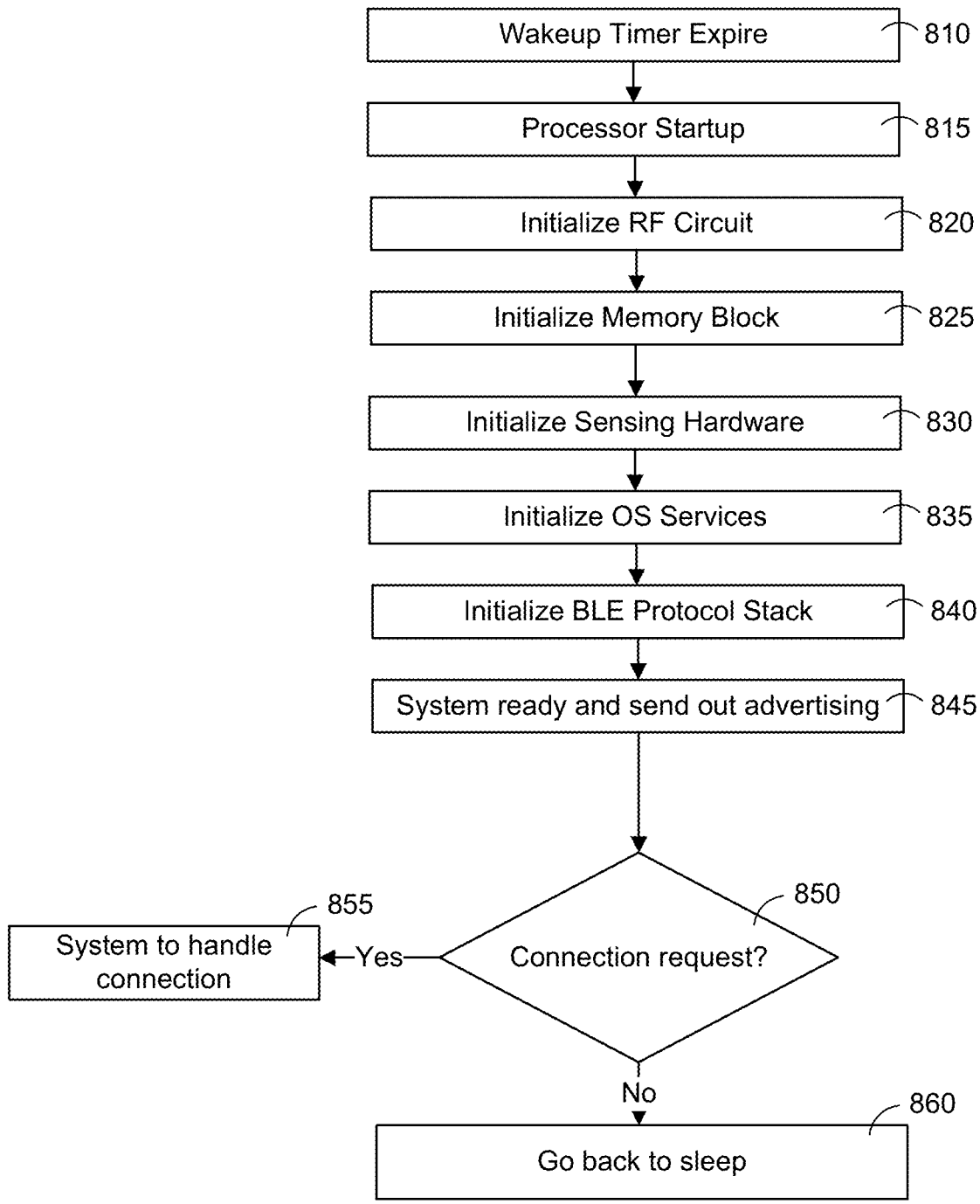
FIG. 8 illustrates an example of initialization blocks of a BLE peripheral application in a fully awake state.

FIG. 8 illustrates an example set of initialization operations, which may be performed, for example, by a BLE peripheral application upon entering in a fully awake state. Although described in the context of the BLE communication protocol, similar operations can be performed when the sensor 110 is configured to operate using other communication protocols. The illustrated process represents a non-limiting example of a set of initialization actions or tasks for a BLE peripheral application operating while communication circuitry of a communication module 240 is in a fully awake state.

At 810, the wakeup timer expires and the BLE peripheral application is activated. For example, the sensor 110 can wake up from a predetermined sleep interval. This interval can occur in between connection or advertising events. These connection or advertising events can be controlled by the timing control circuitry 211 as shown in FIG. 2. The timing control circuitry 211 can include a sleep clock. When the wakeup timer expires at the end of the sleep interval, the timing control circuitry 211 can process the current connection or advertising event and establish a new sleep interval using the sleep clock.

At 815, a processor startup routine commences. For example, the startup module 212 can be utilized to control a boot process of the processor. For example, after the timing control circuitry 211 has determined a wakeup interval for the sensor 110, the startup module 212 can include or access ROM (e.g., memory 220 or 243) or non-volatile Flash memory with boot code utilized to control the boot process. The ROM can load the boot process. The boot process can include power on, operating system load, and transfer of control to the operating system. For example, subsequent to a power on activity initiated by a user, condition, timer, or other stimulus, a routine can be executed to ensure that the device drivers are functioning properly. Any issues encountered can halt the boot process. Each device in a boot list can load its own routine to ensure proper communication between the devices and the startup module 212. After a successfully completed routine, the operating system 213 can be loaded.

At 820, the communication circuitry of the communication module 240 is initialized. The communication module 240 is controlled by the microcontroller 210 and can support one or more wireless communication protocols while communicating with the receiver 120, such as BLE, Bluetooth, MICS, and/or the like. The communication module 240 transmits one or more advertisement notices on one or more advertisement channels. Each advertisement channel is a point to multipoint, unidirectional, channel to carry a repeating payload, which may include, connection data 420 including system information messages such as network identification, allowable channels to establish the communication link, or the like. The advertisement notice can be repeatedly transmitted after a set duration or an advertisement interval based on an advertisement schedule stored in the memory 220 until the communication link is established with the receiver 120.

At 825, the memory 220 is initialized. For example, operating parameters can be loaded into certain memory locations and/or registers. The memory 220 can store programmable operating parameters used by the microcontroller 210. The memory 220 also stores data sets, such as data generated from or by the sensing hardware 260 or processed by the microcontroller 210 from the data generated from or by the sensing hardware 260. The memory 220 can also store instructions to direct the microcontroller 210 to analyze the data generated from or by the sensing hardware 260 to identify characteristics of interest or priority and derive values for presentation to the receiver 120. Additionally, the memory 220 stores one or more advertisement schedules included in the CPS instruction set 221.

At 830, the sensing hardware 260 can be initialized. For example, the sensing hardware 260 can require a short warmup period before usable data can be retrieved from or by the sensing hardware 260. During initialization, this warmup period can be enforced or voltage can be applied to the sensing hardware 260 to expedite the warmup period. Once the sensing hardware 260 is ready, data or other values can be retrieved from the sensing hardware 260. For example, a current value for levels of one or more particular analytes can be recorded and processed by the microcontroller 210.

At 835, if the sensor 110 supports an operating system 213 as a base operating layer, operating system services are initialized. After a successful completed BIOS, the operating system 213 can commence to run applications or other functions of the sensor 110. The operating system 213 can comprise various application programs for collecting and analyzing biological signals such as analyte levels.

At 840, the BLE protocol stack 230 is initialized. The protocol stack 230 can include a host and controller comprising multiple layers utilized for communication.

At 845, the BLE peripheral application transmits one or more advertising notices. The protocol stack 230 controls the time at which the advertising notices are sent. The Link Layer (LL) of the controller of the protocol stack 230 can control the radiofrequency (RF) state of the device, which can include the advertising state. The scan request and scan response activities occur during the advertising intervals of both applications.

At 850, the sensor 110, e.g., via the BLE peripheral application, determines whether a connection request has been received (e.g., from a receiver 120 in the environment of the sensor 110). If there are no connection requests, the process ends and the IMD goes back to sleep as illustrated at 860. Alternatively, if a connection request is received, the process proceeds to 855.

At 855, the sensor 110, e.g., via BLE peripheral application, analyzes the content of the connection request, such as to determine if the connection request was sent by an authorized receiver 120. If the connection request is sent by an authorized receiver 120, the sensor 110 and receiver 120 can exchange additional information to initiate a communications session. The receiver 120 and sensor 110 can connect, and the sensor 110 can send data gathered by the sensor 110 (e.g., through the sensor hardware 260). As an example, the sensor 110 can backfill data not yet transmitted to the receiver 120 either automatically or based on a request from the receiver 120. At this point in the process, the sensor 110 is fully awake.

Figure 9:
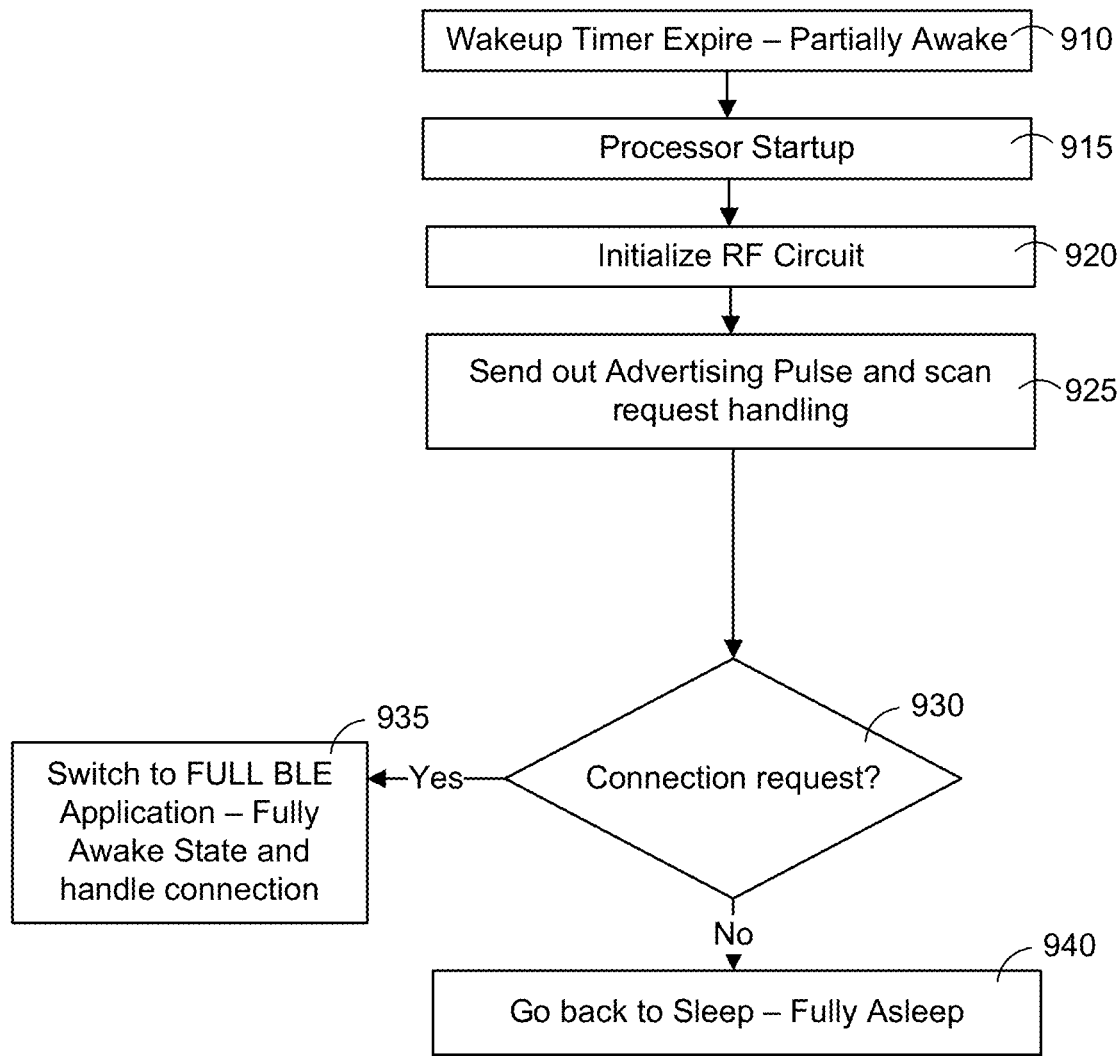
FIG. 9 illustrates an example of initialization blocks of a BLE advertising application in a partially awake state.

FIG. 9 illustrates an example of initialization operations of a process 900 for a BLE peripheral application while in a partially awake state. The BLE peripheral application operates in a partially awake state until full power is required and is shown from a firmware perspective that interacts with the Bluetooth Low Energy system on a chip (SoC). Although illustrated in the context of the BLE communication protocol, a similar application and process can be used for the sensor 110 when operating using other communication protocols.

At 910, the wakeup timer expires and activates a partially wake (low power) BLE application. For example, the sensor 110 can wake up from a predetermined sleep interval. This interval can occur in between connection or advertising events. These connection or advertising events can be controlled by the timing control circuitry 211 as shown in FIG. 2. The timing control circuitry 211 can include a sleep clock. When the wakeup timer expires at the end of the sleep interval, the timing control circuitry 211 can process the current connection or advertising event and establish a new sleep interval using the sleep clock. At this point in the process, the sensor 110 is partially awake.

At 915, the processor startup routine is implemented similar to the routine described in connection with the operations at 810. At 920, the communication circuitry of the communication module 240 is initialized similar to the routine described in connection with the operations at 815.

The low power BLE application operating using the process 900 skips the steps from 825 through 840 as shown in the BLE peripheral application in a fully awake state. The low power BLE application does not necessarily initialize the memory block, the sensing hardware 260, or the full BLE protocol stack during this portion of the process. This change in process shortens the time necessary for the processor and hardware blocks to be active during each advertising opportunity, conserving battery power.

At 925, the BLE peripheral application constructs and sends one or more advertising notices. In certain embodiments, the advertising notices are preformed and include payloads 410 with only connection data 420. In certain embodiments, the advertising notices are generated to further include most recent or highest priority analyte data 425, which may be encrypted before inclusion in the advertising packet payload 410.

At 930, the BLE peripheral application determines whether a connection request was received. The connection request can be received from one or more receiving devices (e.g., receiver 120) in the environment of the analyte sensor 110. If no connection request is received, the process ends and the sensor 110 goes back to sleep as illustrated at 940. Alternatively, if a connection request is received, the process proceeds to 935. At 935, the BLE peripheral application analyzes the connection request and initiates a communications session if appropriate. At this point in the process, the sensor 110 begins to perform the skipped operations to transition into the fully awake state.

Figure 10:
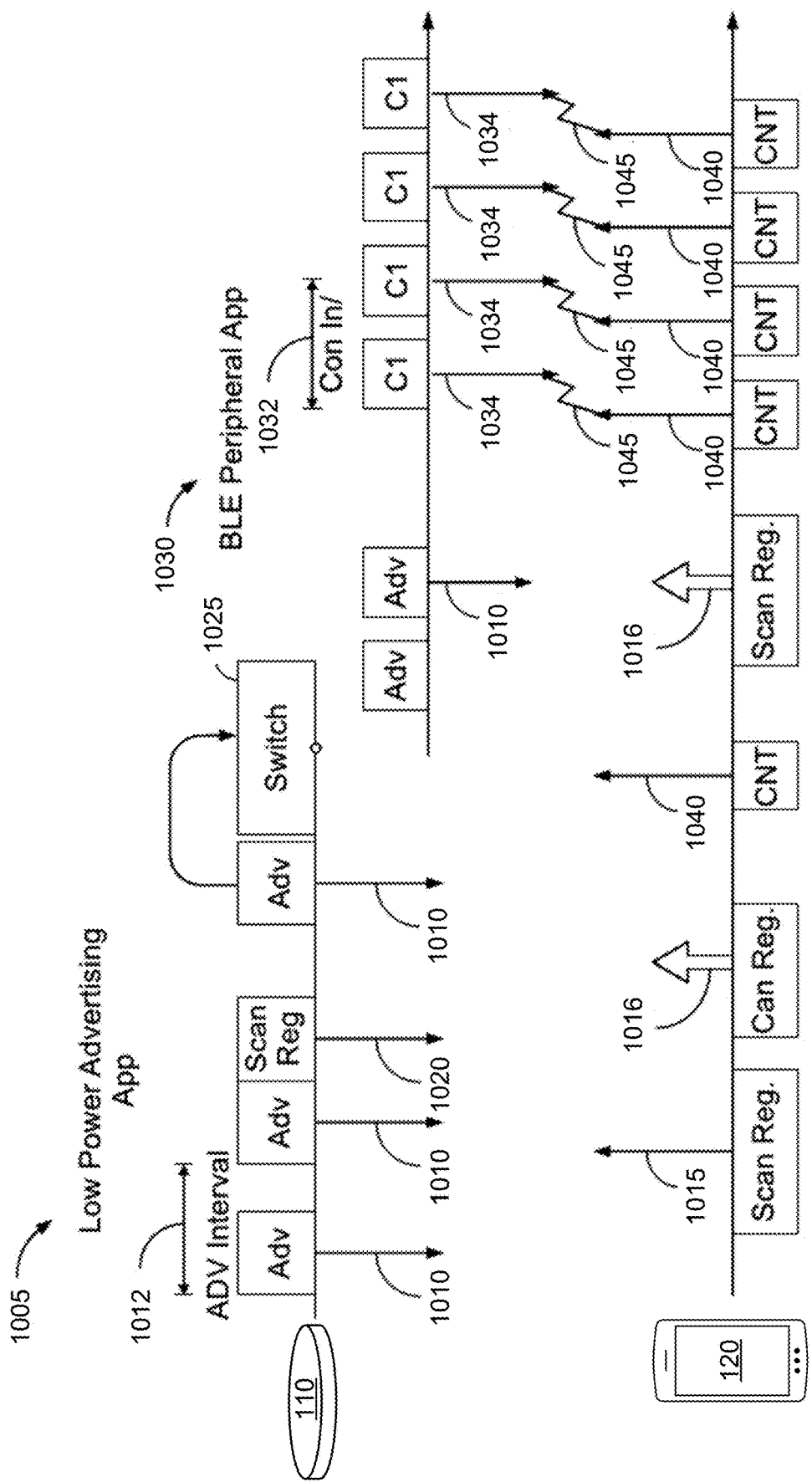
FIG. 10 illustrates an example of an application switch sequence between a BLE advertising application in a partially awake state and a BLE advertising application in a fully awake state in accordance with embodiments herein.

FIG. 10 illustrates an example of an application switching sequence between a Low Power (partially awake) Advertising Application and a (fully awake) BLE peripheral Firmware Application. The sensor 110 transmits advertising notices 1010 at advertising interval 1012 during different advertising periods while in the partially awake state. The receiver 120 transmits a scan request 1015 to request a connection to the sensor 110. Once the scan request 1015 is received by the sensor 110, a scan response 1020 can be sent to the receiver 120. If the scan response 1020 indicates that the receiver 120 is approved for a connection 1040 to the sensor 110 and subsequent communication 1045, a switching operation 1025 is initiated and the partially awake advertising application 1005 switches to the fully awake advertising 1030 when a connection request 1035 is received. The partially awake advertising application 1005 hands the process over to the fully awake advertising application 1030. The scan request 1015 can be processed by analyzing identifying features of the receiver 120.

When the fully awake advertising application 1030 takes control, the memory block 220 is initialized (operation 825 in FIG. 8) in the fully awake advertising application. For example, program instructions or parameters can be loaded into RAM, registers or other memory locations. Various indices into the memory are initialized. In addition, sensing hardware 260 is initialized (operation 830). In addition, the operating system services can be initialized (operation 835) and the BLE protocol stack 230 can be fully initialized (operation 840). Thereafter, a communications session is established.

Figure 11:
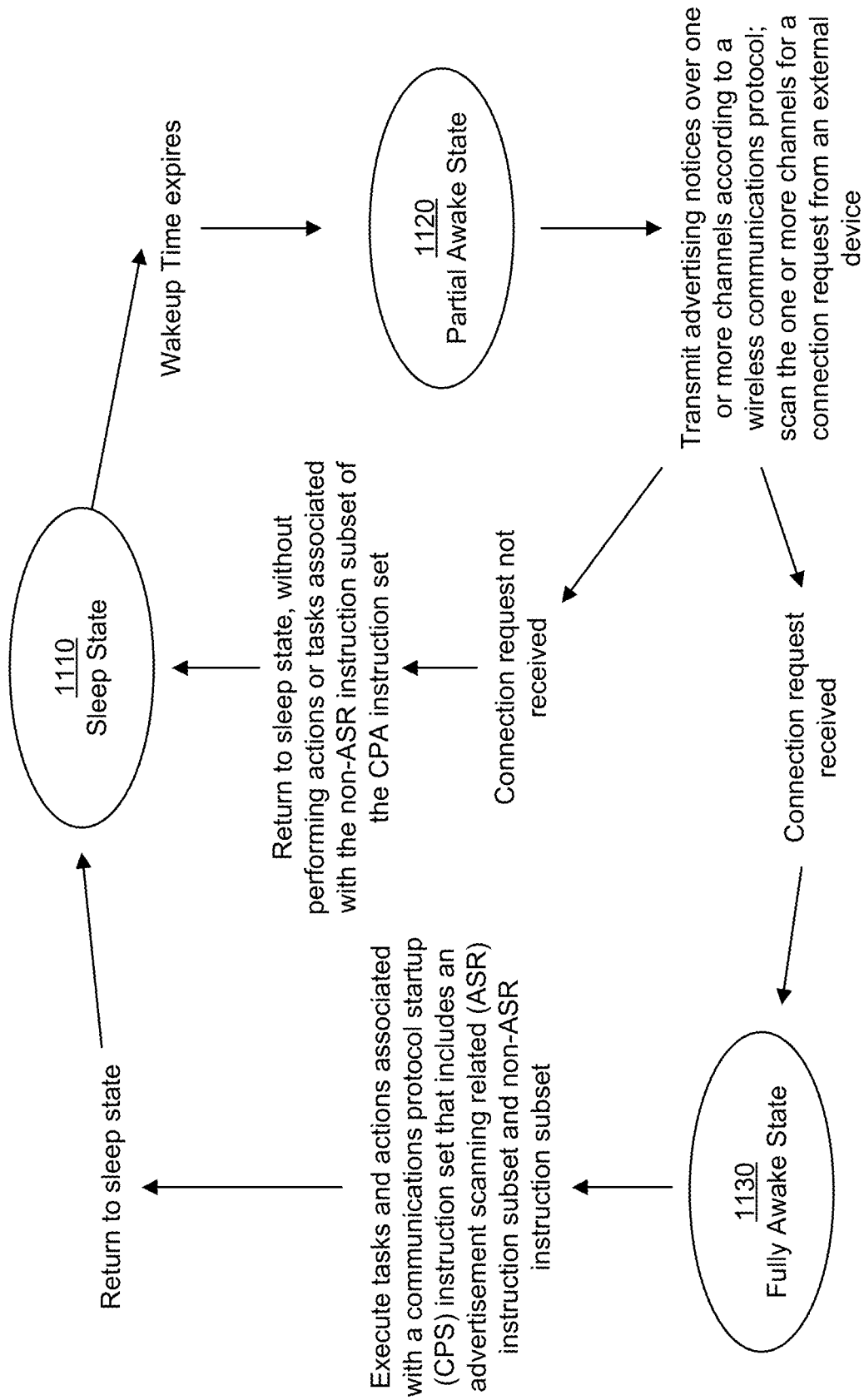
FIG. 11 is a state machine diagram illustrating states of communication circuitry configured in accordance with embodiments herein.

FIG. 11 is a state machine diagram illustrating states of a communication circuitry of a sensor 110, configured in accordance with the embodiments disclosed herein. Initially, the communication circuitry begins in a sleep state 1110. The communication circuitry remains in the sleep state until a wakeup timer expires. Once the wakeup timer expires, the communication circuitry transitions from the sleep state to a partially awake state 1120, which also can be referred to as a low power advertising state. During the partially awake state, the communication circuitry is configured to transmit advertising notices over one or more channels according to a wireless communications protocol and scan the one or more channels for a connection request from a receiver.

If a connection request is received from a receiver 120, the connection circuitry can be configured to transition to a fully awake state 1130. The fully awake state can also be considered a full power or standard advertising state. During the fully awake state, the communication circuitry is configured to execute tasks and actions associated with a communications protocol startup (CPS) instruction set that includes an advertisement scanning related (ASR) instruction subset and a non-ASR instruction subset. After completing the required handling duties, the communication circuitry can return to the sleep state until the next wakeup timer expires.

If, however, a connection request is not received, the communication circuitry can return directly to sleep state 1110, without performing actions or tasks associated with the non-ASR instruction subset of the CPS instruction set.

When the communication circuitry executes the CPS instruction set while in the fully awake state, the sensor 110 utilizes a first amount of power. When executing the ASR instruction subset while in the partially awake state, the sensor 110 utilizes a second amount of power that is less than the first amount of power. The complete CPS instruction set includes more tasks and actions that take a longer period of time and more power to implement versus the limited set of task and actions of the ASR instruction subset.

The communication circuitry can include additional or alternative hardware or firmware, in which case the ASR instruction subset can include instructions related to at least two of the following: expiration of a wake-up timer; processor startup; initialization of a transmit circuit; transmission of advertising data packets; scanning one or more channels for a connection request from a receiver 120; or validating or denying an incoming connection request. In certain embodiments, the ASR instruction subset can not include the non-ASR instruction subset. The non-ASR instruction subset can include instructions related to at least two of the following: initialization of a random-access memory (RAM) segment or block; initialization of an external instrument component; initialization of an operating system service; or initialization of a communications protocol stack.

Not illustrated is the manufacture of the devices used in the analyte monitoring system 100 illustrated in FIG. 1, including the analyte sensor 110, dedicated data receiving device 120, as well as software or application programming interfaces that can be used by or with the remote server 150, multi-purpose data receiving devices 130, and other user devices 140. The manufacturer can choose to provide the information and programming necessary for the devices to securely communicate through secured programming and updates (e.g., one-time programming, encrypted software or firmware updates, etc.). For example, the manufacturer can provide information that can be used to generate encryption keys for each device, including secured root keys for the analyte sensor 110 and optionally for the dedicated data receiving device 120 that can be used in combination with device-specific information and operational data (e.g., entropy-based random values) to generate encryption values unique to the device, session, or data transmission as need. These encryption keys can be used, for example, to validate data transmitted from external devices (e.g., dedicated data receiving devices 120, multi-purpose data receiving devices 130, user device 140, etc.) to analyte sensors 110.

The manufacturer can imbue each analyte sensor 110 with a unique identifier ("UID") and other identifying information, such as an identifier for the manufacturer, identifier for the communication module and manufacturer, or any other suitable identifying information for the sensor or sensor components. As an example, the UID can be derived from sensor-unique data, such as from a serial number assigned to each ASIC 200 embodied in the analyte sensor 110 by the ASIC vendor, from a serial number assigned to a communication module 240 embodied in the analyte sensor 110 by a communication module vendor, from a random value generated by the sensor manufacturer, etc. Additionally or alternatively, the UID can also be derived from manufacturing values including a lot number for the analyte sensor 110 or its components, a day, date, or time of manufacturer of the analyte sensor 110 or its key components, the manufacturing location, process, or line of the sensor or its key components, and other information that can be used to identify when and how the sensor was manufactured. The UID can be accompanied by encryption keys and several generated random values that are also unique to each analyte sensor 110. Similar processes can be used to establish the secure identity of a receiving device, such as a dedicated data receiving device 120.

As the data collected by the analyte sensor 110 and exchanged between the analyte sensor 110 and other devices in the analyte monitoring system 100 pertain to medical information about a user, the data is highly sensitive and can be beneficial to be protected. Analyte data associated with a user is sensitive data at least in part because this information can be used for a variety of purposes, including for health monitoring and medication dosing decisions. In addition to user data, the analyte monitoring system 100 can enforce security hardening against efforts by outside parties to reverse-engineering. The security architecture described herein can include various combinations of control features described herein, including, but not limited to the protection of communication between devices, the protection of proprietary information within components and applications, and the protection of secrets and primary keying material. As embodied herein, encryption and authentication can be used as exemplary technical controls for providing protective features. As embodied herein, the various components of the analyte monitoring system 100 can be configured compliant with a security interface designed to protect the Confidentiality, Integrity and Availability ("CIA") of this communication and associated data. To address these CIA concerns, security functions can be incorporated into the design of the hardware and software of the analyte monitoring system 100.

As embodied herein, to facilitate the confidentiality of data, communication connections between any two devices (e.g., an analyte sensor 110 and receiving device) can be mutually authenticated prior to transmitting sensitive data by either device. Communication connections can be encrypted using a device-unique or session-unique encryption key. As embodied herein, the encryption parameters can be configured to change with every data block of the communication.

As embodied herein, to protect the integrity of data, encrypted communications or unencrypted communications between any two devices (e.g., an analyte sensor 110 and receiving device) can be verified with transmission integrity checks built into the communications. As an example, as described herein, data transmitted by an analyte sensor 110 to a receiving device through a communication session can be validated by the receiving device with transmission integrity checks prior to the receiving device acting on or storing the data. As another example, and as described herein, payloads of broadcast data packets can include integrity check values. Furthermore, data written to a memory of the analyte sensor 110 can be verified or validated with integrity checks prior to execution. As embodied herein, session key information, which can be used to encrypt the communication, can be exchanged between two devices after the devices have each been authenticated. Integrity check values can include, for example, an error detection code or error correction code, including as an example and not by way of limitation, non-secure error-detecting codes, minimum distance coding, repetition codes, parity bits, checksums, cyclic redundancy checks, cryptographic hash functions, error correction codes, and other suitable methods for detecting the presence of an error in a digital message.

As embodied herein, minimum distance coding includes a random-error correcting code that provides a strict guarantee on number of detectable errors. Minimum distance coding involves choosing a codeword to represent a received value that minimizes the Hamming distance between the value and the representation. Minimum distance coding, or nearest neighbor coding, can be assisted using a standard array. Minimum distance coding is considered useful where the probability that an error occurs is independent of the position of a given symbol and errors can be considered independent events. These assumptions can be particularly applicable for transmissions over a binary symmetric channel.

Additionally or alternatively, as embodied herein, a repetition code relates to a coding scheme that repeats bits across a channel to guarantee that communication messages are received error-free. Given a stream of data to be transmitted, the data divided into blocks of bits. Each block is transmitted and re-transmitted some predetermined number of times. An error is detected if any transmission of the repeated block differs.

In addition, or as a further alternative, as embodied herein, a checksum is a value relative to a message or stored block of data based on a modular arithmetic sum of message code words of a fixed word length. The checksum can be directed from the entire block of data or subset thereof. Checksums are generated using a checksum function or cryptographic hash function that is configured to output significantly different checksum values (or hash values) for minor changes to the targeted message. A parity bit is a bit added to a group of bits in transmission to ensure that the counted number of certain bits in the outcome is even or odd. For example, the parity bit can be used to ensure that the number of bits with value 0 is odd. A parity bit can then detect single errors or a repeating fixed number of errors. A parity bit can be considered a special case of a checksum.

As embodied herein, to further reduce or prevent unauthorized access to the devices of the analyte monitoring system 100, root keys (e.g., keys used to generate device-unique or session-unique keys) can optionally not be stored on the analyte sensor 110 and can be encrypted in storage by the remote server 150 or on other device having more computing power than the analyte sensor 110 (e.g., dedicated data receiving device 120). As embodied herein, the root keys can be stored in an obfuscated manner to prevent a third-party from easily accessing the root keys. The root keys can also be stored in different states of encryption based on where in the storage they are stored. As embodied herein, to facilitate the availability of data, analyte sensor 110 operations can be protected from tampering during service life, in which the analyte sensor 110 can be configured to be disposable, for example and as embodied herein by restricting access to write functions to the memory 220 via a communication interface (e.g., BLE and NFC). The sensor can be configured to grant access only to known devices (e.g., identifier by a MAC address or UID) or only to devices that can provide a predetermined code associated with the manufacturer or an otherwise authenticated user. Access to read functions of the memory 220 can also be enforced, including for example where the read function attempts to access particular areas of the memory 220 that have been designated secure or sensitive. The analyte sensor 110 can further reject any communication connection request that does not complete authentication within a specified amount of time to safeguard against specific denial of service attacks on the communication interface including attempted man-in-the-middle (MITM) style attacks. Furthermore, the general authentication and encryption design, described herein, can support interoperable usage where analyte sensor 110 data can be made available to other "trusted" data receiving devices without being permanently bound to a single device.

As embodied herein, the devices, including analyte sensor 110 and receiving devices in the environment of the analyte sensor 110 (e.g., dedicated data receiving device 120, multi-purpose data receiving device 130, user device 140, etc.) can each employ a variety of security practices to ensure the confidentiality of data exchanged over communication sessions and facilitate the relevant devices to find and establish connections with trusted endpoints. As an example, the analyte sensor 110 can be configured to proactively identify and connect with trusted local-area, wide-area, or cellular broadband networks and continuously verify the integrity of those connections. The analyte sensor 110 can further deny and shut down connection requests if the requestor cannot complete a proprietary login procedure over a communication interface within a predetermined period of time (e.g., within four seconds). For example and without limitation, such configurations can further safeguard against denial of service attacks.

As embodied herein, the analyte sensor 110 and receiving device can support establishing long-term connection pairs by storing encryption and authentication keys associated with other devices. For example, the analyte sensor 110 or data receiving device can associate a connection identifier with encryption and authentication keys used to establish a connection to another device. In this manner, the devices can re-establish dropped connections more quickly, at least in part because the devices can avoid establishing a new authentication pairing and can proceed directly to exchanging information via encrypted communication protocols. After a connection is successfully established, the device can refrain from broadcasting connection identifiers and other information to establish a new connection and can communicate using an agreed channel-hopping scheme to reduce the opportunity for third-parties to listen to the communication.

Data transmission and storage integrity can be actively managed using on-chip hardware functions. While encryption can provide a secure means of transmitting data in a tamper-proof manner, encryption and decryption can be computationally expensive processes. Furthermore, transmission failures can be difficult to differentiate from attacks. As described previously, a fast, hardware-based error detection code can be used for data integrity. As an example, as embodied herein, an appropriately-sized error detection code for the length of the message (e.g., a 16-bit CRC) can be used, although other suitable hardware-based error detection codes can be used in accordance with the disclosed subject matter. Programming instructions that access, generate, or manipulate sensitive data can be stored in memory blocks or containers that are further protected with additional security measures, for example encryption.

As embodied herein, the analyte monitoring system 100 can employ periodic key rotation to further reduce the likelihood of key compromise and exploitation. A key rotation strategy employed by the analyte monitoring system 100 can be designed to ensure backward compatibility of field-deployed or distributed devices. As an example, the analyte monitoring system 100 can employ keys for downstream devices (e.g., devices that are in the field or cannot be feasibly provided updates) that are designed to be compatible with multiple generations of keys used by upstream devices. Additionally, and according to the subject matter herein, keys can be securely updated by invalidating memory blocks including out-of-date keys which are then replaced with data written to new memory. Rotation of keys can be initiated by the manufacturer or the operator of the analyte monitoring system 100. For example, the manufacturer or operator of the analyte monitoring system 100, can generate a new set of keys or define a new set of procedures for generating keys. During manufacture of sensors 110 that are intended to use the new set of keys, the manufacturer can propagate the new set of keys to newly manufactured sensors 110. The manufacturer can also push updates to deployed devices in communication with the remote server 150 to extend the new set of keys or set of procedures for generating keys to the deployed devices. As a further alternative, key rotation can be based on an agreed-upon schedule, where the devices are configured to adjust the keys used according to some time- or event-driven function.

In addition to the specific embodiments claimed below, the disclosed subject matter is also directed to other embodiments having any other possible combination of the dependent features claimed below and those disclosed above and in the attached figures. As such, the particular features disclosed herein can be combined with each other in other manners within the scope of the disclosed subject matter such that the disclosed subject matter can be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An analyte monitoring device comprising:
   one or more processors,
   an analyte sensor,
   a communication module, and
   one or more memories communicatively coupled to the one or more processors, the analyte sensor, and the communication module, and comprising instructions executable by the one or more processors to configure the one or more processors to perform operations comprising:
   generating sensor data indicative of an analyte level measured by the analyte sensor, wherein at least a portion of the analyte sensor is transcutaneously positioned in contact with a bodily fluid of a subject;
   initializing the communication module using an advertisement scanning related instruction set, wherein the advertisement scanning related instruction set is a subset of a communications protocol startup instruction set including the advertisement scanning related instruction set and a non-advertisement scanning related instruction set;
   causing the communication module to issue one or more advertising packets;
   receiving a connection request from a receiving device;
   completing initialization of the communication module using the non-advertisement scanning related instruction set;
   selecting a subset of the sensor data;
   preparing a data packet comprising the subset of the sensor data; and
   causing the communication module to transmit the data packet to the receiving device.

2. The analyte monitoring device of claim 1, wherein the communication module is initialized responsive to the detection of expiration of a wakeup timer.

3. The analyze monitoring device of claim 1, wherein initializing the communication module comprises transitioning the communication module from a sleep state to an active state.

4. The analyte monitoring device of claim 3, wherein, after causing the communication module to issue the one or more advertising packets, the one or more processors are further configured to perform operations further comprising:
   determining that the connection request has not been received from the receiving device for a period of time;
   transitioning the communication module from the awake state to the sleep state; and
   initializing the communication module using an advertisement scanning related instruction set a second time, wherein the connection request is received from the receiving device after the communication module has been initialized the second time.

5. The analyte monitoring device of claim 4, wherein the communication module is transitioned from the awake state to the sleep state without executing the non-advertisement scanning related instruction set.

6. The analyte monitoring device of claim 1, wherein the non-advertisement scanning related instruction set includes instructions related to initialization of a random access memory segment or block, initialization of sensing hardware; or initialization of an operating system service.

7. The analyte monitoring device of claim 1, wherein the advertisement scanning related instruction set includes instructions related to detecting expiration of a wake-up timer, processor startup, initialization of a transmit circuit, formation of advertising data packets, transmission of advertising data packets, scanning one or more channels for a connection request from the receiving device, or validating or denying an incoming connection request.

8. The analyte monitoring device of claim 1, wherein the connection request comprises criteria for selecting the subset of the sensor data.

9. The analyte monitoring device of claim 1, wherein the one or more processors are further configured to perform operations further comprising selecting the subset of the sensor data based on a priority level associated with the sensor data.

10. The analyte monitoring device of claim 1, wherein the receiving device is a fitness monitor or fitness device.

11. The analyte monitoring device of claim 1, wherein the receiving device comprises medical components for use by the subject based on the subset of the sensor data.

12. The analyte monitoring device of claim 1, wherein the receiving device is a smartphone or a smartwatch.

13. The analyte monitoring device of claim 1, wherein the one or more processors are further configured to perform operations further comprising establishing a communication session with the receiving device by:
   causing the communication module to transmit an acknowledgement of the connection request to the receiving device; and
   performing a mutual authentication with the receiving device to generate a shared encryption key for subsequent communication sessions.

14. The analyte monitoring device of claim 13, wherein the subset of the sensor data is encrypted in the data packet using the shared encryption key.

15. The analyte monitoring device of claim 1, wherein the analyte comprises glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, or uric acid.

16. One or more computer-readable non-transitory storage media comprising instructions executable by one or more processors of an analyte monitoring device to cause the analyte monitoring device to perform operations comprising:
- generating sensor data indicative of an analyte level measured by an analyte sensor of the analyte monitoring device, wherein at least a portion of the analyte sensor is transcutaneously positioned in contact with a bodily fluid of the subject;
- initializing a communication module of the analyte monitoring device using an advertisement scanning related instruction set, wherein the advertisement scanning related instruction set is a subset of a communications protocol startup instruction set including the advertisement scanning related instruction set and a non-advertisement scanning related instruction set;
- causing the communication module to issue one or more advertising packets;
- receiving a connection request from a receiving device;
- completing initialization of the communication module using the non-advertisement scanning related instruction set;
- selecting a subset of the sensor data;
- preparing a data packet comprising the subset of the sensor data; and
- causing the communication module to transmit the data packet to the receiving device.

17. The one or more computer-readable non-transitory storage media of claim 16, wherein the communication module is initialized responsive to the detection of expiration of a wakeup timer.

18. The one or more computer-readable non-transitory storage media of claim 16, wherein initializing the communication module comprises transitioning the communication module from a sleep state to an active state.

19. The one or more computer-readable non-transitory storage media of claim 18, wherein, after causing the communication module to issue the one or more advertising packets, the instructions are further executable by the one or more processors of the analyte monitoring device to perform further operations comprising:
- determining that the connection request has not been received from the receiving device for a period of time;
- transitioning the communication module from the awake state to the sleep state; and
- initializing the communication module using an advertisement scanning related instruction set a second time, wherein the connection request is received from the receiving device after the communication module has been initialized the second time.

20. A monitoring device comprising:
- one or more processors,
- a sensor configured to be positioned in contact with a subject,
- a communication module, and
- one or more memories communicatively coupled to the one or more processors, the sensor, and the communication module, and comprising instructions executable by the one or more processors to configure the one or more processors to perform operations comprising:
- generating sensor data indicative of monitoring performed by the sensor of the subject;
- initializing the communication module using an advertisement scanning related instruction set, wherein the advertisement scanning related instruction set is a subset of a communications protocol startup instruction set including the advertisement scanning related instruction set and a non-advertisement scanning related instruction set;
- causing the communication module to issue one or more advertising packets;
- receiving a connection request from a receiving device;
- completing initialization of the communication module using the non-advertisement scanning related instruction set;
- selecting a subset of the sensor data;
- preparing a data packet comprising the subset of the sensor data; and
- causing the communication module to transmit the data packet to the receiving device.

* * * * *